United States Patent
Shah et al.

(10) Patent No.: US 12,359,267 B2
(45) Date of Patent: Jul. 15, 2025

(54) COMPOSITIONS AND METHODS FOR AMPLIFYING, DETECTING OR QUANTIFYING HUMAN POLYOMAVIRUS BK VIRUS

(71) Applicant: Gen-Probe Incorporated, San Diego, CA (US)

(72) Inventors: Ankur Shah, San Diego, CA (US); Meghna Yadav, Carlsbad, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 18/749,700

(22) Filed: Jun. 21, 2024

(65) Prior Publication Data

US 2024/0352545 A1    Oct. 24, 2024

Related U.S. Application Data

(62) Division of application No. 17/287,178, filed as application No. PCT/US2019/057383 on Oct. 22, 2019, now Pat. No. 12,054,793.

(60) Provisional application No. 62/748,998, filed on Oct. 22, 2018.

(51) Int. Cl.
| | |
|---|---|
| *C12Q 1/70* | (2006.01) |
| *C12Q 1/6841* | (2018.01) |
| *C12Q 1/6844* | (2018.01) |
| *C12Q 1/6853* | (2018.01) |

(52) U.S. Cl.
CPC ........... *C12Q 1/701* (2013.01); *C12Q 1/6841* (2013.01); *C12Q 1/6844* (2013.01); *C12Q 1/6853* (2013.01)

(58) Field of Classification Search
CPC .. C12Q 1/6841; C12Q 1/6844; C12Q 1/6853; C12Q 1/701
See application file for complete search history.

(56) References Cited

U.S. PATENT DOCUMENTS

| | | | |
|---|---|---|---|
| 8,346,485 B2 | 1/2013 | Archer | |
| 2009/0246754 A1 | 10/2009 | Kiefer et al. | |
| 2013/0267429 A1 | 10/2013 | Gardner et al. | |
| 2016/0215354 A1 | 7/2016 | Dorange | |
| 2018/0127838 A1 | 5/2018 | Mehta et al. | |

FOREIGN PATENT DOCUMENTS

| | | |
|---|---|---|
| CN | 105925678 A | 9/2016 |
| CN | 111733298 A | 10/2020 |
| WO | WO 2007/016275 A2 | 2/2007 |
| WO | WO 2007/100397 A2 | 9/2007 |
| WO | WO 2009/105212 A2 | 8/2009 |
| WO | WO 2009/137137 A2 | 11/2009 |
| WO | WO 2014/197607 A1 | 12/2014 |
| WO | WO 2017/040316 A1 | 3/2017 |
| WO | WO 2017/190487 | 11/2017 |
| WO | WO 2020/007261 A1 | 1/2020 |

OTHER PUBLICATIONS

GenBank Accession No. KT354782.1 dated Nov. 4, 2015.
Greer, et al., "Comparison of BKV quantification using a single automated nucleic acid extraction platform and 3 real-time PCR assays," Diagnostic Microbiology and Infectious Disease, 82(4), 397-302, (2015).
Iwaki, et al., "Development of a real-time quantitative PCR assay for detection of a stable genomic region of BK virus," Virology Journal, 7(1):295, (2010).
AU Application No. 2019365821, Examination Report No. 1 mailed Sep. 11, 2024.
AU Application No. 2019365821, Examination Report No. 2 mailed Nov. 19, 2024.
CN Application No. 201980084809.8, First Office Action mailed Jun. 22, 2024.
CN Application No. 201980084809.8, Office Action mailed Jul. 16, 2024.
JP Application No. 2021-547055, Notice of Reasons for Rejection mailed Aug. 31, 2023.
WIPO Application No. PCT/US2019/057383, PCT International Preliminary Report on Patentability mailed May 6, 2021.
WIPO Application No. PCT/US2019/057383, PCT International Search Report and Written Opinion of the International Searching Authority mailed Dec. 11, 2019.

*Primary Examiner* — Bao Q Li
(74) *Attorney, Agent, or Firm* — Jeffrey E. Landes; Alston & Bird LLP

(57) ABSTRACT

Oligomer nucleotides, compositions, methods, kits, and uses are provided for detecting or quantifying a human polyomavirus BK virus (BKV) nucleic acid, e.g., using nucleic acid amplification and hybridization assays.

20 Claims, No Drawings
Specification includes a Sequence Listing.

COMPOSITIONS AND METHODS FOR AMPLIFYING, DETECTING OR QUANTIFYING HUMAN POLYOMAVIRUS BK VIRUS

CROSS-REFERENCE TO RELATED APPLICATIONS

This application is a divisional application of application Ser. No. 17/287,178, filed Apr. 21, 2021, which is a U.S. National Stage entry of International Application No. PCT/US2019/057383, filed Oct. 22, 2019, which claims the benefit of priority to U.S. Provisional Application Ser. No. 62/748,998, filed Oct. 22, 2018, each of which is incorporated herein by reference.

SEQUENCE LISTING

The Sequence Listing written in filed DIA0089_SeqListing.xml is 76 kilobytes in size, was created Jun. 20, 2024, and is hereby incorporated by reference.

BACKGROUND

Human polyomavirus BK virus (BKV) is a member of the polyomavirus family. The BK virus is similar to another virus called the JC virus (JCV), sharing 75% genomic sequence similarity. BKV have a double strand DNA circular genome with around 5000 base pairs. It is thought that up to 80% of the population contains a latent form of this virus, which remains latent until the body undergoes some form of immunosuppression. Detection of the virus is particularly important for renal and multi-organ transplantation patients, where clinical manifestations include renal dysfunction. From 1-10% of renal transplant patients progress to BKV associated nephropathy (BKVAN) and up to 80% of these patients lose their grafts. BKV is also associated with ureteral stenosis and interstitial nephritis. In bone marrow transplant recipients, BKV can cause hemorrhagic cystitis.

SUMMARY

Described are amplification oligonucleotides, nucleic acids, methods, compositions, and kits for detecting and/or quantifying human polyomavirus BK virus (BKV) in a sample, or to amplify a BKV nucleic acid sequence. The amplification oligonucleotides include amplification primers (first amplification primers and second amplification primers or first primers and second primers). The amplification oligonucleotides further include probe oligonucleotides that facilitate detection of amplified sequence. The methods involve the amplification of viral nucleic acid to detect the BKV target sequence in the sample. The methods can advantageously provide for the sensitive detection of BKV.

The amplification oligonucleotides can be used in the amplification, detection, and/or quantification of a BKV sequence using a variety of nucleic amplification methods known in the art. The nucleic acid amplification methods can use thermal cycling, or they can be isothermal. Nucleic acid amplification methods known in the art include, but are not limited to, polymerase chain reaction (PCR), reverse transcriptase PCR (RT-PCR), real time PCR, nucleic acid sequence-based amplification (NASBA), replicase-mediated amplification (including Qβ-replicase-mediated amplification), ligase chain reaction (LCR), and strand-displacement amplification (SDA).

The described amplification oligonucleotides can be used to amplify and/or detect a BKV sequence. The amplified BKV sequence, the amplicon, includes a sequence present in SEQ ID NO:50 and/or a complement thereof. In some embodiments, the amplified BKV sequence, the amplicon, includes a sequence present in SEQ ID NO:51 and/or a complement thereof. In some embodiments, the amplified BKV sequence, the amplicon, includes a sequence present in SEQ ID NO:52 and/or a complement thereof. In some embodiments, the amplification oligonucleotides are configured to amplify and optionally detect a BKV VP2 amplicon comprising a portion of SEQ ID NO:50, and/or a complement thereof. In some embodiments, the amplification oligonucleotides are configured to amplify and optionally detect a BKV VP2 amplicon comprising a portion of SEQ ID NO:51, and/or a complement thereof. In some embodiments, the amplification oligonucleotides are configured to amplify and optionally detect a BKV amplicon comprising a portion of SEQ ID NO:52, and/or a complement thereof. Various methods in the art can be used to detect a BKV amplicon.

In some embodiments, a first amplification primer comprises 18-30 contiguous nucleobases having at least 90% identity to a nucleotide sequence present in SEQ ID NO:50 or a complement thereof, SEQ ID NO:51 or a complement thereof, and/or SEQ ID NO:52 or a complement thereof. In some embodiments, a first amplification primer comprises a nucleotide sequence having at least 90% identity to a nucleotide sequence selected from the group consisting of: SEQ ID NO:1, SEQ ID NO:4, SEQ ID NO:7, SEQ ID NO:10, SEQ ID NO:13, SEQ ID NO:16, SEQ ID NO:21, SEQ ID NO:24, SEQ ID NO:25, SEQ ID NO:30, SEQ ID NO:31, SEQ ID NO:34, SEQ ID NO:35, SEQ ID NO:38, SEQ ID NO:39, SEQ ID NO: 42, SEQ ID NO:43, SEQ ID NO:46, or SEQ ID NO:47. A first amplification primer is able to hybridize to SEQ ID NO:50, SEQ ID NO:51, and/or SEQ ID NO:52 and initiate DNA polymerization.

In some embodiments, a second amplification primer comprises 19-30 contiguous nucleobases having at least 90% identity to a nucleotide sequence present in SEQ ID NO:50 or a complement thereof, SEQ ID NO:51 or a complement thereof, and/or SEQ ID NO:52 or a complement thereof. In some embodiments, a second amplification primer comprises a nucleotide sequence having at least 90% identity to a nucleotide sequence selected from the group consisting of: SEQ ID NO:2, SEQ ID NO:5, SEQ ID NO:9, SEQ ID NO:12, SEQ ID NO: 14, SEQ ID NO:18, SEQ ID NO:19, SEQ ID NO:22, SEQ ID NO:26, SEQ ID NO: 28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO:45, SEQ ID NO:48, or SEQ ID NO:49. A second amplification primer is able to hybridize to SEQ ID NO:50 or a complement thereof, SEQ ID NO:51 or a complement thereof, and/or SEQ ID NO:52 or a complement thereof and initiate DNA polymerization.

In some embodiments, a first amplification primer comprises a nucleotide sequence having 0, 1, or 2 mismatches to a nucleotide sequence selected from the group consisting of: SEQ ID NO: 1, SEQ ID NO:4, SEQ ID NO:7, SEQ ID NO: 10, SEQ ID NO: 13, SEQ ID NO:16, SEQ ID NO:21, SEQ ID NO:24, SEQ ID NO:25, SEQ ID NO:30, SEQ ID NO:31, SEQ ID NO: 34, SEQ ID NO:35, SEQ ID NO:38, SEQ ID NO:39, SEQ ID NO:42, SEQ ID NO:43, SEQ ID NO:46, or SEQ ID NO:47.

In some embodiments, a second amplification primer comprises a nucleotide sequence having 0, 1, or 2 mismatches to a nucleotide sequence selected from the group consisting of: SEQ ID NO:2, SEQ ID NO:5, SEQ ID NO:9, SEQ ID NO:12, SEQ ID NO: 14, SEQ ID NO:18, SEQ ID NO:19, SEQ ID NO:22, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO:45, SEQ ID NO:48, or SEQ ID NO:49.

In some embodiments, a first amplification primer hybridizes to a first BKV nucleic acid sequence and the second amplification primer hybridizes to a second BKV nucleic acid sequence. The first and second BKV nucleic acid sequences comprise nucleotide sequences present in SEQ ID NO:50 or a complement thereof. In some embodiments, the first and second BKV nucleic acid sequences comprise nucleotide sequences present in SEQ ID NO:51 or a complement thereof. In some embodiments, the first and second BKV nucleic acid sequences comprise nucleotide sequences present in SEQ ID NO:52 or a complement thereof. In some embodiments, the first amplification primer is 80% to 100% complementary to the first BKV nucleic acid sequence and the second amplification primer is 80% to 100% complementary to the second BKV nucleic acid sequence. In some embodiments, the first amplification primer is 90% to 100% complementary to the first BKV nucleic acid sequence and the second amplification primer is 90% to 100% complementary to the second BKV nucleic acid sequence. In some embodiments, the first amplification primer is >90% and <100% complementary to the first BKV nucleic acid sequence and the second amplification primer is >90% and <100% complementary to the second BKV nucleic acid sequence.

The described probe oligonucleotides can be used to detect a BKV nucleic acid including, but not limited to, a BKV amplicon. In some embodiments, a probe oligonucleotide comprises 21-30 contiguous nucleobases having at least 90% identity to a nucleotide sequence present in SEQ ID NO:50 or a complement thereof, SEQ ID NO:51 or a complement thereof, and/or SEQ ID NO:52 or a complement thereof. In some embodiments, a probe oligonucleotide comprises 21-30 contiguous nucleobases that hybridize to SEQ ID NO:50 or a complement thereof, SEQ ID NO:51 or a complement thereof, and/or SEQ ID NO:52 or a complement thereof.

In some embodiments, a probe oligonucleotide comprises a nucleotide sequence having at least 90% identity to a nucleotide sequence selected from the group consisting of: SEQ ID NO:3, SEQ ID NO:6, SEQ ID NO:8, SEQ ID NO: 11, SEQ ID NO: 15, SEQ ID NO: 17, SEQ ID NO:20, SEQ ID NO:23, and SEQ ID NO:27. In some embodiments a probe oligonucleotide comprises a nucleotide sequence having 0, 1, or 2 mismatches to a nucleotide sequence selected from the group consisting of: SEQ ID NO:3, SEQ ID NO:6, SEQ ID NO:8, SEQ ID NO:11, SEQ ID NO:15, SEQ ID NO:17, SEQ ID NO:20, SEQ ID NO:23, and SEQ ID NO: 27.

In some embodiments, the probe oligonucleotide hybridizes to a third BKV nucleic acid sequence. The third BKV nucleic acid sequence comprises a nucleotide sequence present in SEQ ID NO:50 or a complement thereof. In some embodiments, the third BKV sequence comprises a nucleotide sequence present in SEQ ID NO:51 or a complement thereof. In some embodiments, the third BKV sequence comprises a nucleotide sequence present in SEQ ID NO: 52 or a complement thereof. In some embodiments, the probe oligonucleotide is 80% to 100% complementary to the third BKV nucleic acid sequence. In some embodiments, the probe oligonucleotide is 90% to 100% complementary to the third BKV nucleic acid sequence. In some embodiments, the probe oligonucleotide is >90% and <100% complementary to the third BKV nucleic acid sequence.

A probe oligonucleotide can contain a one or more detectable markers or labels. A detectable marker can be, but is not limited to a fluorescent molecule. The label can be attached to the 5' or 3' end of the probe oligonucleotide or anywhere along the oligomer. In some embodiments, a probe oligonucleotide can be a molecular beacon or torch. In some embodiments, a probe oligonucleotide can be a hydrolysis probe. A probe oligonucleotide can contain a fluorescent molecule attached to the 5' end of the probe oligonucleotide and a quencher attached to the 3' end of the probe oligonucleotide or a fluorescent molecule can be attached to the 3' end of the probe oligonucleotide and a quencher attached to the 5' end of the probe oligonucleotide.

Any of the described amplification oligonucleotides (e.g., amplification primers or probe oligonucleotides) can contain at least one modified nucleotide. The modified oligonucleotide can be, but is not limited to, 2'-O-methyl (2'Ome) modified nucleotide, 2'-fluoro modified oligonucleotide, or a 5-methylcytosine. In some embodiments, an amplification oligonucleotide comprises two or more modified nucleotides. The two or more modified nucleotides may have the same or different modifications. In some embodiments, any of the described amplification oligonucleotides can contain one or more 5-methylcytosines. 5-methylcytosine includes 5-methyl-deoxycytosine (5-Me-dC, 5-methyl-2'-deoxycytosine). An amplification oligonucleotide can have 0, 1, 2, 3, 4, 5, 6, 7, 8, or more 2'-O-methyl modified nucleotides, 2'-fluoro modified oligonucleotides, 5-methylcytosines, or combinations thereof. In some embodiments, all cytosine nucleotides in an amplification oligonucleotide are 5-methylcytosine modified nucleotides. In some embodiments, 5-methyl-2'-deoxycytosine bases can be used to increase the stability of the duplex by raising the Tm by about 0.5°-1.3° C. for each 5-methyl-2'-deoxycytosine incorporated in an oligomer, relative to the corresponding unmethylated oligomer.

Any of the described amplification primers or probe oligonucleotides can contain at least degenerate position. A degenerate position refers to a position on a nucleobase sequence that can have multiple possible alternatives. In some embodiments, a first amplification primer, second amplification primer, and/or probe oligonucleotide contains 0, 1, 2, 3, 4, or 5 degenerate positions. A degenerate position can be, but is not limited to, R (A or G), W (A or T), M (A or C), Y (C or T), K (G or T), B (A or G or T), D (A or G or T), H (A or C or T), N (A or G or C or T), S (G or C), or V (A or C or G). For an oligonucleotide having two or more degenerate positions, the degeneracy at any given position is independent of the degeneracy at another position.

The described amplification primers can be used to amplify a BKV sequence. In some embodiments, the BKV sequence comprises a VP2 sequence. In some embodiments, the BKV sequence comprises an LT sequence. In some embodiments, the described amplification primers can be used to amplify a BKV sequence using a thermal cycling reaction such as polymerase chain reaction (PCR). In some embodiments, the described amplification primers can be used to amplify an BKV sequence using an isothermal reaction such as transcription-mediated amplification (TMA). Other nucleic acid amplification methods that can utilize the described amplification oligonucleotides include, but are not limited to, nucleic acid sequence-based amplification (NASBA), replicase-mediated amplification, ligase chain reaction (LCR), strand-displacement amplification (SDA), reverse transcriptase PCR (RT-PCR), and real time PCR.

In some embodiments, a first amplification primer is combined with a second amplification primer to form an amplification primer pair. In some embodiments, a first amplification primer and second amplification primer are configured to amplify a BKV nucleic acid sequence about 100 to about 150 nucleotides (base pairs) in length. In some embodiments, a first amplification primer and second amplification primer are configured to amplify a BKV nucleic acid sequence (i.e., produce a BKV amplicon) 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides (base pairs) in length.

Described are compositions and kits for amplifying, detecting and/or quantifying BKV, a BKV nucleic acid, or a nucleic acid derived from a BKV nucleic acid. In some embodiments, the described compositions and kits provide for the direct, rapid, specific, and/or sensitive detection of BKV. The compositions and kits can comprise one or more of the described amplification oligonucleotides, and/or probe oligonucleotides. In some embodiments, a composition or kit comprises at least one first amplification primer and at least one second amplification primer. A composition or kit may further comprise at least one probe oligonucleotide. A composition or kit may further comprise any one or more of: BKV positive control nucleic acid, negative control nucleic acid, nucleotide triphosphates, DNA polymerase, Sample Transport Medium, and instructions for use.

Described are methods for amplifying, detecting, and/or quantifying a BKV target sequence, the methods comprising the steps of contacting a sample containing or suspected of containing BKV, a BKV nucleic acid, or a nucleic acid derived from BKV, with at least two amplification primers for amplifying a target nucleic acid of a BKV, wherein the at least two amplification primers comprise a first amplification primer and a second amplification primer as described above that each hybridize to a BKV nucleic acid sequence. An in vitro nucleic acid amplification reaction is performed, wherein any BKV target nucleic acid, if present in the sample, is used as a template for generating an amplification product. In some embodiments, the first and second amplification primer each hybridize to SEQ ID NO:50 or a complement thereof. In some embodiments, the first and second amplification primers each hybridize to SEQ ID NO:51 or a complement thereof. In some embodiments, the first and second amplification primers each hybridize to SEQ ID NO:52 or a complement thereof.

In some embodiments, the methods further include detecting the presence or absence of the amplification product, thereby indicating the presence or absence of BKV in the sample. The amplification product is detected using a probe oligonucleotide. The described probe oligonucleotides can be used in amplification reactions to detect and/or quantify BKV in a sample.

In some embodiments, quantification of BKV in samples can be used to aid in the management of solid organ transplant recipients. In patients receiving anti-BKV therapy, BKV DNA measurements can be used to assess viral response to treatment. The viral load information may also be used to diagnose BKV disease in transplant patients.

DETAILED DESCRIPTION

A. Definitions

Before describing the present teachings in detail, it is to be understood that the disclosure is not limited to specific compositions or process steps, as such may vary. It should be noted that, as used in this specification and the appended claims, the singular form "a," "an," and "the" include plural references unless the context clearly dictates otherwise. Thus, for example, reference to "an oligomer" includes a plurality of oligomers and the like. The conjunction "or" is to be interpreted in the inclusive sense, i.e., as equivalent to "and/or," unless the inclusive sense would be unreasonable in the context.

In general, the term "about" indicates insubstantial variation in a quantity of a component of a composition not having any significant effect on the activity or stability of the composition. When the specification discloses a specific value for a parameter, the specification should be understood as alternatively disclosing the parameter at "about" that value. All ranges are to be interpreted as encompassing any cited numeral (fractional or integral) within the indicated range and the endpoints of the range in the absence of express exclusions such as "not including the endpoints"; thus, for example, "10-15" includes the values 10 and 15 and whole and fraction numbers between 10 and 15, e.g., 12.67. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components. Embodiments in the specification that recite "consisting essentially of" various components are also contemplated as "consisting of". "Consisting essentially of" means that additional component(s), composition(s) or method step(s) that do not materially change the basic and novel characteristics of the compositions and methods described herein may be included in those compositions or methods. Such characteristics include the ability to detect a BKV nucleic acid sequence present in a sample with specificity that distinguishes the BKV nucleic acid from other known pathogens, optionally at a sensitivity that can detect about 1-100 copies of the virus within about 45 min from the beginning of an amplification reaction that makes amplified viral sequences that are detected.

A "sample" is any sample containing or suspected of containing a BKV, a BKV nucleic acid and/or a nucleic acid derived from a BKV or BKV nucleic acid. A "sample" may contain or may be suspected of containing BKV or components thereof, such as nucleic acids or fragments of nucleic acids. A sample may be a complex mixture of components. Samples include biological samples or clinical samples or specimens which include any tissue or material derived from a living or dead mammal or organism, including, e.g., lower respiratory tract specimen, bronchoalveolar lavage specimen, sputum, tracheal aspirates, blood, plasma, serum, blood cells, saliva, and mucous, cerebrospinal fluid (to diagnose BKV infections of the central nervous system) and samples-such as biopsies—from or derived from genital lesions, anogenital lesions, oral lesions, mucocutaneous lesions, skin lesions and ocular lesions or combinations thereof. Samples may also include samples of in vitro cell culture constituents including, e.g., conditioned media resulting from the growth of cells and tissues in culture medium. A sample may be treated to physically, chemically, or mechanically disrupt tissue or cell structure to release intracellular nucleic acids into a solution which may contain enzymes, buffers, salts, detergents and the like, to prepare the sample for analysis. In some embodiments, samples may include processed samples, such as those obtained from passing samples over or through a filtering device, or following centrifugation, or by adherence to a medium, matrix, or support.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., 11$^{th}$ ed., 1992), derivatives of purines or pyrimidines (e.g., N$^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, 5-methylcytosine, O$^6$-methylguanine, 4-thio-pyrimidines, 4-amino-pyrimidines, 4-dimethylhydrazine-pyrimidines, and O$^4$-alkyl-pyrimidines; U.S. Pat. No. 5,378,825 and PCT No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43 (42): 13233-41). Nucleic acids may include modified bases to alter the function or behavior of the nucleic acid, e.g., addition of a 3'-terminal dideoxy-nucleotide to block additional nucleotides from being added to the nucleic acid. Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

A "target nucleic acid" or "target" is a nucleic acid containing a target nucleic acid sequence. A "target nucleic acid sequence," "target sequence" or "target region" is contiguous nucleotide sequence, where the amplification oligonucleotides anneal and comprises a nucleotide sequence of a target organism, such as BKV, to be amplified and/or detected. A target sequence, or a complement thereof, contains sequences that hybridize to amplification primers, and/or detection probes used to amplify and/or detect the target nucleic acid. The target nucleic acid may include other sequences besides the target sequence which may not be amplified. Target nucleic acids may be DNA or RNA and may be either single-stranded or double-stranded. A target nucleic acid can be, but is not limited to, a genomic nucleic acid, a transcribed nucleic acid, such as an rRNA, or a nucleic acid derived from a genomic or transcribed nucleic acid. The contiguous nucleotide sequence between the forward and reverse amplification primers defines the polynucleotide to be amplified.

Unless otherwise indicated, "hybridizing to a BKV nucleic acid" includes hybridizing to either a sense or antisense strand of BKV nucleic acid or to an RNA transcribed from the genomic sequence.

In some embodiments, an amplification oligonucleotide, amplification primer, probe oligonucleotide, or target capture oligomer contains one or more modified nucleotides. An amplification oligonucleotide can have 1, 2, 3, 4, 5, 6, 7, 8, or more modified nucleotides. Modified nucleotides include nucleotides having modified nucleobases. Modified nucleobases include, but are not limited to, synthetic and natural nucleobases, 5-substituted pyrimidines, 6-azapyrimidines, and N-2, N-6 and O-6 substituted purines. Modified nucleotides also include nucleotides with a modified base, including, but not limited to, 2'-modified nucleotides (including, but not limited to 2'-O-methyl nucleotides and 2'-halogen nucleotides, such as 2'-fluoro nucleotides).

"C residues" include methylated (e.g., 5-methylcytosine) and unmethylated cytosines unless the context indicates otherwise.

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. RNA and DNA equivalents are molecules having the same sequence of bases except that T in DNA is replaced by U in RNA.

An "oligomer" or "oligonucleotide" refers to a nucleic acid of generally less than 1,000 nucleotides (nt), including those in a size range having a lower limit of about 2 to 5 nt and an upper limit of about 500 to 900 nt. In some embodiments, oligomers have a size range with a lower limit of about 15, 16, 17, 18, 19, or 20 nt and an upper limit of about 30-60 nt. In some embodiments, an oligonucleotide has up to 30, 35, 40, 45, 50, 55, or 60 nt. Oligomers may be purified from naturally occurring sources, or may be synthesized by using any known enzymatic or chemical method. Oligomers may be referred to by a functional name (e.g., first amplification primer, second amplification primer, promoter-primer, probe oligonucleotide, helper oligomer, displacer oligomer, and target capture oligomer) but those skilled in the art will understand that such terms refer to oligomers.

With respect to alignment of two nucleotide sequences, a "mismatch" is a nucleotide difference between two sequences. A mismatch can be a substitution (of one nucleobase for another), an insertion, or a deletion. With respect to hybridization, a "mismatch" refers to a non-Watson Crick base pair.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as a target nucleic acid. An amplicon may be single stranded or double stranded.

An "amplification primer" or "primer" refers to an oligonucleotide that hybridizes to a target nucleic acid, or its complement, and participates in a nucleic acid amplification reaction. An amplification primer hybridizes to a template nucleic acid and has a 3'-OH (3'-hydroxyl) group that can be extended by polymerization. In some embodiments, an amplification primer is single stranded. In some embodiments, an amplification primer is substantially single stranded, containing a self-complementary region of no more than 5 contiguous base pairs. In some embodiments, an amplification primer is 15-60, 15-55, 15-50, 15-45, 15-40, 15-35, 15-30 nucleobases in length. In some embodiments, an amplification primer is 18-30 nucleobases in length. In some embodiments, and amplification primer is 18-60 nucleobases in length and contains 18-30 contiguous nucleobases (target hybridizing region) that hybridize to a corresponding 18-30 nucleotide oligo hybridizing sequence present in the target nucleic acid sequence. In some embodiments, the 18-30 contiguous nucleobases are at the 3' end of the amplification primer. An amplification primer can be a primer, first amplification primer, forward amplification primer, second amplification primer, or reverse amplification primer. In some embodiments, amplification primers contain at least about 10 contiguous bases, and optionally at least 15, 16, 17, 18, 19, 20, 21, 22, 23, 24, 25, 26, 27, 28, 29, or 30 contiguous bases, that are complementary to a region of the target nucleic acid sequence or its complementary strand. The contiguous bases may be at least about 80%, at least about 90%, at least 95%, or completely complementary to the target nucleic acid sequence to which the amplification primer binds. In some embodiments, an amplification oligomer contains additional 3' or 5' sequences that are not complementary to the target nucleic acid sequence. One skilled in the art will understand that the recited ranges include all whole and rational numbers within the range (e.g., 92% or 98.377%). Amplification primers optionally may include modified nucleotides and/or degenerate positions. In some embodiments, an amplification primer contains at least one methylated cytosine and/or at least one 2'-modified nucleotide. In some embodiments, an amplification primer contains 1, 2, 3, 4, 5, 6, 7, or 8 2'-O-methyl modified nucleotides, 2'-fluoro modified nucleotides, 5-methylcytosines, or combinations thereof. An amplification primer may optionally be modified, e.g., by including a 5' region that is non-target-complementary to the target sequence. Such modification can include functional additions, such as tags, promoters, or other sequences used or useful for manipulating or amplifying the amplification primer or target oligonucleotide.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308), and strand-displacement amplification (SDA) (e.g., U.S. Pat. No. 5,422,252). Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target sequence and its complementary strand by using multiple cycles of hybridization, ligation, and denaturation. SDA uses a primer that contains a recognition site for a restriction endonuclease that will nick one strand of a hemi-modified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription-mediated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al., each of which is incorporated herein by reference). Methods that use TMA are described in detail previously (U.S. Pat. Nos. 5,399,491 and 5,554,516, each of which is incorporated herein by reference).

In cyclic amplification methods that detect amplicons in real-time, the term "Threshold cycle" (Ct) is a measure of the emergence time of a signal associated with amplification of target sequence, and is generally 10× standard deviation of the normalized reporter signal. Once an amplification reaches the "threshold cycle," generally there is considered to be a positive amplification product of a sequence to which the probe oligonucleotide binds. The identity of the amplification product can then be determined through methods known to one of skill in the art, such as gel electrophoresis, nucleic acid sequencing, and other such well known methods.

The term "relative fluorescence unit" ("RFU") is a unit of measurement of fluorescence intensity. RFU varies with the characteristics of the detection means used for the measurement, and can be used as a measurement to compare relative intensities between samples and controls. The analytical sensitivity (limit of detection or LoD) is determined from the median tissue culture infective dose ($TCID_{50}$/mL). The $TCID_{50}$/mL is the amount of a pathogenic agent that will produce pathological change in 50% of cell cultures inoculated.

"Probe oligonucleotide," "detection probe," or "probe" refers to an oligomer that hybridizes specifically to a target sequence, including an amplified sequence, under conditions that promote nucleic acid hybridization, for detection of the target nucleic acid sequence. Detection may either be direct (i.e., probe oligonucleotide hybridized directly to the target nucleic acid sequence) or indirect (i.e., a probe oligonucleotide hybridized to an intermediate structure that links the probe oligonucleotide to the target nucleic acid sequence). A probe oligonucleotide's target sequence generally refers to a specific sequence within a larger sequence to which the probe oligonucleotide hybridizes specifically. In some embodiments, a probe oligonucleotide is 15-60, 15-55, 15-50, 15-45, 15-40, 15-35, or 15-30 nucleobases in length. In some embodiments, a probe oligonucleotide is 20-60 nucleobases in length and contains 20-30 contiguous nucleobases that hybridize to a corresponding 20-30 nucleotide oligo hybridizing sequence present in the target nucleic acid sequence. A probe oligonucleotide may include target-specific sequences and a non-target-complementary sequence. Such non-target-complementary sequences can include sequences which will confer a desired secondary or tertiary structure, such as a hairpin structure, which can be used to facilitate detection and/or amplification. (e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1). Probe oligonucleotides of a defined sequence may be produced by techniques known to those of ordinary skill in the art, such as by chemical synthesis, and by in vitro or in vivo expression from recombinant nucleic acid molecules.

The term "non-target-specific sequence" or "non-target-complementary sequence" refers to a region of an oligomer wherein the region does not anneal to a complementary oligo hybridizing sequence in the target nucleic acid under standard hybridization conditions. More specifically, the non-target-specific sequence is not complementary to target sequence contiguous with the oligo hybridizing sequence in the target nucleic acid. Such non-target-specific sequence can be complementary to a portion of a target-specific sequence in the oligonucleotide. In some embodiments, a non-target-complementary sequence is 4, 5, 6, 7, or 8 nucleobases in length. Examples of oligomers with non-target-specific sequences include, but are not limited to, molecular beacons.

Detection can be achieved using single-stranded nucleic acid probe oligonucleotides that are present during target amplification and hybridize to the amplicon in real time. In some embodiments, detection in real time comprises real time PCR. Exemplary probe oligonucleotides include hydrolysis probes, torches, and molecular beacons. A probe oligonucleotide may contain a fluorophore and a quencher. Torches contain complementary regions at each end. In some embodiments, one of the complementary regions is a non-target complementary sequence. The complementary regions (e.g., the non-target-complementary sequence and its complementary region in the probe) can be 4, 5, 6, 7, or 8 nucleobases in length. These complementary regions bind to each other and form a "closed" torch. In the closed configuration, the fluorophore and quencher are in close proximity and the fluorophore signal is quenched. That is, it does not emit a detectable signal when excited by light. However, when the torch binds to the complementary target sequence, the complementary regions within the torch are forced apart to form an "open" torch. In the open form, the fluorophore and quencher are not in close proximity and the fluorophore signal is detectable when excited (i.e., no longer quenched). Amplicon-torch binding results in the separation of the quencher from the fluorophore; which allows fluorophore excitation in response to light stimulus and signal emission at a specific wavelength. The torches can be present during amplification and bind to the complementary amplicon as it is generated in real time. As more amplicon is created, more torch is bound and more signal is created. The signal eventually reaches a level that it can be detected above the background and ultimately reaches a point where all available torch is bound to amplicon and the signal reaches a maximum. At the start of amplication, and low copy number of the amplified sequence, most of the probe oligonucleotide is closed (the 3' and 5' complementary regions are base paired, and the fluorescent signal is quenched). During amplification, more probe oligonucleotide binds to target sequence, thus separating the 3' and 5' ends (complementary regions) of the probe oligonucleotide, leading to increases fluorescence (decreased quenching of fluorescence). After further amplification, the fluorescent signal approaches a maximum.

"Hydrolysis probes" are one of the sequence-specific chemistries available for real-time PCR. The methodology of hydrolysis probes is based on the 5' nuclease assay. Hydrolysis probes are often referred to as TAQMAN™ (hydrolysis) probes. Hydrolysis probes are dual-labelled oligonucleotides. The 5' end of the oligonucleotide is labelled with a fluorescent reporter molecule while the 3' end is labelled with a quencher molecule. The sequence of the hydrolysis probe is specific for a region of interest in the amplified target sequence. The hydrolysis probe is designed so that the length of the sequence places the 5' fluorophore and the 3' quencher in close enough proximity so as to suppress fluorescence. Hydrolysis probes bind a region of interest between the binding sites for the amplification primers. During the extension phase of the PCR cycle Taq DNA polymerase synthesizes the complementary strand downstream of the PCR amplification primers. When extension reaches the bound hydrolysis probe, the 5'-3' exonuclease activity of the Taq DNA polymerase degrades the hydrolysis probe. Cleavage of the hydrolysis probe separates the fluorescent reporter molecule from the rest of the probe allowing the reporter molecule to fluoresce. With subsequent PCR cycles the amount of fluorescent reporter released, and hence fluorescence, increases cumulatively. In some embodiments, a hydrolysis probe is 20-30 nucleobases in length without any stem-loop, self-hybridization or other secondary structure. A hydrolysis probe does not contain sequence complementarity to the amplification primers or overlap with their binding sites. In some embodiments, the annealing temperature of the hydrolysis probe is about 5-7° C. higher than that of the first and second amplification primers. In some embodiments, the annealing temperature of the hydrolysis probe is about 5° C., about 6° C., or about 7° C. higher than that of the first and second amplification primers.

The term "complementary" or "sufficiently complementary" denotes the particular nucleotide base pairing relationship between two single-stranded polynucleotides (e.g., amplification oligonucleotide and target nucleic acid sequence) or two different regions of the same single-stranded polynucleotide (e.g., molecular beacon) that allows for hybridization (e.g., the formation of stable, double-stranded hybrid). Complementary sequences need not be completely complementary (100% complementary) to form a stable duplex. In some embodiments, partially complementary (less than 100% complementary, due to mismatches to standard nucleic acid base pairing) sequences remain sufficiently complementary provided they allow for the polynucleotide sequences to anneal. A percent complementarity indicates the percentage of bases, in a contiguous strand, in a first nucleic acid sequence which can form hydrogen bonds (e.g., Watson-Crick base pair) with a second nucleic acid sequence (e.g., 5, 6, 7, 8, 9, 10 out of 10 being 50%, 60%, 70%, 80%, 90%, and 100% complementary). Percent complementarity is calculated in a similar manner to percent identify. IN canonical base pairs, purine bases hydrogen bond to pyrimidine bases, with adenine pairing with thymine or uracil (A and T or U) and guanine pairing with cytosine (C and G). Base pairing can also form between bases which are not members of these canonical pairs. Non-canonical base pairing is well-known to a person of ordinary skill in the art of molecular biology (see, e.g., R. L. P. Adams et al., The Biochemistry of the Nucleic Acids (11th ed. 1992)). Appropriate hybridization conditions are well-known to a person of ordinary skill in the art of molecular biology, and can be predicted based on sequence composition, or can be determined empirically by using routine testing (e.g., Sambrook et al., Molecular Cloning, A Laboratory Manual, 2nd ed. at §§ 1.90-1.91, 7.37-7.57, 9.47-9.51 and 11.47-11.57, particularly §§ 9.50-9.51, 11.12-11.13, 11.45-11.47 and 11.55-11.57).

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters or by inspection and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences.

"Self-complementarity" refers an oligonucleotide containing internal complementary sequences that can hybridize to each other, creating a double-strand structure or region within the oligonucleotide. Depending on the location of the complementary sequences within the oligonucleotide, hybridization of the sequences can lead to formation of hairpin loops, junctions, bulges or internal loops. In some embodiments, the self-complementary sequences can each be 4-6 nucleobases in length. In some embodiments, the self-complementary sequences are located at the 5' and 3' ends of the oligonucleotide. In some embodiments, a self-complementary sequence can be added to the 5' or 3' end of an oligonucleotide, such as a detection probe.

By "hybridization" or "hybridize" is meant the ability of two completely or partially complementary nucleic acid sequences to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (Sec, e.g., R. L. P. Adams et al., *The Biochemistry of the Nucleic Acids* (11th ed. 1992).)

By "preferentially hybridize" is meant that under stringent hybridization conditions, an amplification primer or probe oligonucleotide can hybridize to its target nucleic acid to form stable oligomer: target hybrids, but not form a sufficient number of stable oligomer: non-target hybrids. Amplification primers and detection oligomers that preferentially hybridize to a target nucleic acid are useful to amplify and/or detect target nucleic acids, but not non-targeted nucleic acids, especially in phylogenetically closely-related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target nucleic acid as appropriate. In general, reducing the degree of complementarity between an oligonucleotide sequence and its target sequence will decrease the degree or rate of hybridization of the oligonucleotide to its target sequence. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference, at least a 20-fold difference, at least a 50-fold difference, at least a 100-fold difference, at least a 200-fold difference, at least a 500-fold difference, or at least a 1,000-fold difference between target and non-target hybridization signals in a test sample. In some embodiments, non-target hybridization signals in a test sample are no more than the background signal level.

By "stringent hybridization conditions," or "stringent conditions" is meant conditions permitting an oligonucleotide to preferentially hybridize to a target nucleic acid (such as a BKV nucleic acid) and not to nucleic acid derived from a closely related non-target nucleic acids. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from one or more strains of BKV with the oligomers of the present disclosure correspond to a temperature of about 60° C. when the salt concentration is in the range of about 0.6-0.9 M. Specific hybridization assay conditions are set forth infra in the Examples section. Other acceptable stringent hybridization conditions could be easily ascertained by those having ordinary skill in the art.

By "competes for hybridization to a BKV nucleic acid under stringent conditions" with a referenced oligomer is meant that an oligomer substantially reduces the binding of the referenced oligomer to its BKV target sequence under stringent conditions, the competing oligomer when supplied in excess can reduce binding of the referenced oligomer at a sub-saturating concentration by about 20%, 30%, 40%, 50%, or more, or the Tm of the competing oligomer is higher than or within about 5, 4, 3, 2, or 1° C. of the Tm of the referenced oligomer to the target. Suitable oligonucleotide competition assay conditions and procedures are known in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe oligonucleotide that is detectable or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal). Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Embodiments of fluorophores include those that absorb light in the range of about 495 to 650 nm and emit light in the range of about 520 to 670 nm, which include those known as FAM (fluorescein), TET™ (Tetrachlorofluorescein), CAL FLUOR™ (Orange or Red), and QUASAR™ compounds. Fluorophores may be used in combination with a quencher molecule that absorbs light when in close proximity to the fluorophore. Such quenchers are well known in the art and include, e.g., BLACK HOLE QUENCHER™ (or BHQ™, including, but not limited to, Black Hole Quencher-2 (BHQ2)) or TAMRA compounds. Particular embodiments include a "homogeneous detectable label" that is detectable in a homogeneous system in which bound labeled probe oligonucleotide in a mixture exhibits a detectable change compared to unbound labeled probe oligonucleotide, which allows the label to be detected without physically removing hybridized from unhybridized labeled probe oligonucleotide (e.g., U.S. Pat. Nos. 5,283,174, 5,656,207, and 5,658,737). Particular homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual,* 2nd cd. (Cold Spring Harbor Laboratory Press, Cold Spring Harbor, NY, 1989) at Chapt. 10, and U.S. Pat. Nos. 5,658, 737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe oligonucleotide's central region and near a region of A/T base pairs, at a probe oligonucleotide's 3' or 5' terminus, or at or near a mismatch site with a known sequence that is the probe oligonucleotide should not detect compared to the desired target sequence. Other detectably labeled probe oligonucleotides include TAQMAN™ (hydrolysis) probes, molecular torches, and molecular beacons. TAQMAN™ (hydrolysis) probes include a donor (fluorophore) and acceptor (quencher) label wherein fluorescence is detected upon enzymatically degrading the probe oligonucleotide during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probe oligonucleotides.

Sequences are "sufficiently complementary" if they allow stable hybridization of two nucleic acid sequences, e.g., stable hybrids of probe oligonucleotide and target sequences, although the sequences need not be completely complementary. Sufficiently complementary sequence hybridizes to another sequence by hydrogen bonding between a subset series of complementary nucleotides by using canonical base pairing (e.g., G:C, A:T, or A:U). The two sequences may contain one or more residues (including abasic positions) that are not complementary so long as the entire sequences, in appropriate hybridization conditions, form a stable hybridization complex. Sufficiently complementary sequences may be at least about 80%, at least about 90%, or completely complementary over the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual,* $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

References, particularly in the claims, to "the sequence of SEQ ID NO:X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated.

References, particularly in the claims, to "a nucleotide sequence present in SEQ ID NO: X" refer to a base sequence occurring in the corresponding sequence listing entry and do not require identity of the backbone (e.g., RNA, 2'-O-Me RNA, or DNA) or base modifications (e.g., methylation of cytosine residues) unless otherwise indicated. A base sequence occurring in the corresponding sequence may comprise all or a portion of the entire base sequence of the corresponding sequence listing entry. A portion of the entire base sequence of the corresponding sequence listing entry may occur anywhere within the corresponding sequence listing entry. The portion of the entire base sequence of the corresponding sequence listing entry may be any length, including, but not limited to, 2-50 contiguous nucleobases.

A "degenerate" position in an oligonucleotide refers to a position where more than one base is present in a population of oligonucleotides. Each position in the degenerate sequence region can have two or more possible nucleobase alternatives. The nucleotide alternatives at a degenerate position can be present in equal amounts, or with equal probability. For example, a nucleotide can be presented as Y, which represents C or T. The degenerate position can be, but is not limited to, R (A or G), W (A or T), M (A or C), Y (C or T), K (G or T), B (A or G or T), D (A or G or T), H (A or C or T), N (A or G or C or T), S (G or C), or V (A or C or G). Oligomers with degenerate positions can be synthesized by providing a mixture of nucleotide precursors corresponding to the desired degenerate combination at the step of the synthesis where incorporation of a degenerate position is desired. Oligonucleotides may be synthesized as degenerate. Alternatively, oligonucleotides may be synthesized as individual species and then subsequently mixed.

A "non-Watson Crick" (NWC) position in an oligomer refers to a position where the oligomer is configured to hybridize to at least one BKV target sequence with a non-Watson Crick base pairing, such as G-U, G-T, or G-A (either the G or the U/T/A can be the base in the oligomer). In some embodiments, the NWC position is configured to hybridize via a wobble (G-U or G-T) or purine-purine (G-A) pair.

The term "thermostable" or "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90-100° C. under conditions such as are typically required for PCR amplification.

The term "PCR amplifying" or "PCR amplification" refers generally to cycling polymerase-mediated exponential amplification of nucleic acids employing amplification primers that hybridize to complementary strands. Devices have been developed that can perform thermal cycling reactions with compositions containing fluorescent indicators which are able to emit a light beam of a specified wavelength, read the intensity of the fluorescent dye, and display the intensity of fluorescence after each cycle.

Unless defined otherwise, all scientific and technical terms used herein have the same meaning as commonly understood by those skilled in the relevant art. General definitions may be found in technical books relevant to the art of molecular biology, e.g., "Dictionary of Microbiology and Molecular Biology, 2nd ed." (Singleton et al., 1994, John Wiley & Sons, New York, NY) or "The Harper Collins Dictionary of Biology" (Hale & Marham, 1991, Harper Perennial, New York, NY).

Oligomers

Amplification primers suitable for amplification of the BKV target sequence can be found in Table 1A. Probe oligonucleotides suitable for detection of a BKV amplicon can be found in Table 1B. The BKV Target region, which contains the regions to be amplified, are shown in Table 1C.

TABLE 1A

Amplification primer oligonucleotide sequences.

| Sequence | SEQ ID NO. |
|---|---|
| First Amplification primers | |
| ctagaacttctactcctccttttatta | 1 |
| gcagcaaacccagcaatagc | 4 |
| gactctgtaaaagactcctaggtaag | 7 |
| ttagttcyttggctcaagtaggg | 10 |
| ccctacttgagccaargaactaa | 13 |
| cctttcttttkgttggggc | 16 |
| gggttaaacaattccaawgccat | 21 |
| ggcctaacwcctcaaacatatgc | 24 |
| gaaagagctgcctgggaaa | 25 |
| ttagttctttggctcaagtaggg | 30 |
| ttagttccttggctcaagtaggg | 31 |

TABLE 1A-continued

Amplification primer oligonucleotide sequences.

| Sequence | SEQ ID NO. |
|---|---|
| ccctacttgagccaaggaactaa | 34 |
| ccctacttgagccaaagaactaa | 35 |
| ccttttcttttggttggggc | 38 |
| cctttcttttgttggggc | 39 |
| gggttaaacaattccaaagccat | 42 |
| gggttaaacaattccaatgccat | 43 |
| ggcctaacacctcaaacatatgc | 46 |
| ggcctaactcctcaaacatatgc | 47 |
| Second Amplification primers | |
| ggccccaacmaaaagaaaagg | 2 |
| ccttgctactgtagagggcataac | 5 |
| gcagcagcctcagatacactggc | 9 |
| gggttaaacaattccaawgccatgcc | 12 |
| ggcctaacwcctcaaacatatgc | 14 |
| aaaactattgccccaggaggtgct | 18 |
| ttagttcyttggctcaagtaggta | 19 |
| ccctacttgagccaargaactaa | 22 |
| ctacctttacatcytgctccattt | 26 |
| ggccccaacaaaaagaaaagg | 28 |
| ggccccaaccaaaagaaaagg | 29 |
| gggttaaacaattccaaagccatgcc | 32 |
| gggttaaacaattccaatgccatgcc | 33 |
| ggcctaacacctcaaacatatgc | 36 |
| ggcctaactcctcaaacatatgc | 37 |
| ttagttctttggctcaagtaggta | 40 |
| ttagttccttggctcaagtaggta | 41 |
| ccctacttgagccaaggaactaa | 44 |
| ccctacttgagccaaraaactaa | 45 |
| ctacctttacatcttgctccattt | 48 |
| ctacctttacatcctgctccattt | 49 |

TABLE 1B

Probe oligonucleotide sequences.

| Sequence | SEQ ID NO. |
|---|---|
| ggcttttggggagctgccctgga | 3 |
| agcaccagcaattacagcatatgtttgagg | 6 |
| atgggtgctgctctagcacttttggg | 8 |
| attgggatcacaaagtttccactgtaggc | 11 |
| ttaaagcagcaaacccagcaatagcc | 15 |
| acagtcccgtacaggcctagaag | 17 |
| gcctacagtggaaactttgtgatcccaat | 20 |
| ggctattgctgggtttgctgctttaa | 23 |
| ccctgacaaaggggcgacgaggataaaa | 27 |

TABLE 1C

BKV gene target region sequence.

BKV Sequence, GenBank Accession Number AB269857.1 (SEQ ID NO: 50)
gcctcggcctcttatatattataaaaaaaaaggccacagggaggagctgctttcccatggaatgcagccaaacc
atgacctcaggaaggaaagtgcatgactgggcagccagccagtggcagttaatagtgaaaccccgcccctagaa
ttctcaaatsaaacacaagaggaagtggaaagtagccaaaggagtggaaagcagccagacagacatgttttgcga
gccgaggaatcttggccttgtccccagttaatactggacaaaggccatggttctacgccagctgtcacgacaag
cttctgtgaaagttagtaaaacctggactggaactaaaaaaagagctcagaggattcttatttttattttagag
cttttgctggaattttgtagaggtgaagacagtgtagacgggaaaaacaaaagtaccactgctttacctgctgt TABLE 1C-continued BKV gene target region sequence.

```
aaaagactctgtaaaagactcctaggtaagtaatccctttttttttgtatttccaggttcatgggtgctgctct
agcacttttgggggacctagttgccagtgtatctgaggctgctgctgccacaggattttcagtggctgaaattg
ctgctggggaggctgctgctgctatagaagttcaaattgcatcccttgctactgtagagggcataacaagtacc
tcagaggctatagctgctataggcctaactcctcaaacatatgctgtaattgctggtgctccaggggctattgc
tgggtttgctgctttaattcaaactgttactggtattagttcttttggctcaagtagggtataggttttttagtg
attgggatcacaaagtttccactgtaggcctttatcagcaatcaggcatggcattggaattgtttaacccagat
gagtactatgatattttgtttcctggtgtaaatacttttgtaaataatattcaatacctagatcctaggcattg
gggtccttctttgtttgctactatttcccaggctttgtggcatgttattagggatgatatacctgctataactt
cacaagaattgcaaagaagaacagagagattcttagagactccttggctagattttggaagaaactacctgg
acaattgtaaatgccctgtaaacttttataattatattcaggattattattctaatttgtccctattaggcc
ttcaatggttaggcaagttgctgaaagggaaggaacccaggtaaattttggccatacctacagaatagatgatg
ctgacagtatacaagaagttacccaaagaatggagttaagaaataaagagaatgtacattcaggagagtttata
gaaaaaactattgccccaggaggtgctaatcaaagaactgctcctcaatggatgttgcctttgcttctaggcct
gtacgggactgtaacacctgctcttgaagcatatgaagatggccccaaccaaaagaaaaggagagtgtccaggg
gcagctcccaaaaagccaaaggaacccgtgcaagtgccaaaactactaataaaaggaggagtagaagttctaga
agttaaaactggggtagatgctataacagaagtagaatgctttctaaatccagaaatgggggatccagataatg
acctagggctatagtctaagactaactgctgaaactgcctttgacagtgatagcccagacagaaaatgctt
ccctgttacagcacagcaagaattccactacctaatttgaatgaggatctaacctgtggaaatctactaatgtg
ggaggctgtgactgtaaaaacagaggttattggaataactagtatgcttaaccttcatgcagggtcacagaaag
tacatgaaaatggtggaggcaaacctattcaaggcagcaattttcacttttttgctgtgggtggggaccccttg
gaaatgcagggagtacttatgaactacagaacaaagtacccagaaggtactgtcaccccaaaaaatcccacagc
tcagtcccaggtaatgaatactgaccataaggcctacttggacaaaaacaatgcttatccgttgaatgctgga
ttcctgaccctagtagaaatgaaaatactaggtattttggaacatacacaggaggggaaaatgttccccacagta
cttcatgtaaccaacacagctaccacagtgttgctggatgaacagggtgtggggcctctgtgtaaagctgatag
cctgtatgtttcagctgctgatatttgtggactgtttactaacagctctggaacacaacagtggagggccttc
caagatatttaagattcgcctgagaaaaagatctgtaaagaaccccttacccaatttcctttttgcttagtgac
cttataaacaggagaacccagagagtggatgggcagcctatgtatggtatggagtctcaggtggaggaggtcag
ggtgtttgatggcacagaacagcttccaggggacccagatatgataagatatattgacagacagggacaattgc
aaacaaaaatggtttaaacaaggtgcttttattgtacatatacatgcttaataaatgctgcttttatattaca
cattttaatcttgtgttatttgggggtggtgttttaggccttttaaaacactgaaagcctttacacaaatgta
actcttcactatgggggtctagcctttgggaatcttcagcaggggctgaagtatctgagactttgggaagagcat
tgtgattgagattcagtgcttgatccagtgtccagagtcttcagttttctgaatcttcttctcttgttatatcaag
aatacatttccccatgcatatattatattttcatccttgaaaaagtatacatacttatctcagaatccagccttt
ccttccattcaacaattctagactgtatatcttgtgcaaaatcagctacaggcctgaaccaaattagcagtagc
agcaaggtcattccactttgtaatattcttttttcaagtaaaaattctgagttttgcagggattttcttaaata
aattttaggtctaaaatctatctgtcttacaaatctagcctgcaagcctggagttggggagtactcattcattg
taactaaacctggtggaaatatttgggttcttttgtttaagtgtttcttttctaaattaactttgacacttcca
tctaaataatccctaaactgtctaaattgtttattccatgtcctgaaggcaaatcctttgattcagctcctgt
tcccttcacatcttcaaaaacaaccatatactgatctatagccacacccagttcaaaagtaagcctttccatgg
gtaaattcacatttaaagcttttgcctccacataaatctaataacccctgcagctagtgttgttttttccactatca
attggacctttgaataaccagtatcttcttttaggtacattaaaaacaatacagtgcaggaaatcaaatataac
agaatccatttaggtagcaaacagtgcagccaggcaactcctgccatatattgttctagtacagcatttccat
gagctccaaatattaaatccatttatctaatatatgattaaatctgtctgttagcatttcttctctggtcata
tggagggtatctacccttttttttagctaacactgtatccacctgtgctgacaaatactttttagtttttact
ttctgcaaaaatggtagcatttgcaaaatgcttttcatgatatttaaagtggtaggggttggtcttttttttgac
acttttttacactcctctacattgtactgaaattctaaatacatacccaatagtagaaacacatcttcacacttt
gtttctactgcatattcagttattaatttccaggacacctgctttgtttcttcaggttcctctgggttaaaatc
atgctcctttaggccccccttgaatacttcctctattatataatatggatctctagttaaggcactgtatagta
agtattccttattaacaccccttacaaattaaaaaactaaaagtacacagcttttgacagaaattattaattgca
gaaactctatgtctatgtggagttaaaaagaataataatattatgaccagcacacatgtgtctactaataaaagt
tacagaatattttttccataagttttttatacagaattaaagcttttttctttagtagtatacacagcaaagcagg
caagagttctattactaaatacagcttgactaagaaactggtgtgagtcagaaggaaagtcttaggggtcttct
acctttctttttttttggggtggtgttgagtgtttgggaatctgctgttgcctcctcatcactggcaaacatatc
ttcatgcagaataaatcttcatcccattttttcattaaaggacctccaccaggactcccactcttctgttccat
aggttggcacctataaaaaaaacataattacttagggccttcctataatttactattatctaaagataaattag
ttaccttaaagctttagatctctgaagggagtctctccaattatttggacccaccattgcagagtttcttcagt
taggtctaagccaaaccactgtgtgaagcagtcaatgcagtagcaatctatccaaaccaagggctcttttctta
aaaattttctatttaaatgtcttaatcttagctgacacagcatgcaagggcagtgcacagaaggcttttggaa
caaataggccattccttgcagtacagggtatctgggcaaagaggaaaatcagcacaaacctctgagctactcca
ggttccaaaatcaggctggtgagctacctttacatcctgctccatttttttatataaagtattcattctcttca
ttttatcctcgtcgcccccttttgtcagggtgaaattccttacattgttcttaaataggctttcctcattaaggga
aggtttccccaggcagctctttcaaggcctaaaaggtccatgagcttccatggattcctccctgtttagcacttt
atccattttgcaaaaaattgcaaaagaataggggatttccccaaatagttttgctaggcctcagaaaaagcctc
cacacccttactacttgagagaaagggtggaggcagaggcg
```

SEQ ID NO: 51 (VP2 gene sequence)
```
gactctgtaaaagactcctaggtaagtaatccctttttttttgtatttccaggttcatgggtgctgctctagca
cttttgggggacctagttgccagtgtatctgaggctgctgctgccacaggattttcagtggctgaaattgctgc
tggggaggctgctgctgctatagaagttcaaattgcatcccttgctactgtagagggcataacaagtacctcag
aggctatagctgctataggcctaactcctcaaacatatgctgtaattgctggtgctccaggggctattgctggg
tttgctgctttaattcaaactgttactggtattagttcttttggctcaagtagggtataggttttttagtgattg
ggatcacaaagtttccactgtaggcctttatcagcaatcaggcatggcattggaattgtttaacccagatgagt
actatgatattttgtttcctggtgtaaatacttttgtaaataatattcaatacctagatcctaggcattgggggt
ccttctttgtttgctactatttcccaggctttgtggcatgttattagggatgatatacctgctataacttcaca
agaattgcaaagaagaacagagagattcttagagactccttggctagattttggaagaaactacctggacaa
ttgtaaatgccctgtaaacttttataattatattcaggattattattctaatttgtccctattaggccttca
atggttaggcaagttgctgaaagggaaggaacccaggtaaattttggccatacctacagaatagatgatgctga
cagtatacaagaagttacccaaagaatggagttaagaaataaagagaatgtacattcaggagagtttatagaaa
```

TABLE 1C-continued

BKV gene target region sequence.

aaactattgccccaggaggtgctaatcaaagaactgctcctcaatggatgttgcctttgcttctaggcctgtac
gggactgtaacacctgctcttgaagcatatgaagatggccccaaccaaaagaaaaggagagtgtccaggggcag
ctcccaaaaagccaaaggaacccgtgcaagtgccaaaactactaataaaaggaggagtagaagttctagaagtt
a SEQ ID NO: 52 (LT amplicon)
ctacctttacatcctgctccatttttttatataaagtattcattctcttcattttatcctcgtcgcccctttg
tcagggtgaaattccttacactttcttaaataggctttcctcattaagggaaggtttccccaggcagctctttc The described amplification oligonucleotides are configured to hybridize specifically to a BKV nucleic acid or a nucleic acid derived from BKV. In some embodiments, certain described amplification primers are configured to hybridize specifically to a BKV VP2 gene nucleic acid a nucleic acid derived from BKV VP2 gene. In some embodiments, the amplification oligonucleotides have target-hybridizing regions from about 18-30 bases in length or about 18, 19, 20, 21, 22, 23, 24, 25, 26, 27, 28, 29, or 30 bases in length.

In some embodiments, an amplification oligonucleotide comprises of any of the sequences of Table 1A. In some embodiments, an amplification primer is 18-30 nucleobases in length and comprises a nucleotide sequence having at least 90% identity to any of the sequences of Table 1A. In some embodiments, an amplification primer is 18-30 nucleobases in length and comprises a nucleotide sequence having 0, 1, or 2 mismatches to of any of the sequences of Table 1A. In some embodiments, an amplification primer is 18-30 nucleobases in length and comprises a nucleotide sequence of any of the sequences of Table 1A. In some embodiments, an amplification primer consists of any of the sequences of Table 1A. In some embodiments, an amplification primer comprises an oligomer that competes with any of the sequences in Table 1A for binding to a BKV nucleic acid under stringent conditions. The BKV nucleic acid can be, but is not limited to, SEQ ID NO:50 or a complement thereof, SEQ ID NO: 51 or a complement thereof, and SEQ ID NO:52 or a complement thereof. In some embodiments, an amplification primer is 18-60 nucleobases in length and contains a target hybridizing region 18-30 nucleobases in length, wherein the target hybridizing region has the nucleotide sequence of any of the sequences of Table 1A.

In some embodiments, a first and/or second amplification primer comprises an oligomer capable of competing with any of SEQ ID NO:1, 2, 4, 5, 7, 9, 10, 12, 13, 14, 16, 18, 19, 21, 22, 24, 25, 26, 28, 29, 30, 31, 32, 33, 34, 35, 36, 37, 38, 39, 40, 41, 42, 43, 44, 45, 46, 47, 48, and/or 49 for hybridizing to SEQ ID NO:50 or a complement thereof.

In some embodiments, the first amplification primer hybridizes to a first BKV nucleic acid sequence and the second amplification primer hybridizes to a second BKV nucleic acid sequence. In some embodiments, the first amplification primer is 90% to 100% complementary to the first BKV nucleic acid sequence and the second amplification primers is 90% to 100% complementary to the second BKV nucleic acid sequence. In some embodiments, the first amplification primer is >90% and <100% complementary to the first BKV nucleic acid sequence and the second amplification primer is >90% and <100% complementary to the second BKV nucleic acid sequence. In some embodiments, the first amplification primer contains 0, 1, or 2 mismatches to the first BKV nucleic acid sequence and the second amplification primer contains 0, 1, or 2 mismatches to the second BKV nucleic acid sequence.

In some embodiments, a first amplification primer (first primer) and a second amplification primer (second primer) are configured to amplify a BKV amplicon. In some embodiments, the first amplification primer and second amplification primer are configured to amplify a BKV VP2 amplicon. In some embodiments, the BKV amplicon is about 90 to about 150 nucleotides in length. In some embodiments, a first amplification primer and second amplification primer are configured to amplify a BKV amplicon 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides (or base pairs) in length.

In some embodiments, a first amplification primer comprises the nucleotide sequence of SEQ ID NO:13 and a second amplification primer comprises the nucleotide sequence of SEQ ID NO: 14.

In some embodiments, a first amplification primer comprises the nucleotide sequence of SEQ ID NO: 1 and a second amplification primer comprises the nucleotide sequence of SEQ ID NO: 2.

In some embodiments, a first amplification primer comprises the nucleotide sequence of SEQ ID NO:4 and a second amplification primer comprises the nucleotide sequence of SEQ ID NO: 5.

In some embodiments, a first amplification primer comprises the nucleotide sequence of SEQ ID NO:7 and a second amplification primer comprises the nucleotide sequence of SEQ ID NO: 9.

In some embodiments, a first amplification primer comprises the nucleotide sequence of SEQ ID NO:10 and a second amplification primer comprises the nucleotide sequence of SEQ ID NO:12.

In some embodiments, a first amplification primer comprises the nucleotide sequence of SEQ ID NO:16 and a second amplification primer comprises the nucleotide sequence of SEQ ID NO:18.

In some embodiments, a first amplification primer comprises the nucleotide sequence of SEQ ID NO:21 and a second amplification primer comprises the nucleotide sequence of SEQ ID NO:19.

In some embodiments, a first amplification primer comprises the nucleotide sequence of SEQ ID NO:24 and a second amplification primer comprises the nucleotide sequence of SEQ ID NO:22.

In some embodiments, a first amplification primer comprises the nucleotide sequence of SEQ ID NO:25 and a second amplification primer comprises the nucleotide sequence of SEQ ID NO:26.

In some embodiments, a first amplification primer comprises the nucleotide sequence of SEQ ID NO:13 and one or more second amplification primers comprise the nucleotide sequences of SEQ ID NO:36 and/or SEQ ID NO:37.

In some embodiments, one or more first amplification primers comprise the nucleotide sequences of SEQ ID NO:35 and/or SEQ ID NO:36 and a second amplification primer comprises the nucleotide sequence of SEQ ID NO:14.

In some embodiments, one or more first amplification primers comprise the nucleotide sequences of SEQ ID NO:35 and/or SEQ ID NO:36 and one or more second amplification primers comprise the nucleotide sequences of SEQ ID NO:36 and/or SEQ ID NO: 37.

In some embodiments, a first amplification primer comprises the nucleotide sequence of SEQ ID NO:1 and one or more second amplification primers comprise the nucleotide sequences of SEQ ID NO:28 and/or SEQ ID NO:29.

In some embodiments, a first amplification primer comprises the nucleotide sequence of SEQ ID NO:10 and one or more second amplification primers comprise the nucleotide sequences of SEQ ID NO:32 and/or SEQ ID NO:33.

In some embodiments, one or more first amplification primers comprise the nucleotide sequences of SEQ ID NO:30 and/or SEQ ID NO:31 and a second amplification primer comprises the nucleotide sequence of SEQ ID NO:12.

In some embodiments, or more first amplification primers comprise the nucleotide sequences of SEQ ID NO:30 and/or SEQ ID NO:31 and one or more second amplification primers comprise the nucleotide sequences of SEQ ID NO:32 and/or SEQ ID NO:33.

In some embodiments, one or more first amplification primers comprise the nucleotide sequences of SEQ ID NO:38 and/or SEQ ID NO:39 and a second amplification primer comprises the nucleotide sequence of SEQ ID NO:18.

In some embodiments, a first amplification primer comprises the nucleotide sequence of SEQ ID NO:21 and one or more second amplification primers comprise the nucleotide sequences of SEQ ID NO:40 and/or SEQ ID NO:41.

In some embodiments, one or more first amplification primers comprise the nucleotide sequences of SEQ ID NO:42 and/or SEQ ID NO:43 and a second amplification primer comprises the nucleotide sequence of SEQ ID NO:19.

In some embodiments, one or more first amplification primers comprise the nucleotide sequences of SEQ ID NO:42 and/or SEQ ID NO:43 and one or more second amplification primers comprise the nucleotide sequences of SEQ ID NO:40 and/or SEQ ID NO: 41.

In some embodiments, a first amplification primer comprises the nucleotide sequence of SEQ ID NO:24 and one or more second amplification primers comprise the nucleotide sequences of SEQ ID NO:44 and/or SEQ ID NO:45.

In some embodiments, one or more first amplification primers comprise the nucleotide sequences of SEQ ID NO:46 and/or SEQ ID NO:47 and a second amplification primer comprises the nucleotide sequence of SEQ ID NO:22.

In some embodiments, one or more first amplification primers comprise the nucleotide sequences of SEQ ID NO:46 and/or SEQ ID NO:47 and one or more second amplification primers comprise the nucleotide sequences of SEQ ID NO:44 and/or SEQ ID NO: 45.

In some embodiments, a first amplification primer comprises the nucleotide sequence of SEQ ID NO:25 and one or more second amplification primers comprise the nucleotide sequences of SEQ ID NO:48 and/or SEQ ID NO:49.

The first and second amplification primers are capable of initiating DNA polymerization. In some embodiments, the first and second amplification primers are compatible with thermostable DNA polymerase. In some embodiments, the first and second amplification primers are compatible with DNA polymerase from *Thermophilus aquaticus* (Taq). In some embodiments, the first and second amplification primers are capable of initiating DNA polymerization by Taq.

In some embodiments, an amplification oligonucleotide is provided that comprises a detectable label (label). Such an amplification oligonucleotide can be used as a probe oligonucleotide. In some embodiments, the probe oligonucleotide is used to detect the presence or absence of a BKV amplification product made using the described amplification primers.

A probe oligonucleotide can be used to detect a BKV amplicon, i.e., the probe oligonucleotide hybridizes to the BKV amplicon. The BKV amplicon can be generated using any of the described amplification primers. In some embodiments, a probe oligonucleotide comprises 21, 22, 23, 24, 25, 26, 27, 28, 29, or 30 contiguous nucleobases 90%-100% complementary to 21-30 contiguous bases in the BKV amplicon.

The described probe oligonucleotides are configured to hybridize specifically to a BKV nucleic acid. In some embodiments, a probe oligonucleotide is configured to hybridize specifically to a BKV VP2 gene nucleic acid.

In some embodiments, a probe oligonucleotide comprises of any of the sequences of Table 1B. In some embodiments, a probe oligonucleotide is 21-30 nucleobases in length and comprises a nucleotide sequence having at least 90% identity to of any of the sequences of Table 1B. In some embodiments, a probe oligonucleotide is 21-30 nucleobases in length and comprises a nucleotide sequence having 0, 1, or 2 mismatches to of any of the sequences of Table 1B. In some embodiments, a probe oligonucleotide is 21-30 nucleobases in length and comprises a nucleotide sequence of any of the sequences of Table 1B. In some embodiments, a probe oligonucleotide consists of any of the sequences of Table 1B. In some embodiments, a probe oligonucleotide comprises an oligomer that competes with any of the sequences in Table 1B for binding to a BKV nucleic acid under stringent conditions. The BKV nucleic acid can be, but is not limited to, SEQ ID NO:50 or a complement thereof, SEQ ID NO:51 or a complement thereof, and SEQ ID NO:52 or a complement thereof. In some embodiments, an amplification primer is 21-60 nucleobases in length and contains a target hybridizing region 21-30 nucleobases in length, wherein the target hybridizing region has the nucleotide sequence of any of the sequences of Table 1B.

In some embodiments, a probe oligonucleotide comprises an oligomer capable of competing with any of SEQ ID NO:3, 6, 8, 11, 15, 17, 20, 23, and 27 for hybridizing to SEQ ID NO: 50 or a complement thereof.

In some embodiments, the probe oligonucleotide hybridizes to an amplified BKV nucleic acid sequence. In some embodiments, the probe oligonucleotide is 90% to 100% complementary to an amplified BKV nucleic acid sequence. In some embodiments, the probe oligonucleotide is >90% and <100% complementary to an amplified BKV nucleic acid sequence. In some embodiments, the probe oligonucleotide contains 0, 1, or 2 mismatches to an amplified BKV nucleic acid sequence.

In some embodiments, the detectable label is a non-nucleotide label. Suitable labels include compounds that emit a detectable light signal, e.g., fluorophores or luminescent (e.g., chemiluminescent) compounds that can be detected in a homogeneous mixture. More than one label, and/or more than one type of label, may be present on a particular probe oligonucleotide, or detection may rely on using a mixture of probe oligonucleotides in which each probe oligonucleotide is labeled with a compound that produces a detectable signal (see. e.g., U.S. Pat. Nos. 6,180,340 and 6,350,579, each incorporated by reference herein). Labels may be attached to a probe oligonucleotide by various means including covalent linkages, chelation, and ionic interactions, but in some embodiments the label is covalently attached. For example, in some embodiments, a probe oligonucleotide has an attached chemiluminescent label such as, e.g., an acridinium ester (AE) compound (see. e.g., U.S. Pat. Nos. 5,185,439; 5,639,604; 5,585,481; and 5,656,744). A label, such as a fluorescent or chemiluminescent label, can be attached to the probe oligonucleotide by a non-nucleotide linker (see e.g., U.S. Pat. Nos. 5,585,481; 5,656,744; and 5,639,604).

Examples of detectable labels include, but are not limited to, fluorescein, tetramethylrhodamine, IAEDANS, EDANS, DABCYL, coumarin, BODIPY FL, lucifer yellow, eosine, erythrosine, tetramethylrhodamine, Texas Red, CY5, fluorescein/QSY7 dye, and the like.

In some embodiments, a probe oligonucleotide (e.g., comprising a fluorescent label) further comprises a second label that interacts with the first label. For example, the second label can be a quencher. Such probe oligonucleotides can be used, e.g., in TAQMAN™ (hydrolysis probe) assays, where hybridization of the probe oligonucleotide to a target sequence or amplicon followed by nucleolysis by a polymerase comprising 5'-3' exonuclease activity results in liberation of the fluorescent label and thereby increased fluorescence, or fluorescence independent of the interaction with the second label.

Examples of interacting donor/acceptor label pairs that may be used in connection with the disclosure, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, CalRed-610/BHQ-2, lucifer yellow/DABCYL, Quasar 750/BHQ-2, BODIPY/DABCYL, eosine/DABCYL, erythrosine/DABCYL, tetramethylrhodamine/DABCYL, Texas Red/DABCYL, CY5/BHQ1, CY5/BHQ2, CY3/BHQ1, CY3/BHQ2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. In some embodiments, non-fluorescent acceptors, such as DABCYL and the QSY7 dyes, reduce or eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL, BlackBerry, and the BLACK HOLE QUENCHER moieties which are available from Glen Research, (Sterling, VA), Berry & Associates, Inc., (Dexter, MI), and Biosearch Technologies, Inc., (Novato, CA).

In some embodiments, a probe oligonucleotide is non-extendable (i.e., it is blocked). For example, the probe oligonucleotide can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

Any of the described amplification oligonucleotides (e.g., amplification primers and probe oligonucleotides) can contain at least one modified nucleotide. The modified oligonucleotide can be, but is not limited to, a 2'-O-methyl modified nucleotide, a 2'-fluoro modified oligonucleotide, or a 5-methylcytosine. In some embodiments, an amplification oligonucleotide comprises two or more modified nucleotides. The two or more modified nucleotides may be the same or different. In some embodiments, any of the described amplification oligonucleotides can contain one or more 5-methylcytosines. An amplification oligonucleotide can have 1, 2, 3, 4, 5, 6, 7, 8, or more 2'-O-methyl modified nucleotides, 2'-fluoro modified oligonucleotides, 5-methylcytosines, or combinations thereof. In some embodiments, all cytosine nucleotides in an amplification oligonucleotide are 5-methylcytosine modified nucleotides. In some oligomers, 5-methyl-2'-deoxycytosine bases can be used to increase the stability of the duplex by raising the Tm by about 0.5°-1.3° C. for each 5-methyl-2'-deoxycytosine incorporated in an oligonucleotide (relative to the corresponding unmethylated oligomer).

Compositions and Kits

The present disclosure provides amplification oligonucleotides, compositions, and kits, useful for amplifying, detecting, and/or quantifying BKV in a sample.

Also provided by the disclosure are reaction mixtures for determining the presence or absence of a BKV target nucleic acid or quantifying the amount thereof in a sample. A reaction mixture in accordance with the present disclosure comprises at least one or more of the following: an amplification primer pair as described herein for amplification of a BKV target nucleic acid sequence and a probe oligonucleotide as described herein for determining the presence or absence of a BKV amplification product. In some embodiments, any amplification primer pair described herein can be provided in a kit. A composition, kit and/or reaction mixture may further include a number of optional components. For an amplification reaction mixture, a reaction mixture will typically include other reagents suitable for performing in vitro amplification such as, e.g., buffers, salt solutions, appropriate nucleotide triphosphates (e.g., dATP, dCTP, dGTP, and dTTP; and/or ATP, CTP, GTP and UTP), and/or enzymes (e.g., a thermostable DNA polymerase, reverse transcriptase, and/or RNA polymerase), and optionally include test sample components, in which a BKV target nucleic acid may or may not be present. A reaction mixture may include amplification oligonucleotides for only one target region of a BKV genome, or it may include amplification oligonucleotides for multiple BKV target regions. In addition, for a reaction mixture that includes a probe oligonucleotide together with an amplification primer pair, selection of amplification primer pair and probe oligonucleotides for a reaction mixture are linked by a common target region (i.e., the reaction mixture will include a probe oligonucleotide that binds to a sequence amplifiable by an amplification primer pair of the reaction mixture). In some embodiments, a kit can contain amplification oligonucleotides for amplifying and/or detecting BKV and amplification oligonucleotides for detecting one or more other, non-BKV, organisms. In some embodiments, a kit or reaction mixture contains an amplification primer pair. The first and second amplification primers of the pair can be provided in a single container or separate containers. In some embodiments, a kit or reaction mixture contains a probe oligonucleotide. In some embodiments, a kit or reaction mixture contains an amplification primer pair and a probe oligonucleotide. The amplification primers and probe oligonucleotide can be provided in a single container or separate containers.

In some embodiments, the reaction mixture comprises KCl. In some embodiments, the KCl concentration is about 50 mM. In some embodiments, the KCl concentration is greater than about 50 mM, e.g., about 60-150 mM, about 75-125 mM, about 80-120 mM, about 85-115 mM, or about 90-110 mM. In some embodiments, the KCl concentration is 55-65, 65-75, 75-85, 85-95, 95-105, 105-115, 115-125, 125-135, or 135-145, wherein each of the foregoing is in mM and is optionally modified by "about". In some embodiments, a composition according to the disclosure comprises KCl, e.g., at any of the foregoing concentrations. In some embodiments, a method according to the disclosure comprises performing an amplification reaction in the presence of KCl, e.g., at any of the foregoing concentrations.

In some embodiments, amplification oligonucleotides are provided, e.g., in a kit or composition. Amplification oligonucleotides generally comprise a target-hybridizing region, e.g., configured to hybridize specifically to a BKV nucleic acid.

In some embodiments, a pair of amplification primers is provided wherein one amplification primer is configured to hybridize to a sense strand of a BKV nucleic acid and the other is configured to hybridize to an anti-sense strand of a BKV nucleic acid. Such amplification primers include amplification primer pairs for PCR, transcription-mediated amplification, or other forms of amplification known in the art.

In some embodiments, one or more amplification oligonucleotides, such as an amplification primer pair, a probe oligonucleotide, or a combination thereof are configured to hybridize to a BKV nucleic acid sequence. In some embodiments, one or more amplification oligonucleotides, such as an amplification primer pair, probe oligonucleotide or combination thereof, are configured to hybridize to a BKV VP2 gene. In some embodiments, one or more amplification oligonucleotides, such as an amplification primer pair, probe oligonucleotide, or combination thereof, are configured to hybridize to a BKV sequence represented by SEQ ID NO: 50 and/or a complement thereof, SEQ ID NO:51 and/or a complement thereof, or SEQ ID NO: 52 and/or a complement thereof. In some embodiments, one or more internal control probe oligonucleotides are also provided.

In some embodiments, one or more amplification oligonucleotides comprises a degenerate position. In some embodiments, a BKV amplification primer, a BKV amplification primer pair, and/or a BKV probe oligonucleotide comprises a degenerate position. In some embodiments, one or more amplification oligonucleotides comprises a non-Watson Crick (NWC) position. In some embodiments, a BKV amplification primer, a BKV amplification primer pair, and/or a BKV probe oligonucleotide comprises a NWC position.

In some embodiments, one or more amplification oligonucleotides in a set, kit, composition, or reaction mixture comprise a methylated cytosine (e.g., 5-methylcytosine). In some embodiments, an amplification oligonucleotide contains 1, 2, 3, 4, 5, 6, 7, 8, or more 2'-O-methyl modified nucleotides, 2'-fluoro modified oligonucleotides, 5-methylcytosines, or combinations thereof. In some embodiments, at least about half of the cytosines in an amplification oligonucleotide are methylated. In some embodiments, all or substantially all (e.g., all but 1-2) of the cytosines in an amplification oligonucleotide are methylated. In some embodiments, a cytosine at the 3' end or within 2, 3, 4, or 5 bases of the 3' end is unmethylated.

In some embodiments, a composition or kit comprises a probe oligonucleotide that comprises a detectable marker. In some embodiments, a composition or kit comprises a probe oligonucleotide that comprises a fluorescent label and a quencher. A fluorescent label and a quencher can be, but are not limited to: 6'-carboxy-X-rhodamine (ROX) and acridine quencher, and fluorescein (FAM) with DABCYL quencher. In some embodiments, a composition or kit comprises a two or more probe oligonucleotides. The two or more probe oligonucleotides may detect the same amplicon (i.e., amplified target sequence) of different amplicons. The different amplicons may be from the same or different organisms (including viruses). In some embodiments, the two or more probe oligonucleotides contain different detectable labels that can be distinguished from each other. In some embodiments, the different detectable labels are fluorophores that emit light at different wavelengths.

In some embodiments, a kit, composition, or reaction mixture additionally contains one or more of: DNA polymerase, positive control nucleic acid, negative control nucleic acid, internal control nucleic acid, deoxyribonucleotides (i.e., dNTPs (e.g., dATP, dTTP, dGTP, and dCTP)), KCl, $MgCl_2$, potassium acetate, buffer, BSA, sucrose, trehalose, DMSO, betaine, formamide, glycerol, polyethylene glycol, non-ionic detergents, ammonium ions, EDTA, and other reagents or buffers suitable for PCR amplification. The DNA polymerase can be, but is not limited to, thermostable DNA polymerase (e.g., Taq polymerase). The buffer can be, but is not limited to, Tris-HCl and Tris-acetate. The nonionic detergent can be, but is not limited to, Tween-20 and Triton X-100. In some embodiments, a kit, composition, or reaction mixture comprises the components necessary to amplify and optionally detect, one or more target nucleic acid sequences.

In some embodiments, a kit further includes a set of instructions for practicing methods in accordance with the present disclosure, where the instructions may be associated with a package insert and/or the packaging of the kit or the components thereof.

Any method disclosed herein is also to be understood as a disclosure of corresponding uses of materials involved in the method directed to the purpose of the method. Any of the amplification oligonucleotides comprising BKV sequence and any combinations (e.g., kits and compositions) comprising such amplification oligonucleotides are to be understood as also disclosed for use in detecting and/or quantifying BKV or in amplifying a BKV nucleic acid sequence, and for use in the preparation of a composition for detecting and/or quantifying BKV, or in amplifying a BKV nucleic acid sequence.

Methods of Amplifying, Detecting and or Quantifying BKV

Described are methods of detecting and/or quantifying BKV or in amplifying a BKV nucleic acid sequence using one or more of the amplification oligonucleotides, compositions, or kits as described above. In some embodiments, the described amplification oligonucleotides can be used to detect BKV present in a sample at less than or equal to 50 copies, less than or equal to 40 copies, less than or equal to 30 copies, less than or equal to 20 copies, or less than or equal to 10 copies. In some embodiments, the detection rate, using the described oligonucleotides is greater than or equal to 95% when the BKV is present at 10, 20, 30, 40, 50, or more copies per sample.

In some embodiments, the described amplification primers and probe oligonucleotides can be used to amplify and/or detect BKV in clinical samples or contrived clinical samples. In some embodiments, the described amplification primers and probe oligonucleotides can be used to amplify, detect, and/or quantify one or more strains of BKV. In some embodiments, the described amplification primers and probe oligonucleotides exhibit little to no cross-reactivity with organisms commonly found in plasma, serum, or urine. In some embodiments, the described amplification primers and probe oligonucleotides can be used to detect BKV in the presence of organisms commonly found in plasma, serum, or urine. In some embodiments, the described amplification primers and probe oligonucleotides for BKV can be used to amplify and/or detect BKV in the presence to other amplification primers and probe oligonucleotide used to detect nucleic acid from one or more organism other than BKV or to a different region in BVK. In some embodiments, the organism other than BKV is CMV and EBV In some embodiments, the described amplification primers and probe oligonucleotides for BKV have a shelf-life of at least 3 months, at least 6 months, at least 9 months, at least 12 months, at least 15 months, at least 18 months, or at least 24 months from date of manufacture.

Broadly speaking, the methods can comprise one or more of the following components: amplification, and amplicon detection and/or quantification, which may be performed in real time with amplification. Certain embodiments involve each of the foregoing steps.

In some embodiments, amplification comprises contacting the sample with at least two oligomers for amplifying a BKV nucleic acid target region corresponding to a BKV target nucleic acid, where the oligomers include at least two amplification primers as described above (e.g., one or more oriented in the sense direction and one or more oriented in the antisense direction); (2) performing an in vitro nucleic acid amplification reaction, wherein BKV target nucleic acid, if present in the sample, can used as a template for generating an amplification product; and (3) detecting the presence or absence of the amplification product, thereby determining the presence or absence of BKV in the sample, or quantifying the amount of BKV nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the BKV target nucleic acid from other components in the sample, e.g., before amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In some embodiments, the methods include sample preparation. Sample preparation refers to any steps or methods required to prepare a sample for amplification and/or detection. Sample preparation may include any known method of purifying or concentrating components, such as polynucleotides, from a larger sample volume, such as by filtration of airborne or waterborne particles from a larger volume sample or by isolation of microbes from a sample by using standard microbiology methods. Sample preparation may also include physical disruption and/or mechanical disruption and/or chemical lysis of cellular components to release intracellular components into a substantially aqueous or organic phase and removal of debris. Sample preparation may also include use of a polynucleotide to selectively or non-specifically capture a target nucleic acid and separate it from other sample components (e.g., as described in U.S. Pat. No. 6,110,678 and International Patent Application Pub. No. WO 2008/016988, each incorporated by reference herein).

Non-specific target capture methods may involve selective precipitation of nucleic acids from a substantially aqueous mixture, adherence of nucleic acids to a support that is washed to remove other sample components, or other means of physically separating nucleic acids from a mixture that contains BKV nucleic acid and other sample components.

Amplifying a BKV target sequence utilizes an in vitro amplification reaction using at least two amplification primers that flank a target region to be amplified. In some embodiments, at least first and second amplification primers as described above are used to amplify the target sequence. The amplification reaction can be thermal cycled or isothermal. Suitable amplification methods include, but are not limited to, replicase-mediated amplification, polymerase chain reaction (PCR), ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence, such as, e.g., by hybridizing the amplification product with a labeled probe oligonucleotide and detecting a signal resulting from the labeled probe oligonucleotide (including from label released from the probe oligonucleotide following hybridization in some embodiments). In some embodiments, the labeled probe oligonucleotide comprises a second moiety, such as a quencher or other moiety that interacts with the first label, as discussed above. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In some embodiments, the detection step allows homogeneous detection, e.g., detection of the hybridized probe oligonucleotide without removal of unhybridized probe oligonucleotide from the mixture (see. e.g., U.S. Pat. Nos. 5,639,604 and 5,283,174). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use probe oligonucleotides that are configured to specifically hybridize to sequences in the amplified products and detecting the presence of the probe oligonucleotide:

product complexes, or by using a complex of probe oligonucleotides that may amplify the detectable signal associated with the amplified products (e.g., U.S. Pat. Nos. 5,424,413; 5,451,503; and 5,849,481; each incorporated by reference herein). Directly or indirectly labeled probe oligonucleotides that specifically associate with the amplified product provide a detectable signal that indicates the presence of the target nucleic acid in the sample. In particular, the amplified product will contain a target sequence in or complementary to a sequence in the BKV genome, and a probe oligonucleotide will bind directly or indirectly to a sequence contained in the amplified product to indicate the presence of BKV nucleic acid in the tested sample.

In some embodiments that detect the amplified product near or at the end of the amplification step, a linear probe oligonucleotide may be used to provide a signal to indicate hybridization of the probe oligonucleotide to the amplified product. One example of such detection uses a luminescent labeled probe oligonucleotide that hybridizes to target nucleic acid. Luminescent label is then hydrolyzed from non-hybridized probe oligonucleotide. Detection is performed by chemiluminescence using a luminometer (see, e.g., International Patent Application Pub. No. WO 89/002476). In some embodiments that use real-time detection, the probe oligonucleotide may be a hairpin probe such as, for example, a molecular beacon, molecular torch, or hybridization switch probe that is labeled with a reporter moiety that is detected when the probe oligonucleotide binds to amplified product. Such probe oligonucleotides may comprise target-hybridizing sequences and non-target-hybridizing sequences.

LIST OF EMBODIMENTS

1. Amplification oligonucleotides for amplifying a BK polyomavirus (BKV) nucleic acid sequence comprising,
    a) one or more first amplification primers wherein each first amplification primer is 18-30 nucleobases in length and comprises a nucleotide sequence having at least 90% identity to a nucleotide sequence selected from the group consisting of: SEQ ID NO:13, SEQ ID NO:1, SEQ ID NO:4, SEQ ID NO:7, SEQ ID NO:10, SEQ ID NO:16, SEQ ID NO:21, SEQ ID NO: 24, SEQ ID NO:25, SEQ ID NO:30, SEQ ID NO:31, SEQ ID NO:34, SEQ ID NO:35, SEQ ID NO:38, SEQ ID NO:39, SEQ ID NO:42, SEQ ID NO:43, SEQ ID NO:46, and SEQ ID NO: 47, and
    b) one or more second amplification primers wherein each second amplification primer is 19-30 nucleobases in length and comprising a nucleotide sequence having at least 90% identity to a nucleotide sequence selected from the group consisting of: SEQ ID NO: 14, SEQ ID NO:2, SEQ ID NO:5, SEQ ID NO:9, SEQ ID NO: 12, SEQ ID NO: 18, SEQ ID NO: 19, SEQ ID NO:22, SEQ ID NO:26, SEQ ID NO:28, SEQ ID NO:29, SEQ ID NO:32, SEQ ID NO: 33, SEQ ID NO:36, SEQ ID NO:37, SEQ ID NO:40, SEQ ID NO:41, SEQ ID NO:44, SEQ ID NO:45, SEQ ID NO:48, and SEQ ID NO:49.

2. The amplification oligonucleotides of embodiment 1 wherein
    a) the first amplification primer comprises a nucleotide sequence having 0, 1, or 2 mismatches to a nucleotide sequence selected from the group consisting of: SEQ ID NO:13, SEQ ID NO:1, SEQ ID NO:4, SEQ ID NO:7, SEQ ID NO: 10, SEQ ID NO:16, SEQ ID NO:21, SEQ ID NO:24, SEQ ID NO:25, SEQ ID NO:30, SEQ ID NO:31, SEQ ID NO:34, SEQ ID NO: 35, SEQ ID NO:38, SEQ ID NO:39, SEQ ID NO:42, SEQ ID NO:43, SEQ ID NO:46, and SEQ ID NO:47, and
    b) the second amplification primer comprises a nucleotide sequence having 0, 1, or 2 mismatches to a nucleotide sequence selected from the group consisting of: SEQ ID NO: 14, SEQ ID NO:2, SEQ ID NO:5, SEQ ID NO:9, SEQ ID NO: 12, SEQ ID NO: 18, SEQ ID NO: 19, SEQ ID NO:22, SEQ ID NO:26, SEQ ID NO:28, SEQ ID NO:29, SEQ ID NO:32, SEQ ID NO: 33, SEQ ID NO:36, SEQ ID NO:37, SEQ ID NO:40, SEQ ID NO:41, SEQ ID NO:44, SEQ ID NO:45, SEQ ID NO:48, and SEQ ID NO:49.

3. The amplification oligonucleotides of embodiment 2, wherein the first amplification primer is 90% to 100% complementary to a first BKV nucleic acid sequence and the second amplification primer is 90% to 100% complementary to a second BKV nucleic acid sequence.

4. The amplification oligonucleotides of embodiment 3, wherein the first amplification primer is >90% and <100% complementary to the first BKV nucleic acid sequence and the second amplification primer is >90% and <100% complementary to the second BKV nucleic acid sequence.

5. The amplification oligonucleotides of any one of embodiments 1-4, wherein the first amplification primer and/or the second amplification primer contains at least one modified nucleotide.

6. The amplification oligonucleotides of any one of embodiments 1-5, wherein the modified nucleotide comprises: a 2'-O-methyl modified nucleotide, a 2'-fluoro modified nucleotide, or a 5-methyl-2'-deoxycytosine.

7. The amplification oligonucleotides of embodiment 6, wherein the second amplification primer contains one or more 5-methyl-2'-deoxycytosines.

8. The amplification oligonucleotides of embodiment 7, wherein every cytosine in the second amplification primer except for a 3' terminal cytosine, if present, is a 5-methyl-2'-deoxycytosine.

9. The amplification oligonucleotides of embodiment 6, wherein the first amplification primer contains one or more 5-methyl-2'-deoxycytosine.

10. The amplification oligonucleotides of embodiment 9, wherein every cytosine in the first amplification primer except for a 3' terminal cytosine, if present, is a 5-methyl-2'-deoxycytosine.

11. The amplification oligonucleotides of any one of embodiments 1-10, wherein:
    a) the nucleotide sequence of the one or more first amplification primers consists of a nucleotide sequence selected from the group consisting of: SEQ ID NO:13, SEQ ID NO:1, SEQ ID NO:4, SEQ ID NO:7, SEQ ID NO:10, SEQ ID NO:16, SEQ ID NO:21, SEQ ID NO: 24, SEQ ID NO:25, SEQ ID NO:30, SEQ ID NO:31, SEQ ID NO:34, SEQ ID NO:35, SEQ ID NO:38, SEQ ID NO:39, SEQ ID NO:42, SEQ ID NO:43, SEQ ID NO:46, and SEQ ID NO: 47 and
    b) the nucleotide sequence the one or more second amplification primers consists of a nucleotide sequence selected from the group consisting of: SEQ ID NO:14, SEQ ID NO:2, SEQ ID NO:5, SEQ ID NO:9, SEQ ID NO: 12, SEQ ID NO: 18, SEQ ID NO: 19, SEQ ID NO: 22, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO: 45, SEQ ID NO:48, and SEQ ID NO:49.

12. The amplification oligonucleotides of any one of embodiments 1-11, wherein
   a) the first amplification primer comprises the nucleotide sequence of SEQ ID NO:13 and the second amplification primer comprises the nucleotide sequence of SEQ ID NO:14;
   b) the first amplification primer comprises the nucleotide sequence of SEQ ID NO:1 and the second amplification primer comprises the nucleotide sequence of SEQ ID NO:2;
   c) the first amplification primer comprises the nucleotide sequence of SEQ ID NO:4 and the second amplification primer comprises the nucleotide sequence of SEQ ID NO:5;
   d) the first amplification primer comprises the nucleotide sequence of SEQ ID NO:7 and the second amplification primer comprises the nucleotide sequence of SEQ ID NO:9;
   e) the first amplification primer comprises the nucleotide sequence of SEQ ID NO:10 and the second amplification primer comprises the nucleotide sequence of SEQ ID NO:12;
   f) the first amplification primer comprises the nucleotide sequence of SEQ ID NO:16 and the second amplification primer comprises the nucleotide sequence of SEQ ID NO:18;
   g) the first amplification primer comprises the nucleotide sequence of SEQ ID NO:21 and the second amplification primer comprises the nucleotide sequence of SEQ ID NO:19;
   h) the first amplification primer comprises the nucleotide sequence of SEQ ID NO:24 and the second amplification primer comprises the nucleotide sequence of SEQ ID NO:22; or
   i) the first amplification primer comprises the nucleotide sequence of SEQ ID NO:25 and the second amplification primer comprises the nucleotide sequence of SEQ ID NO:26.

13. The amplification oligonucleotides of any one of embodiments 1-12, wherein
   a) the first amplification primer comprises the nucleotide sequence of SEQ ID NO:13 and the one or more second amplification primers comprise the nucleotide sequences of SEQ ID NO: 36 and SEQ ID NO:37;
   b) the one or more first amplification primers comprise the nucleotide sequences of SEQ ID NO:35 and SEQ ID NO:36 and the second amplification primer comprises the nucleotide sequence of SEQ ID NO: 14;
   c) the one or more first amplification primers comprise the nucleotide sequences of SEQ ID NO:35 and SEQ ID NO:36 and the one or more second amplification primers comprise the nucleotide sequences of SEQ ID NO:36 and SEQ ID NO:37;
   d) the first amplification primer comprises the nucleotide sequence of SEQ ID NO:1 and the one or more second amplification primers comprise the nucleotide sequences of SEQ ID NO: 28 and SEQ ID NO:29;
   e) the first amplification primer comprises the nucleotide sequence of SEQ ID NO: 10 and the one or more second amplification primers comprise the nucleotide sequences of SEQ ID NO: 32 and SEQ ID NO:33;
   f) the one or more first amplification primers comprise the nucleotide sequences of SEQ ID NO:30 and SEQ ID NO:31 and the second amplification primer comprises the nucleotide sequence of SEQ ID NO: 12;
   g) the one or more first amplification primers comprise the nucleotide sequences of SEQ ID NO:30 and SEQ ID NO:31 and the one or more second amplification primers comprise the nucleotide sequences of SEQ ID NO:32 and SEQ ID NO:33;
   h) the one or more first amplification primers comprise the nucleotide sequences of SEQ ID NO:38 and SEQ ID NO:39 and the second amplification primer comprises the nucleotide sequence of SEQ ID NO:18;
   i) the first amplification primer comprises the nucleotide sequence of SEQ ID NO:21 and the one or more second amplification primers comprise the nucleotide sequences of SEQ ID NO: 40 and SEQ ID NO:41;
   j) the one or more first amplification primers comprise the nucleotide sequences of SEQ ID NO:42 and SEQ ID NO:43 and the second amplification primer comprises the nucleotide sequence of SEQ ID NO:19;
   k) the one or more first amplification primers comprise the nucleotide sequences of SEQ ID NO:42 and SEQ ID NO:43 and the one or more second amplification primers comprise the nucleotide sequences of SEQ ID NO:40 and SEQ ID NO:41;
   l) the first amplification primer comprises the nucleotide sequence of SEQ ID NO:24 and the one or more second amplification primers comprise the nucleotide sequences of SEQ ID NO: 44 and SEQ ID NO:45;
   m) the one or more first amplification primers comprise the nucleotide sequences of SEQ ID NO:46 and SEQ ID NO:47 and the second amplification primer comprises the nucleotide sequence of SEQ ID NO:22;
   n) the one or more first amplification primers comprise the nucleotide sequences of SEQ ID NO:46 and SEQ ID NO:47 and the one or more second amplification primers comprise the nucleotide sequences of SEQ ID NO:44 and SEQ ID NO:45; or
   o) the first amplification primer comprises the nucleotide sequence of SEQ ID NO:25 and the one or more second amplification primers comprise the nucleotide sequences of SEQ ID NO: 48 and SEQ ID NO:49.

14. A probe oligonucleotide for detecting an amplified BKV nucleic acid sequence comprising: a probe oligonucleotide 21-30 nucleobases in length and comprising a nucleotide sequence having at least 90% identity to a nucleotide sequence selected from the group consisting of: SEQ ID NO:15, SEQ ID NO:3, SEQ ID NO:6, SEQ ID NO:8, SEQ ID NO:11, SEQ ID NO:17, SEQ ID NO:20, SEQ ID NO:23, and SEQ ID NO:27.

15. The probe oligonucleotide of embodiment 14 wherein the probe oligonucleotide comprises a nucleotide sequence having 0, 1, or 2 mismatches to a nucleotide sequence selected from the group consisting of: SEQ ID NO:15, SEQ ID NO:3, SEQ ID NO:6, SEQ ID NO:8, SEQ ID NO:11, SEQ ID NO:17, SEQ ID NO:20, SEQ ID NO:23, and SEQ ID NO:27.

16. The probe oligonucleotide of embodiment 15, wherein the probe oligonucleotide is 90% to 100% complementary to a third BKV nucleic acid sequence.

17. The probe oligonucleotide of embodiment 16, wherein the probe oligonucleotide is >90% and <100% complementary to the third BKV nucleic acid sequence.

18. The probe oligonucleotide of any one of embodiments 14-17, wherein the probe oligonucleotide contains at least one modified nucleotide.

19. The probe oligonucleotide of embodiment 18, wherein the modified nucleotide comprises a 2'-O-methyl modified nucleotide, a 2'-fluoro modified nucleotide, or a 5-methyl-2'-deoxycytosine.

20. The probe oligonucleotide of embodiment 19, wherein the probe oligonucleotide contains one or more 5-methyl-2'-deoxycytosines.

21. The probe oligonucleotide of embodiment 20, wherein the probe oligonucleotide contains 2, 3, 4, 5, 6, 7 or 8 5-methyl-2'-deoxycytosines.

22. The probe oligonucleotide of embodiment 20, wherein every cytosine in the probe oligonucleotide is a 5-methyl-2'-deoxycytosine.

23. The probe oligonucleotide of any one of embodiments 14-22, wherein the nucleotide sequence of the probe oligonucleotide consists of a nucleotide sequence selected from the group consisting of: SEQ ID NO:15, SEQ ID NO:3, SEQ ID NO:6, SEQ ID NO:8, SEQ ID NO:11, SEQ ID NO: 17, SEQ ID NO:20, SEQ ID NO:23, and SEQ ID NO:27

24. The probe oligonucleotide of any one of embodiments 14-23, wherein the probe oligonucleotide comprises a detectable label.

25. The probe oligonucleotide of embodiment 24, wherein the detectable label contains a fluorescent molecule.

26. The probe oligonucleotide of embodiment 25, wherein the fluorescent molecule is attached at the 5' or 3' end of the probe oligonucleotide.

27. The probe oligonucleotide of any one of embodiments 24-26, wherein the probe oligonucleotide contains a quencher.

28. The probe oligonucleotide of embodiment 27, wherein the detectable label is attached at the 5' end of the probe oligonucleotide and the quencher is attached at the 3' end of the probe oligonucleotide.

29. The probe oligonucleotide of any one of embodiments 24-28 wherein the probe oligonucleotide is a hydrolysis probe.

30. A reaction mixture for amplifying a BKV nucleic acid sequence comprising:
   a) one or more first amplification primers wherein each first amplification primer is 20-30 nucleobases in length and comprises a nucleotide sequence having at least 90% identity to a nucleotide sequence selected from the group consisting of: SEQ ID NO:13, SEQ ID NO:1, SEQ ID NO:4, SEQ ID NO:7, SEQ ID NO:10, SEQ ID NO:16, SEQ ID NO:21, SEQ ID NO: 24, SEQ ID NO:25, SEQ ID NO:30, SEQ ID NO:31, SEQ ID NO:34, SEQ ID NO:35, SEQ ID NO:38, SEQ ID NO:39, SEQ ID NO:42, SEQ ID NO:43, SEQ ID NO:46, and SEQ ID NO: 47 and
   b) one or more second amplification primers wherein each second amplification primer is 21-30 nucleobases in length and comprising a nucleotide sequence having at least 90% identity to a nucleotide sequence selected from the group consisting of: SEQ ID NO:14, SEQ ID NO:2, SEQ ID NO:5, SEQ ID NO:9, SEQ ID NO: 12, SEQ ID NO: 18, SEQ ID NO: 19, SEQ ID NO:22, SEQ ID NO:26, SEQ ID NO:28, SEQ ID NO:29, SEQ ID NO:32, SEQ ID NO: 33, SEQ ID NO:36, SEQ ID NO:37, SEQ ID NO:40, SEQ ID NO:41, SEQ ID NO:44, SEQ ID NO:45, SEQ ID NO:48, and SEQ ID NO:49.

31. The reaction mixture of embodiment 30, wherein
   a) the first amplification primer comprises a nucleotide sequence having 0, 1, or 2 mismatches to a nucleotide sequence selected from the group consisting of: SEQ ID NO:13, SEQ ID NO:1, SEQ ID NO:4, SEQ ID NO:7, SEQ ID NO: 10, SEQ ID NO: 16, SEQ ID NO:21, SEQ ID NO:24, SEQ ID NO:25, SEQ ID NO:30, SEQ ID NO:31, SEQ ID NO:34, SEQ ID NO: 35, SEQ ID NO:38, SEQ ID NO:39, SEQ ID NO:42, SEQ ID NO:43, SEQ ID NO:46, and SEQ ID NO:47, and
   b) the second amplification primer comprises a nucleotide sequence having 0, 1, or 2 mismatches to a nucleotide sequence selected from the group consisting of: SEQ ID NO: 14, SEQ ID NO:2, SEQ ID NO:5, SEQ ID NO:9, SEQ ID NO: 12, SEQ ID NO: 18, SEQ ID NO: 19, SEQ ID NO:22, SEQ ID NO:26, SEQ ID NO:28, SEQ ID NO:29, SEQ ID NO:32, SEQ ID NO: 33, SEQ ID NO:36, SEQ ID NO:37, SEQ ID NO:40, SEQ ID NO:41, SEQ ID NO:44, SEQ ID NO:45, SEQ ID NO:48, and SEQ ID NO:49.

32. The reaction mixture of embodiment 30 or 31, wherein the first amplification primer is 90% to 100% complementary to a first BKV nucleic acid sequence and the second amplification primer is 90% to 100% complementary to a second BKV nucleic acid sequence.

33. The reaction mixture of any one of embodiments 30-32, wherein the first amplification primer is >90% and <100% complementary to the first BKV nucleic acid sequence and the second amplification primer is >90% and <100% complementary to the second BKV nucleic acid sequence.

34. The reaction mixture of any one of embodiments 30-33, wherein the first amplification primer and/or the second amplification primer contains at least one modified nucleotide.

35. The reaction mixture of embodiment 34, wherein the modified nucleotide comprises: a 2'-O-methyl modified nucleotide, a 2'-fluoro modified nucleotide, or a 5-methyl-2'-deoxycytosine.

36. The reaction mixture of embodiment 35, wherein the second amplification primer contains one or more 5-methyl 2'-deoxycytosines.

37. The reaction mixture of embodiment 36, wherein every cytosine in the second amplification primer except for a 3' terminal cytosine, if present, is a 5-methyl-2'-deoxycytosine.

38. The reaction mixture of embodiment 35, wherein the first amplification primer contains one or more 5-methyl 2' deoxycytosines.

39. The reaction mixture of embodiment 38, wherein every cytosine in the first amplification primer except for a 3' terminal cytosine, if present, is a 5-methyl-2'-deoxycytosine.

40. The reaction mixture of any one of embodiments 30-39, wherein:
   a) the nucleotide sequence of the one or more first amplification primers consists of a nucleotide sequence selected from the group consisting of: SEQ ID NO:13, SEQ ID NO:1, SEQ ID NO:4, SEQ ID NO:7, SEQ ID NO:10, SEQ ID NO:16, SEQ ID NO:21, SEQ ID NO: 24, SEQ ID NO:25, SEQ ID NO:30, SEQ ID NO:31, SEQ ID NO:34, SEQ ID NO:35, SEQ ID NO:38, SEQ ID NO:39, SEQ ID NO:42, SEQ ID NO:43, SEQ ID NO:46, and SEQ ID NO: 47, and
   b) the nucleotide sequence the one or more second amplification primers consists of a nucleotide sequence selected from the group consisting of: SEQ ID NO:14, SEQ ID NO:2, SEQ ID NO:5, SEQ ID NO:9, SEQ ID NO:12, SEQ ID NO:18, SEQ ID NO:19, SEQ ID NO: 22, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO: 45, SEQ ID NO:48, and SEQ ID NO:49.

41. The reaction mixture of any one of embodiments 30-40, wherein
   a) the first amplification primer comprises the nucleotide sequence of SEQ ID NO: 13 and the second amplification primer comprises the nucleotide sequence of SEQ ID NO:14;
   b) the first amplification primer comprises the nucleotide sequence of SEQ ID NO: 1 and the second amplification primer comprises the nucleotide sequence of SEQ ID NO:2;
   c) the first amplification primer comprises the nucleotide sequence of SEQ ID NO:4 and the second amplification primer comprises the nucleotide sequence of SEQ ID NO:5;
   d) the first amplification primer comprises the nucleotide sequence of SEQ ID NO:7 and the second amplification primer comprises the nucleotide sequence of SEQ ID NO:9;
   e) the first amplification primer comprises the nucleotide sequence of SEQ ID NO:10 and the second amplification primer comprises the nucleotide sequence of SEQ ID NO:12;
   f) the first amplification primer comprises the nucleotide sequence of SEQ ID NO:16 and the second amplification primer comprises the nucleotide sequence of SEQ ID NO:18;
   g) the first amplification primer comprises the nucleotide sequence of SEQ ID NO:21 and the second amplification primer comprises the nucleotide sequence of SEQ ID NO:19;
   h) the first amplification primer comprises the nucleotide sequence of SEQ ID NO:24 and the second amplification primer comprises the nucleotide sequence of SEQ ID NO:22; or
   i) the first amplification primer comprises the nucleotide sequence of SEQ ID NO:25 and the second amplification primer comprises the nucleotide sequence of SEQ ID NO:26.

42. The reaction mixture of any one of embodiments 30-41, wherein
   a) the first amplification primer comprises the nucleotide sequence of SEQ ID NO:13 and the one or more second amplification primers comprise the nucleotide sequences of SEQ ID NO: 36 and SEQ ID NO:37;
   b) the one or more first amplification primers comprise the nucleotide sequences of SEQ ID NO:35 and SEQ ID NO:36 and the second amplification primer comprises the nucleotide sequence of SEQ ID NO:14;
   c) the one or more first amplification primers comprise the nucleotide sequences of SEQ ID NO:35 and SEQ ID NO:36 and the one or more second amplification primers comprise the nucleotide sequences of SEQ ID NO:36 and SEQ ID NO:37;
   d) the first amplification primer comprises the nucleotide sequence of SEQ ID NO:1 and the one or more second amplification primers comprise the nucleotide sequences of SEQ ID NO: 28 and SEQ ID NO:29;
   e) the first amplification primer comprises the nucleotide sequence of SEQ ID NO:10 and the one or more second amplification primers comprise the nucleotide sequences of SEQ ID NO: 32 and SEQ ID NO:33;
   f) the one or more first amplification primers comprise the nucleotide sequences of SEQ ID NO:30 and SEQ ID NO:31 and the second amplification primer comprises the nucleotide sequence of SEQ ID NO:12;
   g) the one or more first amplification primers comprise the nucleotide sequences of SEQ ID NO:30 and SEQ ID NO:31 and the one or more second amplification primers comprise the nucleotide sequences of SEQ ID NO:32 and SEQ ID NO:33;
   h) the one or more first amplification primers comprise the nucleotide sequences of SEQ ID NO:38 and SEQ ID NO:39 and the second amplification primer comprises the nucleotide sequence of SEQ ID NO:18;
   i) the first amplification primer comprises the nucleotide sequence of SEQ ID NO:21 and the one or more second amplification primers comprise the nucleotide sequences of SEQ ID NO: 40 and SEQ ID NO:41;
   j) the one or more first amplification primers comprise the nucleotide sequences of SEQ ID NO:42 and SEQ ID NO:43 and the second amplification primer comprises the nucleotide sequence of SEQ ID NO:19;
   k) the one or more first amplification primers comprise the nucleotide sequences of SEQ ID NO:42 and SEQ ID NO:43 and the one or more second amplification primers comprise the nucleotide sequences of SEQ ID NO:40 and SEQ ID NO:41;
   l) the first amplification primer comprises the nucleotide sequence of SEQ ID NO:24 and the one or more second amplification primers comprise the nucleotide sequences of SEQ ID NO: 44 and SEQ ID NO:45;
   m) the one or more first amplification primers comprise the nucleotide sequences of SEQ ID NO:46 and SEQ ID NO:47 and the second amplification primer comprises the nucleotide sequence of SEQ ID NO:22;
   n) the one or more first amplification primers comprise the nucleotide sequences of SEQ ID NO:46 and SEQ ID NO:47 and the one or more second amplification primers comprise the nucleotide sequences of SEQ ID NO:44 and SEQ ID NO:45; or
   o) the first amplification primer comprises the nucleotide sequence of SEQ ID NO:25 and the one or more second amplification primers comprise the nucleotide sequences of SEQ ID NO: 48 and SEQ ID NO:49.

43. The reaction mixture of any one of embodiments 30-42, further comprising a probe oligonucleotide wherein the probe oligonucleotide is 21-30 nucleobases in length and comprises a nucleotide sequence having at least 90% identity to a nucleotide sequence selected from the group consisting of: SEQ ID NO: 15, SEQ ID NO:3, SEQ ID NO:6, SEQ ID NO:8, SEQ ID NO:11, SEQ ID NO:17, SEQ ID NO:20, SEQ ID NO:23, and SEQ ID NO:27.

44. The reaction mixture of embodiment 43, wherein the probe oligonucleotide comprises a nucleotide sequence having 0, 1, or 2 mismatches to a nucleotide sequence selected from the group consisting of: SEQ ID NO:15, SEQ ID NO:3, SEQ ID NO:6, SEQ ID NO:8, SEQ ID NO:11, SEQ ID NO:17, SEQ ID NO:20, SEQ ID NO:23, and SEQ ID NO:27.

45. The reaction mixture of embodiment 44, wherein the probe oligonucleotide is 90% to 100% complementary to a third BKV nucleic acid sequence.

46. The reaction mixture of embodiment 45, wherein the probe oligonucleotide is >90% and <100% complementary to the third BKV nucleic acid sequence.

47. The reaction mixture of any one of embodiments 43-46, wherein the probe oligonucleotide contains at least one modified nucleotide.

48. The reaction mixture of embodiment 47, wherein the modified nucleotide comprises a 2'-O-methyl modified nucleotide, a 2'-fluoro modified nucleotide, or a 5-methyl-2'-deoxycytosine.

49. The reaction mixture of embodiment 48, wherein the probe oligonucleotide contains one or more 5-methyl-2'-deoxycytosine.

50. The reaction mixture of embodiment 49, wherein every cytosine in the probe oligonucleotide is a 5-methyl-2'-deoxycytosine.

51. The reaction mixture of any one of embodiments 43-50, wherein the nucleotide sequence of the probe oligonucleotide consists of a nucleotide sequence selected from the group consisting of: SEQ ID NO: 15, SEQ ID NO:3, SEQ ID NO:6, SEQ ID NO:8, SEQ ID NO: 11, SEQ ID NO:17, SEQ ID NO:20, SEQ ID NO:23, and SEQ ID NO:27

52. The reaction mixture of any one of embodiments 43-51, wherein the probe oligonucleotide comprises a detectable label.

53. The reaction mixture of embodiment 52, wherein the detectable label contains a fluorescent molecule.

54. The reaction mixture of any one of embodiments 43-53 wherein the probe oligonucleotide further contains a quencher.

55. The reaction mixture of embodiment 54 wherein the detectable label is attached at the 5' end of the probe oligonucleotide and the quencher is attached at the 3' end of the probe oligonucleotide.

56. The reaction mixture of any one of embodiments 43-55 wherein the probe oligonucleotide is a hydrolysis probe.

57. A reaction mixture comprising a probe oligonucleotide wherein the probe oligonucleotide is 21-30 nucleobases in length and comprises a nucleotide sequence having at least 90% identity to a nucleotide sequence selected from the group consisting of: SEQ ID NO: 15, SEQ ID NO:3, SEQ ID NO:6, SEQ ID NO:8, SEQ ID NO:11, SEQ ID NO:17, SEQ ID NO: 20, SEQ ID NO:23, and SEQ ID NO:27.

58. The reaction mixture of embodiment 57, wherein the probe oligonucleotide comprises a nucleotide sequence having 0, 1, or 2 mismatches to a nucleotide sequence selected from the group consisting of: SEQ ID NO: 15, SEQ ID NO:3, SEQ ID NO:6, SEQ ID NO:8, SEQ ID NO:11, SEQ ID NO:17, SEQ ID NO:20, SEQ ID NO:23, and SEQ ID NO:27.

59. The reaction mixture of embodiment 57 or 58, wherein the probe oligonucleotide is 90% to 100% complementary to a third BKV nucleic acid sequence.

60. The reaction mixture of any one of embodiments 57-59, wherein the probe oligonucleotide is >90% and <100% complementary to the third BKV nucleic acid sequence.

61. The reaction mixture of any one of embodiments 57-60, wherein the probe oligonucleotide contains at least one modified nucleotide.

62. The reaction mixture of embodiment 61, wherein the modified nucleotide comprises a 2'-O-methyl modified nucleotide, a 2'-fluoro modified nucleotide, or a 5-methyl-2'-deoxycytosine.

63. The reaction mixture of embodiment 62, wherein the probe oligonucleotide contains one or more 5-methyl-2'-deoxycytosine.

64. The reaction mixture of embodiment 63, wherein every cytosine in the probe oligonucleotide is a 5-methyl-2'-deoxycytosine.

65. The reaction mixture of any one of embodiments 57-64, wherein the nucleotide sequence of the probe oligonucleotide consists of a nucleotide sequence selected from the group consisting of: SEQ ID NO:15, SEQ ID NO:3, SEQ ID NO:6, SEQ ID NO:8, SEQ ID NO: 11, SEQ ID NO:17, SEQ ID NO:20, SEQ ID NO:23, and SEQ ID NO:27

66. The reaction mixture of any one of embodiments 57-65, wherein the probe oligonucleotide comprises a detectable label.

67. The reaction mixture of embodiment 66, wherein the detectable label contains a fluorescent molecule.

68. The reaction mixture of embodiment 67 wherein the probe oligonucleotide further contains a quencher.

69. The reaction mixture of embodiment 68 wherein the detectable label is attached at the 5' end of the probe oligonucleotide and the quencher is attached at the 3' end of the probe oligonucleotide.

70. The reaction mixture of any one of embodiments 57-69, wherein the probe oligonucleotide is a hydrolysis probe.

71. A kit comprising any of the amplification oligonucleotides of any one of embodiments 1-13, any of the probe oligonucleotides of any one of embodiments 14-29, and/or any of the reaction mixtures of any one of embodiments 30-70, and instructions for use.

72. The kit of embodiment 71 further comprising one or more of: BKV positive control nucleic acid and negative control nucleic acid.

73. A method of amplifying a BKV nucleic acid sequence comprising: contacting a sample containing or suspected of containing the BKV nucleic acid sequence with the amplification oligonucleotides of any one of embodiments 1-13 and performing a nucleic acid amplification reaction.

74. The method of embodiment 73, wherein the nucleic acid amplification reaction comprises polymerase chain reaction (PCR).

75. A method of detecting a BKV nucleic acid sequence comprising: contacting a sample containing or suspected of containing the BKV nucleic acid sequence with the probe oligonucleotide of any one of embodiments 24-29 and detecting a signal from the probe oligonucleotide.

76. A method of detecting a BKV comprising: contacting a sample containing or suspected of containing a BKV with the amplification oligonucleotides of any one of embodiments 1-13 and a probe oligonucleotide of any one of embodiments 14-29 and performing a nucleic acid amplification reaction.

77. The method of embodiment 76, wherein the nucleic acid amplification reaction comprises PCR.

78. The method of embodiment 76 or 77, wherein the probe oligonucleotide is used to detect the presence or absence of an amplified BKV amplicon.

79. The method of embodiment 78, wherein detecting the presence or absence of an amplified BKV amplicon comprises quantitative PCR.

80. The method of embodiment 79, wherein the quantitative PCT is analyzed in real time.

81. The method of embodiment 80, wherein the quantitative PCR comprises TAQMAN™ (hydrolysis probe) PCR.

82. The reaction mixture of any one of embodiments 30-70 wherein the reaction mixture further contains one or more of: DNA polymerase, deoxyribonucleotides, positive control nucleic acid, negative control nucleic acid, internal control nucleic acid, KCl, MgCl2, potassium acetate, buffer, BSA, sucrose, trehalose, DMSO, betaine, formamide, glycerol, polyethylene glycol, non-ionic detergents, ammonium ions, EDTA, control amplification oligonucleotides.

EXAMPLES

Example 1. BKV Amplification and Detection

Various Concentration Combinations of salts and oligomers for BKV were evaluated to determine suitable conditions amplification. PPR (primer probe containing recon buffer) mixes were made by mixing amplification primers, probe oligonucleotides, KCl, and MgCl$_2$ mixes. The following mixes were made to be used for BKV amplification and detection.

TABLE 1-1

Oligonucleotides and MgCl$_2$ in Reaction (PPR) Mixes.

| Factors | Low (L) | Level Medium (M) | High (H) |
|---|---|---|---|
| Amplification primer conc. (μM) | 0.4 | 0.7 | 1 |
| Probe oligonucleotide conc. (μM) | 0.2 | 0.5 | 0.8 |
| MgCl$_2$ | 2 | 4 | 6 |
| MgCl$_2$ conc. (mM) in PCRT from PPR mixes | 1.92 | 3.92 | 5.92 |

TABLE 1-2

KCl and Tris in PPR Mixes.

| Factors | [initial] | units | [final] | conc. in recon. (1.25×) | 1× (μL) | 216.0 |
|---|---|---|---|---|---|---|
| KCl | 2000 | mM | 65 | 81.25 | 1.86 | 402.2 |
| Tris, pH 8.0 | 1000 | mM | 5 | 6.25 | 0.29 | 61.9 |
| Water | | | | | 26.68 | 5763.9 |
| Total Component Volume | | | | | 28.83 | 6228.0 |
| Total PPR Volume per reaction | | | | | 45.83 | |

TABLE 1-3

Final PPR Mixes, volumes per component.

| | μL |
|---|---|
| KCl/Tris Mix | 28.83 |
| Amplification primers Mix | 10 |
| Probe oligonucleotide Mix | 5 |
| MgCl$_2$ Mix | 2 |

TABLE 1-5

Amplification Primer Mixes

| | L | M | H |
|---|---|---|---|
| Concentration of amplification primer (μM) | 0.4 | 0.7 | 1 |
| 1.25× concentration of amplification primer (μM) | 0.5 | 0.875 | 1.25 |
| # of conditions (PPR) with that primer conc. | 4 | 5 | 4 |
| # of reps needed | 48 | 84 | 48 |
| Overage Factor | 1.2 | 1.2 | 1.2 |
| reps needed* overage | 57.6 | 101 | 57.6 |
| Total reps needed (Rounded Number of Reps) | 58 | 101 | 58 |
| Volume of PPR per test (μL) | 45.83 | 45.83 | 45.83 |
| Volume of Component (μL) | 10 | 10 | 10 |
| Total Volume Needed (μL) | 580 | 1010 | 580 |

TABLE 1-6

Amplification primers mix

| SEQ ID NO. | stock conc. (μM) | L Volume (μL) | M Volume (μL) | H Volume (μL) | Total Needed (μL) |
|---|---|---|---|---|---|
| 13 | 136.70 | 9.72 | 29.63 | 24.31 | 63.66 |
| 14 | 191.07 | 6.96 | 21.20 | 17.39 | 45.54 |
| 53 | 223.29 | 5.95 | 18.14 | 14.88 | 38.97 |

TABLE 1-4

PPR Final Mixes.

| PPR# | Mixes (Pri/Pro/Mg) | # reps per PPR | H | M | L | H | M | L | H | M | L | KCl/Tris Mix | Total μL in PPR tube | Vol per test PCR (μL) |
|---|---|---|---|---|---|---|---|---|---|---|---|---|---|---|
| PPR01 | HHM | 12 | 120 | | | 60 | | | | 24 | | 346.0 | 550 | 45.83 |
| PPR02 | HML | 12 | 120 | | | | 60 | | | | 24 | 346.0 | 550 | 45.83 |
| PPR03 | HLM | 12 | 120 | | | | | 60 | | 24 | | 346.0 | 550 | 45.83 |
| PPR04 | LHM | 12 | | | 120 | 60 | | | | 24 | | 346.0 | 550 | 45.83 |
| PPR05 | HMH | 12 | 120 | | | | 60 | | 24 | | | 346.0 | 550 | 45.83 |
| PPR06 | MLL | 12 | | 120 | | | | 60 | | | 24 | 346.0 | 550 | 45.83 |
| PPR07 | LML | 12 | | | 120 | | 60 | | | | 24 | 346.0 | 550 | 45.83 |
| PPR08 | LLM | 12 | | | 120 | | | 60 | | 24 | | 346.0 | 550 | 45.83 |
| PPR09 | MHL | 12 | | 120 | | 60 | | | | | 24 | 346.0 | 550 | 45.83 |
| PPR10 | MLH | 12 | | 120 | | | | 60 | 24 | | | 346.0 | 550 | 45.83 |
| PPR11 | LMH | 12 | | | 120 | | 60 | | 24 | | | 346.0 | 550 | 45.83 |
| PPR12 | MHH | 12 | | 120 | | 60 | | | 24 | | | 346.0 | 550 | 45.83 |
| PPR13 | MMM | 36 | | 360 | | | 180 | | | 72 | | 1038.0 | 1650 | 45.83 |

Pri = amplification primer,
Pro = probe oligonucleotide,
Mg = MgCl$_2$

TABLE 1-6-continued

Amplification primers mix

| SEQ ID NO. | stock conc. (µM) | L Volume (µL) | M Volume (µL) | H Volume (µL) | Total Needed (µL) |
|---|---|---|---|---|---|
| 54 | 254.55 | 5.22 | 15.91 | 13.05 | 34.19 |
|  | water | 552.15 | 925.12 | 510.37 | 1987.64 |
| Total volume needed (µL) |  | 580.00 | 1010.00 | 580.00 |  |

TABLE 1-7

Probe oligonucleotide Mix

| SEQ ID NO. | stock conc. (µM) | L Volume (µL) | M Volume (µL) | H Volume (µL) | Total Needed (µL) |
|---|---|---|---|---|---|
| 15 | 125.82 | 5.28 | 22.99 | 21.13 | 49.40 |
| 55 | 130.81 | 5.08 | 22.12 | 20.32 | 47.52 |
|  | water | 279.64 | 459.89 | 248.55 | 988.08 |
| total vol. needed (µL) |  | 290 | 505 | 290 |  |

TABLE 1-8

Mg Mixes.

|  | L | M | H |
|---|---|---|---|
| $MgCl_2$ conc. final in PCR (mM) | 2 | 4 | 6 |
| Concentration of $MgCl_2$ (mM) in PCR from PPR | 1.92 | 3.92 | 5.92 |
| 1.25X concentration of $MgCl_2$ (mM) | 2.4 | 4.9 | 7.4 |
| # of conditions (PPR) with that primer conc. | 4 | 5 | 4 |
| # of reps needed | 48 | 84 | 48 |
| Overage Factor | 1.2 | 1.2 | 1.2 |
| # of reps needed* overage | 57.6 | 100.8 | 57.6 |
| Total reps needed (Rounded Number of Reps) | 58 | 101 | 58 |
| Volume of PPR per test (µL) | 45.83 | 45.83 | 45.83 |
| Volume of Component (µL) | 2 | 2 | 2 |
| Total Volume Needed (µL) | 116 | 202 | 116 |

TABLE 1-9

Mg Mixes.

| Concentration (mM) | L Volume (µL) | M Volume (µL) | H Volume (µL) |
|---|---|---|---|
| $MgCl_2$ mixes | 1000.0 | 6.4 | 22.7 | 19.7 |
| Water |  | 109.6 | 179.3 | 96.3 |
| Total volume needed (µL) |  | 116 | 202 | 116 |

TABLE 1-10A

BKV plasmid Preparation, Initial Dilution

| Stock conc. (cp/µL) | Final conc. (cp/µL) | Stock vol. (µL) | STM (µL) | Final vol. need (µL) |
|---|---|---|---|---|
| $1.00 \times 10^6$ | $1.00 \times 10^4$ | 10.0 | 990.0 | 1000 |
| $1.00 \times 10^4$ | $1.00 \times 10^2$ | 120.0 | 11880.0 | 12000 |

TABLE 1-10B

BKV plasmid was diluted to 1000 cp/rxn to be tested with PPR mixes.

| start conc. (cp/µL) | Testing amount (cp) per 5 µL rxn | cp/µL in sample tube | Starting volume (µL) | STM (µL) | Final vol. (µL) |
|---|---|---|---|---|---|
| 100.00 | 1000 | 27.78 | 10555.6 | 27444.4 | 38000 |

TABLE 1-11

Oligonucleotide descriptions.

| SEQ ID NO: | Sequence 5' → 3' | modifications |
|---|---|---|
| 13 | CCCTACTTGAGCCAARGAACTAA |  |
| 14 | GGCCTAACWCCTCAAACATATGC | 7 5-Me-dC |
| 15 | TTAAAGCAGCAAACCCAGCAATAGCC | 7 5-Me-dC, 5' CalRed610, 3' BHQ2 |
| 53 | ATGGTCAATTAGAGACAAAG | None |
| 54 | CGTTCACTATTGGTCTCTGC | None |
| 55 | CGGAATCACAAGTCAATCATCGCGCA | 5' Q705, 3' BHQ2 |

TABLE 1-12A

Results, ROX channel

| Condition | POS | AVG Ct | SD Ct | AVG RFU | SD RFU | AVG Bckgrd | SD Bckgrd | AVG Tslope | SD Tslope | Signal:noise |
|---|---|---|---|---|---|---|---|---|---|---|
| HHM | 12 | 29.07 | 0.13 | 21048.87 | 791.23 | 2320.58 | 129.70 | 302.49 | 67.52 | 9.07 |
| HML | 12 | 29.41 | 0.09 | 14388.70 | 1062.23 | 2846.54 | 190.24 | 299.00 | 19.14 | 5.05 |
| HLM | 12 | 30.11 | 0.10 | 7006.31 | 452.79 | 683.07 | 45.33 | 353.62 | 41.05 | 10.26 |
| LHM | 12 | 29.19 | 0.22 | 13956.79 | 881.57 | 2623.40 | 210.03 | 278.70 | 42.20 | 5.32 |
| HMH | 12 | 29.51 | 0.13 | 15207.90 | 1185.05 | 1059.25 | 76.65 | 289.16 | 20.22 | 14.36 |
| MLL | 12 | 30.20 | 0.09 | 6469.95 | 306.83 | 1197.30 | 65.43 | 359.57 | 23.44 | 5.40 |
| LML | 12 | 29.63 | 0.12 | 10301.24 | 501.89 | 2854.22 | 238.95 | 261.96 | 18.94 | 3.61 |
| LLM | 12 | 30.05 | 0.09 | 6560.78 | 321.18 | 707.04 | 57.56 | 296.27 | 66.62 | 9.28 |
| MHL | 12 | 29.10 | 0.17 | 18695.12 | 996.97 | 4671.39 | 227.75 | 311.36 | 57.92 | 4.00 |

TABLE 1-12A-continued

Results, ROX channel

| Condition | POS | AVG Ct | SD Ct | AVG RFU | SD RFU | AVG Bckgrd | SD Bckgrd | AVG Tslope | SD Tslope | Signal:noise |
|---|---|---|---|---|---|---|---|---|---|---|
| MLH | 12 | 30.08 | 0.11 | 6511.82 | 536.14 | 472.87 | 40.83 | 316.25 | 53.34 | 13.77 |
| LMH | 12 | 29.43 | 0.10 | 11323.18 | 673.93 | 1111.18 | 97.62 | 286.10 | 17.45 | 10.19 |
| MHH | 12 | 29.30 | 0.14 | 16429.40 | 1203.24 | 1594.82 | 99.97 | 315.17 | 17.62 | 10.30 |
| LLL | 36 | 29.36 | 0.13 | 16177.20 | 1153.58 | 1751.66 | 115.79 | 317.60 | 28.27 | 9.24 |

TABLE 1.12A

Results, Red667 channel

| Condition | POS | AVG Ct | SD Ct | AVG RFU | SD RFU | AVG Bckgrd | SD Bckgrd | AVG Tslope | SD Tslope | Signal:noise |
|---|---|---|---|---|---|---|---|---|---|---|
| HHM | 12 | 26.82 | 0.24 | 19472.37 | 3509.94 | 7484.93 | 1419.10 | 348.94 | 83.78 | 2.60 |
| HML | 12 | 27.49 | 0.14 | 7250.95 | 593.47 | 7037.47 | 452.16 | 322.77 | 24.99 | 1.03 |
| HLM | 12 | 27.39 | 0.17 | 5407.57 | 793.76 | 1970.84 | 289.36 | 320.31 | 27.85 | 2.74 |
| LHM | 12 | 26.78 | 0.14 | 14514.50 | 906.14 | 9386.14 | 804.22 | 298.87 | 53.92 | 15.5 |
| HMH | 12 | 26.63 | 0.09 | 17266.52 | 1063.80 | 4367.43 | 237.61 | 303.16 | 15.49 | 3.95 |
| MLL | 12 | 27.66 | 0.29 | 4363.82 | 843.30 | 3366.98 | 663.78 | 313.24 | 48.36 | 1.30 |
| LML | 12 | 28.90 | 0.50 | 6083.03 | 342.20 | 7081.89 | 538.62 | 289.50 | 38.72 | 0.86 |
| LLM | 12 | 27.34 | 0.14 | 5474.85 | 669.99 | 2016.46 | 267.73 | 317.24 | 25.57 | 2.72 |
| MHL | 12 | 27.28 | 0.10 | 12119.97 | 744.14 | 14859.62 | 750.66 | 389.98 | 29.57 | 0.82 |
| MLH | 12 | 26.91 | 0.11 | 7096.06 | 655.91 | 1896.94 | 142.79 | 279.78 | 53.24 | 3.74 |
| LMH | 12 | 26.89 | 0.25 | 11437.30 | 2050.26 | 3801.42 | 744.37 | 332.56 | 54.46 | 3.01 |
| MHH | 12 | 27.11 | 0.13 | 15299.03 | 601.51 | 4725.17 | 237.46 | 383.95 | 44.03 | 3.24 |
| LLL | 36 | 26.75 | 0.25 | 16413.01 | 2313.01 | 6133.99 | 813.54 | 347.35 | 53.18 | 2.68 |

Conclusion

The BKV amplification primes/probe oligonucleotides showed robustness in Ct and RFU response over a wide range of prime, probe oligonucleotide, and MgCl$_2$ concentrations. While effective over a range of concentrations tested, 0.6 µM amplification primers, 0.4 µM probe oligonucleotide, and 4 mM MgCl$_2$ was used for most subsequent testing. The Cts are consistent across all conditions tested and across a wide range of MgCl$_2$ concentrations. The baseline fluorescence and final RFU was affected by probe oligonucleotide concentration as to be expected.

Example 2. BKV Amplification/Detection Oligonucleotide Screen

BVK oligonucleotides in various combinations were evaluated for amplification and detection of BKV. BK virus or plasmid was spiked into STM at the various concentrations. BK PPR mixes incorporating several combinations of oligonucleotides were evaluated.

TABLE 2-1

PPR mixes.

| PPR mixes | Amplification Primer SEQ ID NO. | | Probe oligonucleotide SEQ ID NO. | BK Clone Used |
|---|---|---|---|---|
| | First | Second | | |
| 1 | 1 | 2 | 3 | BK Clone 2 |
| 2 | 4 | 5 | 6 | BK Clone 1 (6) |
| 3 | 7 | 9 | 8 | BK Clone 1 |
| 4 | 10 | 12 | 11 | BK Clone 6 (1) |

TABLE 2-1-continued

PPR mixes.

| PPR mixes | Amplification Primer SEQ ID NO. | | Probe oligonucleotide SEQ ID NO. | BK Clone Used |
|---|---|---|---|---|
| | First | Second | | |
| 5 | 13 | 14 | 15 | BK Clone 6 (1) |
| 6 | 16 | 18 | 17 | BK Clone 2 (6) |
| 7 | 21 | 19 | 20 | BK Clone 6 (1) |
| 8 | 24 | 22 | 23 | BK Clone 6 (1) |
| 9 | 25 | 26 | 27 | BK Clone 5 |

TABLE 2-2

Samples processed per PPR mix.

| Sample | Sample Description | #Ext | #PCR reps per ext. | Final n |
|---|---|---|---|---|
| BK Clones | BK Clones (100000 cp/rxn) in STM | 2 | 3.1 | 4 |
| Neg Ctrl | STM | 1 | 2 | 2 |

Total reps per PPR 6

Plasmid Dilutions:

TABLE 2-3

BK Plasmid dilutions, clones 1 and 6.

Step 1. Initial Dilution

| Stock conc. (cp/mL) | Final conc. (cp/mL) | Stock vol (µL) | STM (µL) | Final vol needed (µL) |
|---|---|---|---|---|
| $1.00 \times 10^9$ | $1.00 \times 10^8$ | 20.0 | 180.0 | 200 |
| $1.00 \times 10^8$ | $1.00 \times 10^7$ | 40.0 | 360.0 | 400 |

Step 2. Rotavirus in STM, Concentration Needed (Calculation)

| Start conc. (cp/mL) | Testing amount (cp) per 5 µL rxn | cp/mL in "sample" tube | Start vol (µL) | STM (µL) | Final vol (µL) |
|---|---|---|---|---|---|
| $1.00 \times 10^7$ | 10000 | 277777.78 | 222.2 | 7777.8 | 8000 |

TABLE 2-4

BK Plasmid dilutions, clones 2 and 5.

Step 1. Initial Dilution

| Stock conc. (cp/mL) | Final conc. (cp/mL) | Stock vol (µL) | STM (µL) | Final vol needed (µL) |
|---|---|---|---|---|
| $1.00 \times 10^9$ | $1.00 \times 10^8$ | 20.0 | 180.0 | 200 |
| $1.00 \times 10^8$ | $1.00 \times 10^7$ | 20.0 | 180.0 | 200 |

Step 2. Rotavirus in STM, Concentration Needed (Calculation)

| Start conc. (cp/mL) | Testing amount (cp) per 5 µL rxn | cp/mL in "sample" tube | Start vol (µL) | STM (µL) | Final vol (µL) |
|---|---|---|---|---|---|
| $1.00 \times 10^7$ | 10000 | 277777.78 | 111.1 | 3888.9 | 4000 |
| $1.00 \times 10^5$ | 100 | 2777.78 | 111.1 | 3888.9 | 4000 |

PCR Mixes:

TABLE 2-5

Internal control (IC) Oligo Mix

| SEQ ID NO. | Units | Stock Conc. | Final Conc. | ×1.25 | µL |
|---|---|---|---|---|---|
| 53 | µM | 177.50 | 0.60 | 0.75 | 2.11 |
| 54 | µM | 254.60 | 0.60 | 0.75 | 1.47 |
| 55 | µM | 113.80 | 0.40 | 0.50 | 2.20 |
| | | | | Total: | 500.00 |

Total volume per PPR 400 µl should be 425 µL; PPR mixes slightly off for concentration

TABLE 2-6

VP1 PPR Mix

| Reagent | Units | Stock Conc. | Final Conc. | ×1.25 | µL |
|---|---|---|---|---|---|
| SEQ ID NO: 1 | µM | 143.53 | 0.60 | 0.75 | 2.09 |
| SEQ ID NO: 2 | µM | 175.10 | 0.60 | 0.75 | 1.71 |
| SEQ ID NO: 3 | µM | 83.38 | 0.40 | 0.50 | 2.40 |
| IC Oligo Mix | x | 1.00 | 1.00 | 1.00 | 4.92 |
| $MgCl_2$ | mM | 1000.00 | 4.00 | 5.00 | 2.00 |
| KCl | mM | 2000.00 | 65.00 | 81.25 | 16.25 |
| Water | | | | | 395.63 |
| Total | | | | | 425.00 |

TABLE 2-7

VP2-1 PPR Mix

| Reagent | Units | Stock Conc. | Final Conc. | ×1.25 | µL |
|---|---|---|---|---|---|
| SEQ ID NO: 4 | µM | 193.80 | 0.60 | 0.75 | 1.55 |
| SEQ ID NO: 5 | µM | 171.58 | 0.60 | 0.75 | 1.75 |
| SEQ ID NO: 6 | µM | | 0.40 | 0.50 | 5.72 |
| IC Oligo Mix | x | 1.00 | 1.00 | 1.00 | 4.92 |
| $MgCl_2$ | mM | 1000.00 | 4.00 | 5.00 | 2.00 |
| KCl | mM | 2000.00 | 65.00 | 81.25 | 16.25 |
| Water | | | | | 392.82 |
| Total | | | | | 425.00 |

TABLE 2-8

VP2-2 PPR Mix

| Reagent | Units | Stock Conc. | Final Conc. | ×1.25 | µL |
|---|---|---|---|---|---|
| SEQ ID NO: 7 | µM | 147.44 | 0.60 | 0.75 | 2.03 |
| SEQ ID NO: 8 | µM | 71.48 | 0.60 | 0.75 | 4.20 |
| SEQ ID NO: 9 | µM | 158.44 | 0.40 | 0.50 | 1.26 |
| IC Oligo Mix | x | 1.00 | 1.00 | 1.00 | 4.92 |
| $MgCl_2$ | mM | 1000.00 | 4.00 | 5.00 | 2.00 |
| KCl | mM | 2000.00 | 65.00 | 81.25 | 16.25 |
| Water | | | | | 394.34 |
| Total | | | | | 425.00 |

TABLE 2-9

VP2-3 PPR Mix

| Reagent | Units | Stock Conc. | Final Conc. | ×1.25 | µL |
|---|---|---|---|---|---|
| SEQ ID NO: 10 | µM | 157.34 | 0.60 | 0.75 | 1.91 |
| SEQ ID NO: 11 | µM | 59.24 | 0.60 | 0.75 | 5.06 |
| SEQ ID NO: 12 | µM | 148.55 | 0.40 | 0.50 | 1.35 |
| IC Oligo Mix | x | 1.00 | 1.00 | 1.00 | 4.92 |
| $MgCl_2$ | mM | 1000.00 | 4.00 | 5.00 | 2.00 |
| KCl | mM | 2000.00 | 65.00 | 81.25 | 16.25 |
| Water | | | | | 393.52 |
| Total | | | | | 425.00 |

TABLE 2-10

VP2-4 PPR Mix

| Reagent | Units | Stock Conc. | Final Conc. | ×1.25 | µL |
|---|---|---|---|---|---|
| SEQ ID NO: 13 | µM | 139.70 | 0.60 | 0.75 | 2.19 |
| SEQ ID NO: 15 | µM | 125.82 | 0.60 | 0.75 | 2.38 |
| SEQ ID NO: 14 | µM | 191.07 | 0.40 | 0.50 | 1.05 |

TABLE 2-10-continued

VP2-4 PPR Mix

| Reagent | Units | Stock Conc. | Final Conc. | ×1.25 | μL |
|---|---|---|---|---|---|
| IC Oligo Mix | x | 1.00 | 1.00 | 1.00 | 4.92 |
| MgCl$_2$ | mM | 1000.00 | 4.00 | 5.00 | 2.00 |
| KCl | mM | 2000.00 | 65.00 | 81.25 | 16.25 |
| Water | | | | | 396.21 |
| Total | | | | | 425.00 |

TABLE 2-11

VP2-5 PPR Mix

| Reagent | Units | Stock Conc. | Final Conc. | ×1.25 | μL |
|---|---|---|---|---|---|
| SEQ ID NO: 16 | μM | 180.35 | 0.60 | 0.75 | 1.66 |
| SEQ ID NO: 17 | μM | 91.65 | 0.60 | 0.75 | 3.27 |
| SEQ ID NO: 18 | μM | 170.07 | 0.40 | 0.50 | 1.18 |
| IC Oligo Mix | x | 1.00 | 1.00 | 1.00 | 4.92 |
| MgCl$_2$ | mM | 1000.00 | 4.00 | 5.00 | 2.00 |
| KCl | mM | 2000.00 | 65.00 | 81.25 | 16.25 |
| Water | | | | | 395.72 |
| Total | | | | | 425.00 |

TABLE 2-12

VP2-6 PPR Mix

| Reagent | Units | Stock Conc. | Final Conc. | ×1.25 | μL |
|---|---|---|---|---|---|
| SEQ ID NO: 19 | μM | 163.04 | 0.60 | 0.75 | 1.84 |
| SEQ ID NO: 20 | μM | 64.90 | 0.60 | 0.75 | 4.62 |
| SEQ ID NO: 21 | μM | 160.88 | 0.40 | 0.50 | 1.24 |
| IC Oligo Mix | x | 1.00 | 1.00 | 1.00 | 4.92 |
| MgCl$_2$ | mM | 1000.00 | 4.00 | 5.00 | 2.00 |
| KCl | mM | 2000.00 | 65.00 | 81.25 | 16.25 |
| Water | | | | | 394.13 |
| Total | | | | | 425.00 |

TABLE 2-13

VP2-7 PPR Mix

| Reagent | Units | Stock Conc. | Final Conc. | ×1.25 | μL |
|---|---|---|---|---|---|
| SEQ ID NO: 22 | μM | 170.91 | 0.60 | 0.75 | 1.76 |
| SEQ ID NO: 23 | μM | 110.52 | 0.60 | 0.75 | 2.71 |
| SEQ ID NO: 24 | μM | 223.08 | 0.40 | 0.50 | 0.90 |
| IC Oligo Mix | x | 1.00 | 1.00 | 1.00 | 4.92 |
| MgCl$_2$ | mM | 1000.00 | 4.00 | 5.00 | 2.00 |
| KCl | mM | 2000.00 | 65.00 | 81.25 | 16.25 |
| Water | | | | | 396.47 |
| Total | | | | | 425.00 |

TABLE 2-14

LT PPR Mix

| Reagent | Units | Stock Conc. | Final Conc. | ×1.25 | μL |
|---|---|---|---|---|---|
| SEQ ID NO: 25 | μM | 167.3 | 0.60 | 0.75 | 1.79 |
| SEQ ID NO: 26 | μM | 160.35 | 0.60 | 0.75 | 1.87 |
| SEQ ID NO: 27 | μM | 85.37 | 0.40 | 0.50 | 2.34 |
| IC Oligo Mix | x | 1.00 | 1.00 | 1.00 | 4.92 |
| MgCl$_2$ | mM | 1000.00 | 4.00 | 5.00 | 2.00 |
| KCl | mM | 2000.00 | 65.00 | 81.25 | 16.25 |
| Water | | | | | 395.83 |
| Total | | | | | 425.00 |

TABLE 2-15

Oligo info-description.

| SEQ ID NO. | Sequence 5' → 3' | Modifications | OD | Conc. (μM) |
|---|---|---|---|---|
| 1 | CTAGAACTTCTACTCCTCCTTTTATTA | 7 5-Me-dCs | 29.5 | 143.53 |
| 2 | GGCCCCAACMAAAAGAAAAGG | 5 5-Me-dCs | 28.6 | 175.10 |
| 3 | GGCTTTTTGGGAGCTGCCCCTGGA | 5' CalRed610, 3' BHQ2 | 17.9 | 83.38 |
| 4 | GCAGCAAACCCAGCAATAGC | | 29.5 | 193.80 |
| 5 | CCTTGCTACTGTAGAGGGCATAAC | 6 5-Me-dCs | 31.9 | 171.58 |
| 6 | AGCACCAGCAATTACAGCATATGTTGAGG | 6 5-Me-dCs, 5' CalRed610, 3' BHQ2 | 9.2 | 34.99 |
| 7 | GACTCTGTAAAAGACTCCTAGGTAAG | | 29.5 | 147.44 |
| 8 | ATGGGTGCTGCTCTAGCACTTTTGGG | 5 5-Me-dCs, 5' CalRed610, 3' BHQ2 | 16.6 | 71.48 |

TABLE 2-15-continued

Oligo info-description.

| SEQ ID NO. | Sequence 5' → 3' | Modifications | OD | Conc. (µM) |
|---|---|---|---|---|
| 9 | GCAGCAGCCTCAGATACACTGGC | | 27.8 | 158.44 |
| 10 | TTAGTTCYTTGGCTCAAGTAGGG | | 27.9 | 157.34 |
| 11 | ATTGGGATCACAAAGTTTCCACTGTAGGC | 6 5-Me-dCs, 5' CalRed610, 3' BHQ2 | 15.1 | 59.24 |
| 12 | GGGTTAAACAATTCCAAWGCCATGCC | | 29.5 | 148.55 |
| 13 | CCCTACTTGAGCCAARGAACTAA | | 23.9 | 136.70 |
| 15 | TTAAAGCAGCAAACCCAGCAATAGCC | 7 5-Me-dCs, 5' CalRed610, 3' BHQ2 | 29 | 125.82 |
| 14 | GGCCTAACWCCTCAAACATATGC | 7 5-Me-dCs | 33.7 | 191.07 |
| 16 | CCTTTTCTTTTKGTTGGGGC | | 27.5 | 180.35 |
| 17 | ACAGTCCCGTACAGGCCTAGAAG | 7 5-Me-dCs, 5' CalRed610, 3' BHQ2 | 19.1 | 91.65 |
| 18 | AAAACTATTGCCCCAGGAGGTGCT | | 31.3 | 170.07 |
| 19 | TTAGTTCYTTGGCTCAAGTAGGGTA | 3 5-Me-dCs, | 31.6 | 163.04 |
| 20 | GCCTACAGTGGAAACTTTGTGATCCCAAT | 7 5-Me-dCs, 5' CalRed610, 3' BHQ2 | 16.5 | 64.90 |
| 21 | GGGTTAAACAATTCCAAWGCCAT | | 28.3 | 160.88 |
| 22 | CCCTACTTGAGCCAARGAACTAA | 7 5-Me-dC | 30.3 | 170.91 |
| 23 | GGCTATTGCTGGGTTTGCTGCTTTAA | 4 5-Me-dCs, 5' CalRed610, 3' BHQ2 | 25.6 | 110.52 |
| 24 | GGCCTAACWCCTCAAACATATGC | | 38.8 | 223.08 |
| 25 | GAAAGAGCTGCCTGGGGAAA | | 26.1 | 167.3 |
| 26 | CTACCTTTACATCYTGCTCCATTT | 8 5-Me-dCs, | 29.2 | 160.35 |
| 27 | CCCTGACAAAGGGGCGACGAGGATAAAA | 5' CalRed610, 3' BHQ2 | 21.8 | 85.37 |

TABLE 2-16

Results.

| Channel | Target | Pos | AVG Ct | SD Ct | AVG RFU | SD RFU | AVG Bckgrd | SD Bckgrd | AVG Tslope | SD Tslope | Signal:Noise | Amplicon Size |
|---|---|---|---|---|---|---|---|---|---|---|---|---|
| ROX | VP1 | 4/4 | 27.72 | 0.13 | 4481.96 | 159.12 | 263.51 | 8.79 | 245.89 | 12.34 | 17.01 | 106 |
| ROX | VP2-1 | 4/4 | 27.42 | 0.12 | 7128.10 | 443.31 | 2078.57 | 117.74 | 261.37 | 13.67 | 3.43 | 117 |
| ROX | VP2-2 | 4/4 | 26.08 | 0.10 | 10570.21 | 464.21 | 588.37 | 18.31 | 279.84 | 62.12 | 17.97 | 115 |
| ROX | VP2-3 | 4/4 | 26.26 | 0.09 | 12420.68 | 676.59 | 2423.59 | 198.64 | 303.37 | 24.09 | 5.12 | 109 |
| ROX | VP2-4 | 4/4 | 26.34 | 0.07 | 9733.29 | 431.71 | 1537.83 | 67.03 | 281.49 | 8.59 | 6.33 | 111 |
| ROX | VP2-5 | 4/4 | 26.65 | 0.12 | 8645.25 | 628.92 | 636.67 | 40.83 | 229.77 | 12.82 | 13.58 | 132 |
| ROX | VP2-6 | 4/4 | 26.61 | 0.21 | 10480.48 | 517.12 | 1459.78 | 55.63 | 253.74 | 27.52 | 7.18 | 109 |
| ROX | VP2-7 | 4/4 | 26.90 | 0.12 | 9141.11 | 597.74 | 1163.53 | 103.44 | 244.36 | 55.06 | 7.86 | 111 |
| | Large T | 2/2 | 26.93 | 0.11 | 7352.34 | 270.85 | 963.34 | 69.99 | 293.09 | 87.18 | 7.63 | |
| RED677 | VP1 | 4/4 | 27.44 | 0.11 | 4259.03 | 420.00 | 1829.29 | 166.05 | 314.58 | 23.08 | 2.33 | |
| RED677 | VP2-1 | 4/4 | 27.07 | 0.03 | 6046.08 | 555.43 | 2487.54 | 173.28 | 425.23 | 22.02 | 2.43 | |
| RED677 | VP2-2 | 4/4 | 27.07 | 0.03 | 6611.05 | 161.20 | 2522.22 | 58.50 | 414.97 | 12.73 | 2.62 | |
| RED677 | VP2-3 | 4/4 | 27.83 | 0.39 | 3749.60 | 860.11 | 1644.92 | 372.31 | 295.18 | 25.28 | 2.28 | |
| RED677 | VP2-4 | 4/4 | 27.85 | 0.12 | 3579.26 | 172.71 | 1548.29 | 76.69 | 286.01 | 54.56 | 2.31 | |

TABLE 2-16-continued

Results.

| Channel | Target | Pos | AVG Ct | SD Ct | AVG RFU | SD RFU | AVG Bckgrd | SD Bckgrd | AVG Tslope | SD Tslope | Signal:Noise | Amplicon Size |
|---|---|---|---|---|---|---|---|---|---|---|---|---|
| RED677 | VP2-5 | 4/4 | 27.82 | 0.04 | 3437.52 | 155.84 | 1450.19 | 66.80 | 252.31 | 7.34 | 2.37 | |
| RED677 | VP2-6 | 4/4 | 27.52 | 0.15 | 5254.34 | 224.51 | 2051.39 | 42.89 | 304.07 | 22.45 | 2.56 | |
| RED677 | VP2-7 | 4/4 | 28.84 | 0.18 | 1530.25 | 177.66 | 763.74 | 82.90 | 218.17 | 17.91 | 2.00 | |
| | Large T | 4/4 | 26.60 | 0.01 | 9414.63 | 616.55 | 3393.78 | 285.66 | 304.70 | 2.97 | 2.77 | |

Conclusion: All amplification primer/probe oligonucleotide designs amplified and detected the BKV plasmids tested. 100% detection was seen for BK virus and plasmid in STM at all concentrations tested down to 10 copies/reaction (cpr). PCR efficiency was high with R2 values >0.99 and slopes at −3.4 or −3.5 as demonstrated by linearity plots. The internal control had 100% detection.

Example 3. BKV Amplification and Detection Specificity

The amplification oligonucleotides were evaluated to determine specificity of target by testing other organisms common to organ transplant samples. BK Virus Culture Fluid was used as a positive control. Forty-two organisms commonly found in blood or urine were prepared in 10 panels by spiking as close as possible (dependent on availability) to 1E6 cp/mL into STM. Each panel was evaluated for specificity.

TABLE 3-1

Overview.

| PPR mixes | Amplification Primer SEQ ID NO. Forward | Reverse | Probe oligonucleotide SEQ ID NO. | Target Region |
|---|---|---|---|---|
| 1 | 13 | 14 | 15 | BK VP2 gene |

TABLE 3-2

Samples.

| Sample | Sample Description | Conc. (cp/rxn) | # Ext | # PCR reps per ext | Final n |
|---|---|---|---|---|---|
| Pre-made Specificity Panels | See Table 3-6 for descriptions | n/a | 1 | 3 | 3 |
| Oligonucleotide Panel | PPR Mix 1 | n/a | 1 | 3 | 3 |
| BK Plasmid | BK Plasmid in STM | 1000 | 1 | 3 | 3 |
| Neg Ctrl | Neg Control (STM) | n/a | 1 | 3 | 3 |

Total reps per PPR = 30

TABLE 3-4

PPR Mix.

| Name | SEQ ID NO. | Units | Stock Conc. | Final Conc. | x1.25 | µL |
|---|---|---|---|---|---|---|
| BK VP2 FP04 | 13 | µM | 136.70 | 0.60 | 0.75 | 5.76 |
| BL VP2 RP04 | 14 | µM | 191.07 | 0.60 | 0.50 | 2.75 |
| BL VP2 PR04 | 15 | µM | 125.85 | 0.40 | 0.75 | 6.26 |
| SCR-F03 (IC) | 53 | µM | 223.29 | 0.60 | 0.75 | 3.53 |
| SCR-R03 (IC) | 54 | µM | 254.55 | 0.60 | 0.75 | 3.09 |
| SCR-Probe 03a (IC) | 55 | µM | 130.81 | 0.40 | 0.75 | 6.02 |
| Tris, pH 8.0 | | mM | 1000.00 | 5.00 | 6.25 | 6.56 |
| MgCl2 | | mM | 1000.00 | 4.00 | 5.00 | 5.25 |
| KCl | | mM | 2000.00 | 65.00 | 81.25 | 42.66 |
| Water | | | | | | 968.12 |
| Total: | | | | | | 1050.00 |

TABLE 3-5

Oligonucleotides.

| SEQ ID NO. | Sequence 5' → 3' | Modifications |
|---|---|---|
| | BKV Target | |
| 13 | CCCTACTTGAGCCAARGAACTAA | none |
| 14 | GGCCTAACWCCTCAAACATATGC | 7 5-Me-dCs |
| 15 | TTAAAGCAGCAAACCCAGCAATAGCC | 7 5-Me-dCs, 5' CalRed610, 3' BHQ2 |
| | IC Target | |
| 53 | ATGGTCAATTAGAGACAAAG | None |
| 54 | CGTTCACTATTGGTCTCTGC | None |
| 55 | CGGAATCACAAGTCAATCATCGCGCA | 5' Q705, 3' BHQ2 |

Conclusion: The BKV oligonucleotides were non-reactive with all organisms tested. The oligonucleotides did not amplify or detect any of the challenge organisms. Therefore, the BKV oligonucleotides are specific for BKV. In addition, ThermoBLAST™ in silico analysis predicted inclusivity of 333 BKV reference genomes for the targeted BKV region. Specificity analysis was performed on several viral, bacterial, environmental, invertebrate, and plant genomes along with the human genome. Results showed no hybridization of the BKV oligonucleotides to non-specific genomes and no amplification of non-target amplicons. Internal control was detected in all tests. The positive control was positive for BKV and IC and the negative control was positive for IC only.

BKV reactivity was evaluated in the presence of organisms from the specificity study. Briefly, panels 2-8 from the specificity study were diluted 1:10 in STM and BKV was spiked in at 1000 cpr. Panels 1, 9, 10, and 11 were prepared fresh in STM and BKV was spiked in at the same concentration. EBV was also spiked into each panel to evaluate EBV interference. Each panel was evaluated for BKV performance in the presence of 4-5 commonly found organisms with a PCR formulation including amplification primers and probe oligonucleotides listed in Table 1 and Table 2. Experimental details are described in SD-JYF-000019. Panel composition and reactivity results can be found in Table 14 and FIG. 12. Results were compared to a positive control consisting of BKV at 1000 cpr in STM. BKV was detected in 100% of the panels with no more than a 0.5 Ct shift when compared to the positive control. The internal control was detected in 100% of the panels. Positive control was positive for BKV and IC and the negative control was positive for IC only.

TABLE 3-6

BKV Specificity Results.

| Panel | Organism | Strain | ATCC/PN# | Final Conc. | Units | Reactivity |
|---|---|---|---|---|---|---|
| 1 | Varicella Zoster Virus (VZV) Isolate A Culture Fluid | Isolate A | 0810172CF | $1.00 \times 10^6$ | cp/mL | 0/3 = 0% |
|   | Epstein-Barr Virus (EBV) Culture Fluid | B95-8 | 0810008CF | $1.00 \times 10^6$ | cp/mL |  |
|   | NATtrol Human Parvovirus B19 | B19 | NATPARVO-0003 | $1.00 \times 10^5$ | IU/mL |  |
|   | CMV | RC256 | 0810003CF | $1.00 \times 10^6$ | TCID50/mL |  |
|   | JC Viral DNA | MAD1 | 17-943-500 | $1.00 \times 10^5$ | cp/mL |  |
| 2 | *Candida albicans* | CBS 562 | 18804 | $1.00 \times 10^6$ | CFU/mL | 0/3 = 0% |
|   | *Chlamydia trachomatis* - Serovar E | Serovar E | VR-348B | $1.00 \times 10^6$ | IFU/mL |  |
|   | CULTURED VIRUS, HIV-1 TYPE B | Type B | n/a | $1.00 \times 10^5$ | cp/mL |  |
|   | Hepatitis A virus, Strain HML75 | HM175 | VR-2093 | $1.43 \times 10^5$ | TCID50/mL |  |
| 3 | Dengue Virus Type 1 Culture Fluid | Hawaii | 0810088CF | $1.43 \times 10^4$ | TCID50/mL | 0/3 = 0% |
|   | Dengue Virus Type 2 Culture Fluid | New Guinea C | 0810089CF | $1.43 \times 10^4$ | TCID50/mL |  |
|   | Dengue Virus Type 3 Culture Fluid | H87 | 0810090CF | $1.43 \times 10^5$ | TCID50/mL |  |
|   | Dengue Virus Type 4 Culture Fluid | H241 | 0810091CF | $1.43 \times 10^4$ | TCID50/mL |  |
| 4 | Herpes Simplex Virus Type 2 (HSV-2) Strain MS | MS | n/a | $1.43 \times 10^4$ | TCID50/mL | 0/3 = 0% |
|   | HIV Type 2 (HIV-2) Culture Fluid | NIH-Z | 0810029CF | $1.43 \times 10^3$ | TCID50/mL |  |
|   | HPV type 18 purified plasmid DNA | Type 18 | 45152D | $1.00 \times 10^6$ | cp/mL |  |
|   | Synthetic Human Papillomavirus 16 DNA | Type 16 | VR-3240SD | $1.00 \times 10^4$ | cp/mL |  |
| 5 | Human Herpes Virus Type 6A (HHV-6A) (Strain: GS) Culture Fluid | GS | 0810529CF | $1.00 \times 10^6$ | cp/mL | 0/3 = 0% |
|   | Human Herpes Virus Type 6B. (HHV-6B) (Strain: Z29) Culture Fluid | Z29 | 0810072CF | $1.00 \times 10^6$ | cp/mL |  |
|   | Human Herpes Virus Type 7 (HHV-7) Culture Fluid | SB | 0810071CF | $1.43 \times 10^6$ | TCID50/mL |  |
|   | Human Herpes Virus Type 8 (HHV-8) Culture Fluid | n/a | 0810104CF | $1.00 \times 10^6$ | cp/mL |  |
| 6 | Human T-Lymphotropic Virus Type I (HTLV-I) Culture Fluid | n/a | 0801033CF | $1.00 \times 10^6$ | vp/mL | 0/3 = 0% |
|   | Human T-Lymphotropic Virus Type II (HTLV-II) Culture Fluid | n/a | 0810039CF | $1.00 \times 10^6$ | vp/mL |  |
|   | NATtral Human Hepatitis B Virus (HBV) | n/a | NATHBV-0003 | $1.00 \times 10^4$ | cp/mL |  |
|   | NATtral Human Hepatitis C Virus (HCV) | n/a | NATHCV-0005 | $1.00 \times 10^4$ | cp/mL |  |
| 7 | *Mycobacterium smegmatis* | W-113 | 14468 | $1.00 \times 10^6$ | CFU/mL | 0/3 = 0% |
|   | *Neisseria gonorrhoeae* | NCTC 8375 | 19424 | $1.00 \times 10^6$ | CFU/mL |  |
|   | *Propionibacterium acnes* | NCTC 737 | 6919 | $1.00 \times 10^6$ | CFU/mL |  |
|   | *Staphylococcus aureus* | NCTC 8532 | 12600 | $1.00 \times 10^6$ | CFU/mL |  |

TABLE 3-6-continued

BKV Specificity Results.

| Panel | Organism | Strain | ATCC/PN# | Final Conc. | Units | Reactivity |
|---|---|---|---|---|---|---|
| 8 | NATtrol West Nile Virus (WNV) Strain: NY 2001-6263 | NY 2001-6263 | NATH CV-0005 | $5.00 \times 10^3$ | cp/mL | 0/3 = 0% |
|  | Vaccinia Virus Culture Fluid | "Vaccine" | 0810310CF | 0.00 | TCID50/mL |  |
|  | Trichomonas vaginalis | JH 31A#4 | 30236 | $1.00 \times 10^6$ | cells/mL |  |
|  | Staphylococcus epidermidis | RP62A | 35984 | $1.00 \times 10^6$ | CFU/mL |  |
|  | HSV-1 Strain MacIntyre | MacIntyre | VR-539 | $1.43 \times 10^4$ | TCID50/mL |  |
|  | Mycobacterium gordonae | L. Wayne W-1609 | 14470 | $1.00 \times 10^6$ | cp/mL |  |
| 9 | Acinetobacter lwoffii | GP0714 | 15309 | $1.00 \times 10^6$ | CFU/mL | 0/3 = 0% |
|  | Enterobacter cloacae | GP0130 | 13047 | $1.00 \times 10^6$ | CFU/mL |  |
|  | Escherichia coli | GP0014 | 11775 | $1.00 \times 10^6$ | CFU/mL |  |
|  | Klebsiella pneumoniae | GP0040 | 23357 | $1.00 \times 10^6$ | CFU/mL |  |
| 10 | Proteus mirabilis | GP0110 | 29906 | $1.00 \times 10^6$ | CFU/mL | 0/3 = 0% |
|  | Pseudomonas aeruginosa | GP0736 | 10145 | $1.00 \times 10^6$ | CFU/mL |  |
|  | Streptococcus agalactiae | GP0744 | 13813 | $1.00 \times 10^6$ | CFU/mL |  |

TABLE 3-7

BKV Specificity Results.

| Organism | Final Conc. | Units | Reactivity |
|---|---|---|---|
| BK Virus Culture Fluid | $2.78 \times 10^4$ | cp/mL | 1/1 = |
| CMV | $1.43 \times 10^5$ | TCID50/mL | 100% |
| NATtrol Human Parvovirus B19 | $1.00 \times 10^5$ | IU/mL |  |
| Varicella Zoster Virus (VZV) Isolate A Culture Fluid | $1.00 \times 10^6$ | cp/mL |  |
| BK Virus Culture Fluid | $2.78 \times 10^4$ | cp/mL | 1/1 = |
| Candida albicans | $1.00 \times 10^6$ | CFU/mL | 100% |
| Chlamydia trachomatis - Serovar E | $1.00 \times 10^6$ | IFU/mL |  |
| CULTURED VIRUS, HIV-1 TYPE B | $1.00 \times 10^5$ | cp/mL |  |
| Hepatitis A virus, Strain HM175 | $1.43 \times 10^5$ | TCID50/mL |  |
| BK Virus Culture Fluid | $2.78 \times 10^4$ | cp/mL | 1/1 = |
| Dengue Virus Type 1 Culture Fluid | $1.43 \times 10^4$ | TCID50/mL | 100% |
| Dengue Virus Type 2 Culture Fluid | $1.43 \times 10^4$ | TCID50/mL |  |
| Dengue Virus Type 3 Culture Fluid | $1.43 \times 10^5$ | TCID50/mL |  |
| Dengue Virus Type 4 Culture Fluid | $1.43 \times 10^4$ | TCID50/mL |  |
| BK Virus Culture Fluid | $2.78 \times 10^4$ | cp/mL | 1/1 = |
| Herpes Simplex Virus Type 2 (HSV-2) Strain MS | $1.43 \times 10^4$ | TCID50/mL | 100% |
| HIV Type 2 (HIV-2) Culture Fluid | $1.43 \times 10^3$ | TCID50/mL |  |
| HPV type 18 purified plasmid DNA | $1.00 \times 10^6$ | cp/mL |  |
| Synthetic Human Papillomavirus 16 DNA | $1.00 \times 10^4$ | cp/mL |  |
| BK Virus Culture Fluid | $2.78 \times 10^4$ | cp/mL | 1/1 = |
| Human Herpes Virus Type 6A (Strain: GS) Culture Fluid | $1.00 \times 10^6$ | cp/mL | 100% |
| Human Herpes Virus Type 6B (Strain: Z29) Culture Fluid | $1.00 \times 10^6$ | cp/mL |  |
| Human Herpes Virus Type 7 (HHV-7) Culture Fluid | $1.43 \times 10^6$ | TCID50/mL |  |
| Human Herpes Virus Type 8 (HHV-8) Culture Fluid | $1.00 \times 10^6$ | cp/mL |  |
| BK Virus Culture Fluid | $2.78 \times 10^4$ | cp/mL | 1/1 = |
| Human T-Lymphotropic Virus Type I Culture Fluid | $1.00 \times 10^6$ | vp/mL | 100% |
| Human T-Lymphotropic Virus Type II Culture Fluid | $1.00 \times 10^6$ | vp/mL |  |
| NATtrol Human Hepatitis B Virus (HBV) | $1.00 \times 10^4$ | cp/mL |  |
| NATtrol Human Hepatitis C Virus (HCV) | $1.00 \times 10^4$ | cp/mL |  |
| BK Virus Culture Fluid | $2.78 \times 10^4$ | cp/mL | 1/1 = |
| Mycobacterium smegmatis | $1.00 \times 10^6$ | CFU/mL | 100% |
| Neisseria gonorrhoeae | $1.00 \times 10^6$ | CFU/mL |  |
| Propionibacterium acnes | $1.00 \times 10^6$ | CFU/mL |  |
| Staphylococcus aureus | $1.00 \times 10^6$ | CFU/mL |  |
| BK Virus Culture Fluid | $2.78 \times 10^4$ | cp/mL | 1/1 = |
| NATtrol West Nile Virus (WNV) Strain: NY 2001-6263 | $5.00 \times 10^3$ | cp/mL | 100% |
| Vaccinia Virus Culture Fluid | $0.00 \times 10^0$ | TCID50/mL |  |
| Trichomonas vaginalis | $1.00 \times 10^6$ | cells/mL |  |
| Staphylococcus epidermidis | $1.00 \times 10^6$ | CFU/mL |  |
| HSV-1 Strain MacIntyre | $1.43 \times 10^4$ | TCID50/mL |  |
| Mycobacterium gordonae | $1.00 \times 10^6$ | cp/mL |  |
| BK Virus Culture Fluid | $2.78 \times 10^4$ | cp/mL | 1/1 = |
| Acinetobacter lwoffii | $1.00 \times 10^6$ | CFU/mL | 100% |
| Enterobacter cloacae | $1.00 \times 10^6$ | CFU/mL |  |
| Escherichia coli | $1.00 \times 10^6$ | CFU/mL |  |
| BK Virus Culture Fluid | $2.78 \times 10^4$ | cp/mL |  |
| Klebsiella pneumoniae | $1.00 \times 10^6$ | CFU/mL |  |
| Proteus mirabilis | $1.00 \times 10^6$ | CFU/mL |  |
| Pseudomonas aeruginosa | $1.00 \times 10^6$ | CFU/mL |  |
| BK Virus Culture Fluid | $2.78 \times 10^4$ | cp/mL | 1/1 = |
| Streptococcus agalactiae | $1.00 \times 10^6$ | CFU/mL | 100% |

Example 4. JC Cross Reactivity

The oligonucleotides were evaluated to determine if there is any cross-reactivity of the described BKV oligonucleotides with JC viral DNA or high titer JC plasmids. BKV shares 75% homology with JC Virus. In silico analysis indicated no cross-reactivity with JC Virus sequences.

TABLE 4-1

Overview.

| PPR mixes | Amplification Primer SEQ ID NO. First | Amplification Primer SEQ ID NO. Second | Probe oligonucleotide SEQ ID NO. | Target Region | Clone |
|---|---|---|---|---|---|
| 1 | 1 | 2 | 3 | BK VP1 gene | n/a (9 tests) |
| 2 | 4 | 5 | 6 | BK VP2 gene | JC GB1 |
| 3 | 7 | 9 | 8 | BK VP2 gene | n/a (9 tests) |
| 4 | 10 | 12 | 11 | BK VP2 gene | JC GB1 |
| 5 | 13 | 14 | 15 | BK VP2 gene | JC GB1 |
| 6 | 16 | 18 | 17 | BK VP2 gene | JC GB6 |

TABLE 4-1-continued

Overview.

| PPR mixes | Amplification Primer SEQ ID NO. First | Amplification Primer SEQ ID NO. Second | Probe oligonucleotide SEQ ID NO. | Target Region | Clone |
|---|---|---|---|---|---|
| 7 | 21 | 19 | 20 | BK VP2 gene | JC GB1 |
| 8 | 24 | 22 | 23 | BK VP2 gene | JC GB1 |

TABLE 4-2

Samples.

| Sample | Sample Description | Conc. (cp/rxn) | # of tubes | #-Ext | # PCR reps per ext | Final n per PPR |
|---|---|---|---|---|---|---|
| JC alone | JC viral DNA in STM | 10000 | 8 | 1 | 3 | 3 |
| JC plasmid | Plasmid @high cpr | 1000000 | 8 | 1 | 3 | 3 |
| BK Alone | BKCF | 100 | 8 | 1 | 3 | 3 |
| Neg. Ctrl | STM | n/a | 8 | 1 | 3 | 3 |
| Total reps per PPR | | | | | | 96 |

TABLE 4-3

Settings

| Channel | CrossTalk Correction | Convergence Cycle | End Cycle Cutoff | Positivity/CT Threshold |
|---|---|---|---|---|
| FAM | n/a | n/a | n/a | n/a |
| HEX | n/a | n/a | n/a | n/a |
| ROX | n/a | 10 | 10 | 500 |
| RED647 | n/a | n/a | n/a | n/a |
| RED677 | n/a | 10 | n/a | 500 |

TABLE 4-4

Panel Preparation: JC Plasmids

| Name | Clone ID | Sample Format | Concentration (cp/mL) |
|---|---|---|---|
| JC Clone 1 | 100976 | Linearized Plasmid | $1.00 \times 10^9$ |
| JC Clone 6 | 100980 | Linearized Plasmid | $1.00 \times 10^9$ |

TABLE 4-5

Preparation of JC samples.

| $C_i$ (cp/mL) | $C_f$ (cp/mL) | testing amount (cp/rxn) | $V_i$ (μL) | μL of STM | $V_f$ (μL) | |
|---|---|---|---|---|---|---|
| $1.00 \times 10^9$ | $2.78 \times 10^7$ | $1 \times 10^6$ | 97.2 | 3402.8 | 3500.00 | Clone 1 |
| $1.00 \times 10^9$ | $2.78 \times 10^7$ | $1 \times 10^6$ | 22.2 | 777.8 | 800.00 | Clone 6 |

TABLE 4-6

JC Viral DNA

| Name | MFG# | Manufacturer | Sample Format | Concentration (cp/mL) |
|---|---|---|---|---|
| JC Viral DNA, MAD1 strain | 17-943-500/J02003 | Advanced Biotechnologies | Viral DNA | $5.20 \times 10^6$ |

TABLE 4-7

| $C_i$ (cp/mL) | $C_f$ (cp/mL) | testing amount (cp/rxn) | $V_i$ (μL) | μL of STM | $V_f$ (μL) |
|---|---|---|---|---|---|
| $5.20 \times 10^6$ | $2.78 \times 10^5$ | $1.0 \times 10^4$ | 267.1 | 4732.9 | 5000.00 |

TABLE 4-8

BK Culture Fluid.

| $C_i$ (cp/mL) | $C_f$ (cp/mL) | testing amount (cp/rxn) | $V_i$ (μL) | μL of STM | $V_f$ (μL) |
|---|---|---|---|---|---|
| $1.00 \times 10^5$ | $2.78 \times 10^3$ | $1.0 \times 10^2$ | 138.9 | 4861.1 | 5000.00 |

PCR Mixes:

TABLE 4-9

IC Oligo Mix.

| Name | Units | Stock Conc. | Final Conc. | ×1.25 | μL |
|---|---|---|---|---|---|
| 50× DNA IC amplification primer mix | x | 50.00 | 1.00 | 1.00 | 99.00 |
| 50× DNA IC probe oligonucleotide | x | 50.00 | 1.00 | 1.00 | 99.00 |
| Tris, pH 8.0 | mM | 1000.00 | 5.00 | 6.25 | 30.94 |
| MgCl$_2$ | mM | 1000.00 | 4.00 | 5.00 | 24.75 |
| KCl | mM | 2000.00 | 65.00 | 81.25 | 201.09 |
| | | | | Total | 454.78 |

Total IC tests needed 72
IC Mix Volumes 4950 (<~9*12 (550 μL tests))
IC Mix per Multiplex PPR 50.53

TABLE 4-10

VP1 PPR Mix.

| SEQ ID NO. | Units | Stock Conc. | Final Conc. | ×1.25 | μL |
|---|---|---|---|---|---|
| 1 | μM | 143.53 | 0.60 | 0.75 | 2.87 |
| 2 | μM | 175.10 | 0.60 | 0.75 | 2.36 |
| 3 | μM | 83.38 | 0.40 | 0.50 | 3.30 |
| IC Oligo Mix | x | 1.00 | 1.00 | 1.00 | 50.53 |
| Water | | | | | 490.94 |
| Total | | | | | 550.00 |

TABLE 4-11

VP2-1 PPR Mix.

| SEQ ID NO. | Units | Stock Conc. | Final Conc. | ×1.25 | μL |
|---|---|---|---|---|---|
| 4 | μM | 193.80 | 0.60 | 0.75 | 2.13 |
| 5 | μM | 171.58 | 0.60 | 0.75 | 2.40 |
| 6 | μM | 34.99 | 0.40 | 0.50 | 7.86 |
| IC Oligo Mix | x | 1.00 | 1.00 | 1.00 | 50.53 |
| | | | | Water | 487.08 |
| | | | | Total | 550.00 |

TABLE 4-12

VP2-2 PPR Mix.

| SEQ ID NO. | Units | Stock Conc. | Final Conc. | ×1.25 | μL |
|---|---|---|---|---|---|
| 7 | μM | 147.44 | 0.60 | 0.75 | 2.80 |
| 8 | μM | 71.48 | 0.60 | 0.75 | 5.77 |
| 9 | μM | 158.44 | 0.40 | 0.50 | 1.74 |
| IC Oligo Mix | x | 1.00 | 1.00 | 1.00 | 50.53 |
| | | | | Water | 489.16 |
| | | | | Total: | 550.00 |

TABLE 4-13

VP2-3 PPR Mix.

| SEQ ID NO. | Units | Stock Conc. | Final Conc. | ×1.25 | μL |
|---|---|---|---|---|---|
| 10 | μM | 157.34 | 0.60 | 0.75 | 2.62 |
| 11 | μM | 59.24 | 0.60 | 0.75 | 6.96 |
| 12 | μM | 148.55 | 0.40 | 0.50 | 1.85 |
| IC Oligo Mix | x | 1.00 | 1.00 | 1.00 | 50.53 |
| | | | | Water | 488.03 |
| | | | | Total: | 550.00 |

TABLE 4-1

VP2-4 PPR Mix.

| SEQ ID NO. | Units | Stock Conc. | Final Conc. | ×1.25 | μL |
|---|---|---|---|---|---|
| 13 | μM | 136.70 | 0.60 | 0.75 | 3.02 |
| 15 | μM | 125.82 | 0.60 | 0.75 | 3.28 |
| 14 | μM | 191.07 | 0.40 | 0.50 | 1.44 |
| IC Oligo Mix | x | 1.00 | 1.00 | 1.00 | 50.53 |
| | | | | Water | 491.73 |
| | | | | Total: | 550.00 |

TABLE 4-15

VP2-5 PPR Mix.

| SEQ ID NO. | Units | Stock Conc. | Final Conc. | ×1.25 | μL |
|---|---|---|---|---|---|
| 16 | μM | 180.35 | 0.60 | 0.75 | 2.29 |
| 17 | μM | 91.65 | 0.60 | 0.75 | 4.50 |
| 18 | μM | 170.07 | 0.40 | 0.50 | 1.62 |
| IC Oligo Mix | x | 1.00 | 1.00 | 1.00 | 50.53 |
| | | | | Water | 491.06 |
| | | | | Total: | 550.00 |

TABLE 4-16

VP2-6 PPR Mix.

| SEQ ID NO. | Units | Stock Conc. | Final Conc. | ×1.25 | μL |
|---|---|---|---|---|---|
| 19 | μM | 163.04 | 0.60 | 0.75 | 2.53 |
| 20 | μM | 64.90 | 0.60 | 0.75 | 6.36 |
| 21 | μM | 160.88 | 0.40 | 0.50 | 1.71 |
| IC Oligo Mix | x | 1.00 | 1.00 | 1.00 | 50.53 |
| | | | | Water | 488.87 |
| | | | | Total: | 550.00 |

TABLE 4-17

VP2-7 PPR Mix

| SEQ ID NO. | Units | Stock Conc. | Final Conc. | ×1.25 | μL |
|---|---|---|---|---|---|
| 22 | μM | 170.91 | 0.60 | 0.75 | 2.41 |
| 23 | μM | 110.52 | 0.60 | 0.75 | 3.73 |
| 24 | μM | 223.08 | 0.40 | 0.50 | 1.23 |
| IC Oligo Mix | x | 1.00 | 1.00 | 1.00 | 50.53 |
| | | | | Water | 492.09 |
| | | | | Total: | 550.00 |

Oligonucleotides are as described in Table 2-15.

TABLE 4-18b

Oligo Info - Description

| Target | SEQ ID NO. | Sequence 5' → 3' | Modifications |
|---|---|---|---|
| IC | 53 | ATGGTCAATTAGAGACAAAG | NONE |
| | 54 | CGITCACTATTGGTCTCTGC | NONE |
| | 55 | CGGAATCACAAGTCAATCAT CGCGCA | 5' Q705 AND 3' BHQ2 |

TABLE 4-19

Results (ROX).

| Target | Sample Type | Conc. (cpr) | Pos | AVG Ct | SD Ct | AVG RFU | SD RFU | AVG Bckgrd | SD Bckgrd | AVG Tslope | SD Tslope |
|---|---|---|---|---|---|---|---|---|---|---|---|
| VP1-1 | BK Culture Fluid | 100 | 3 | 34.03 | 0.22 | 3237.27 | 640.49 | 336.96 | 26.20 | 234.37 | 33.71 |
| | JC Viral DNA | 10000 | | | | | | 303.20 | 26.57 | | |
| | STM | n/a | | | | | | 319.95 | 22.06 | | |
| VP2-1 | BK Culture Fluid | 100 | 3 | 34.16 | 0.33 | 7366.09 | 507.95 | 1864.50 | 99.04 | 279.73 | 53.48 |
| | JC Viral DNA | 10000 | 1 | 41.81 | | 637.58 | | 2045.30 | 174.52 | 63.09 | |
| | Plasmid | 1000000 | | | | | | 1992.72 | 55.35 | | |
| | STM | n/a | | | | | | 1870.36 | 115.52 | | |
| VP2-2 | BK Culture Fluid | 100 | 3 | 33.49 | 0.02 | 9097.89 | 103.53 | 621.65 | 11.00 | 310.42 | 5.90 |
| | JC Viral DNA | 10000 | 3 | 37.64 | 1.58 | 7522.62 | 1852.37 | 690.95 | 4.06 | 284.52 | 39.31 |
| | STM | n/a | | | | | | 655.99 | 22.25 | | |
| VP2-3 | BK Culture Fluid | 100 | 3 | 32.54 | 0.21 | 7936.63 | 1507.15 | 2385.49 | 55.29 | 270.11 | 38.46 |
| | JC Viral DNA | 10000 | 3 | 37.56 | 1.21 | 1615.03 | 441.92 | 2307.23 | 244.75 | 150.40 | 24.75 |
| | Plasmid | 1000000 | | | | | | 2368.86 | 111.35 | | |
| | STM | n/a | | | | | | 2472.71 | 142.75 | | |
| VP2-4 | BK Culture Fluid | 100 | 3 | 32.75 | 0.19 | 11289.06 | 300.23 | 1897.45 | 6.78 | 271.17 | 24.77 |
| | JC Viral DNA | 10000 | 3 | 36.55 | 0.59 | 9238.87 | 1024.91 | 1872.47 | 154.60 | 339.36 | 15.83 |
| | Plasmid | 1000000 | | | | | | 1858.10 | 17.42 | | |
| | STM | n/a | | | | | | 1875.79 | 60.28 | | |
| VP2-5 | BK Culture Fluid | 100 | 3 | 34.23 | 0.23 | 7327.55 | 959.40 | 767.19 | 11.02 | 337.91 | 38.49 |
| | JC Viral DNA | 10000 | 3 | 38.04 | 0.48 | 3328.47 | 340.76 | 786.71 | 38.00 | 288.84 | 35.45 |
| | Plasmid | 1000000 | 3 | 39.23 | 0.26 | 1217.48 | 245.97 | 737.90 | 63.18 | 152.46 | 19.78 |
| | STM | n/a | | | | | | 732.26 | 26.43 | | |
| VP2-6 | BK Culture Fluid | 100 | 3 | 33.11 | 0.48 | 9797.88 | 603.27 | 1727.33 | 97.42 | 310.20 | 47.96 |
| | JC Viral DNA | 10000 | 3 | 38.66 | 1.74 | 5539.59 | 2000.05 | 1482.83 | 185.77 | 259.99 | 6.55 |
| | Plasmid | 1000000 | | | | | | 1746.82 | 157.43 | | |
| | STM | n/a | | | | | | 1698.41 | 168.32 | | |
| VP2-7 | BK Culture Fluid | 100 | 3 | 33.11 | 0.04 | 10503.77 | 417.05 | 1480.13 | 41.94 | 379.96 | 9.26 |
| | JC Viral DNA | 10000 | 3 | 37.51 | 0.80 | 7381.99 | 1345.43 | 1500.23 | 21.88 | 293.04 | 29.35 |
| | Plasmid | 1000000 | | | | | | 1539.68 | 87.62 | | |
| | STM | n/a | | | | | | 1522.60 | 118.19 | | |

TABLE 4-20

BKV oligonucleotide mismatches with JCV sequence

| Target | SEQ ID NO. | JC Virus mismatches |
|---|---|---|
| VP1-1 | 1 | 2 |
| | 2 | 0 |
| | 3 | >10 bp delete |
| VP2-1 | 4 | 2 |
| | 5 | 2 |
| | 6 | 4 |
| VP2-2 | 7 | not present |
| | 8 | 3 |
| | 9 | 3 |
| VP2-3 | 10 | 8 |
| | 11 | 6 |
| | 12 | 6 |
| VP2-4 | 13 | 8 |
| | 14 | 5 |
| | 15 | 2 |
| VP2-5 | 16 | 0 |
| | 17 | 3 |
| | 18 | 4 |
| VP2-6 | 19 | 8 |
| | 20 | 6 |
| | 21 | 4 |
| VP2-7 | 22 | 8 |
| | 23 | 5 |
| | 24 | 2 |

TABLE 4-21

Results (Quasar 705)

| Target | Sample Type | Conc. (cpr) | Pos | AVG Ct | SD Ct | AVG RFU | SD RFU | AVG Bckgrd | SD Bckgrd | AVG Tslope | SD Tslope |
|---|---|---|---|---|---|---|---|---|---|---|---|
| VP1-1 | BK Culture Fluid | 100 | 3 | 27.49 | 0.08 | 3802.50 | 331.38 | 1289.70 | 111.02 | 288.76 | 13.94 |

TABLE 4-21-continued

Results (Quasar 705)

| Target | Sample Type | Conc. (cpr) | Pos | AVG Ct | SD Ct | AVG RFU | SD RFU | AVG Bckgrd | SD Bckgrd | AVG Tslope | SD Tslope |
|---|---|---|---|---|---|---|---|---|---|---|---|
| | JC Viral DNA | 10000 | 3 | 27.42 | 0.14 | 3414.38 | 346.54 | 1119.54 | 119.97 | 293.25 | 20.55 |
| | STM | n/a | 3 | 27.62 | 0.13 | 3404.00 | 262.82 | 1166.34 | 111.75 | 259.80 | 16.93 |
| VP2-1 | BK Culture Fluid | 100 | 3 | 27.49 | 0.11 | 3489.28 | 262.87 | 1217.90 | 76.48 | 286.42 | 17.07 |
| | JC Viral DNA | 10000 | 3 | 27.14 | 0.21 | 4673.51 | 853.00 | 1634.25 | 331.56 | 367.99 | 57.04 |
| | Plasmid | 1000000 | 3 | 26.84 | 0.04 | 4835.51 | 159.74 | 1665.00 | 18.99 | 259.15 | 2.29 |
| | STM | n/a | 3 | 27.72 | 0.10 | 3100.01 | 190.02 | 1123.11 | 38.18 | 254.66 | 1335 |
| VP2-2 | BK Culture Fluid | 100 | 3 | 27.69 | 0.08 | 3033.62 | 141.41 | 1068.43 | 40.00 | 255.72 | 4.42 |
| | JC Viral DNA | 10000 | 3 | 27.72 | 0.08 | 3202.49 | 185.78 | 1168.90 | 37.45 | 257.69 | 12.88 |
| | STM | n/a | 3 | 27.60 | 0.05 | 3176.53 | 151.11 | 1124.60 | 47.21 | 269.10 | 8.37 |
| VP2-3 | BK Culture Fluid | 100 | 3 | 27.32 | 0.09 | 3509.34 | 280.00 | 1380.34 | 84.80 | 318.71 | 2435 |
| | JC Viral DNA | 10000 | 3 | 27.19 | 0.08 | 3790.08 | 217.74 | 1447.12 | 123.35 | 354.60 | 22.34 |
| | Plasmid | 1000000 | 3 | 27.26 | 0.10 | 3897.88 | 229.38 | 1474.64 | 67.62 | 350.39 | 25.99 |
| | STM | n/a | 3 | 27.37 | 0.05 | 3582.33 | 72.45 | 1410.07 | 33.18 | 315.94 | 5.90 |
| VP2-4 | BK Culture Fluid | 100 | 3 | 27.38 | 0.07 | 3608.25 | 156.33 | 1417.92 | 56.17 | 308.65 | 12.92 |
| | JC Viral DNA | 10000 | 3 | 27.25 | 0.12 | 3726.88 | 159.28 | 1417.28 | 65.26 | 328.56 | 22.10 |
| | Plasmid | 1000000 | 3 | 27.25 | 0.02 | 3651.48 | 107.07 | 1377.15 | 38.76 | 326.40 | 1.72 |
| | STM | n/a | 3 | 27.29 | 0.14 | 3547.01 | 233.77 | 1364.01 | 82.47 | 326.29 | 29.19 |
| VP2-5 | BK Culture Fluid | 100 | 3 | 27.68 | 0.06 | 3024.80 | 130.89 | 1086.63 | 36.08 | 258.64 | 6.63 |
| | JC Viral DNA | 10000 | 3 | 27.63 | 0.03 | 2964.61 | 69.43 | 1071.86 | 54.34 | 262.66 | 4.87 |
| | Plasmid | 1000000 | 3 | 27.65 | 0.08 | 2942.63 | 247.15 | 1048.01 | 120.65 | 260.72 | 9.79 |
| | STM | n/a | 3 | 27.60 | 0.40 | 3492.41 | 816.16 | 1270.88 | 314.75 | 285.01 | 69.69 |
| VP2-6 | BK Culture Fluid | 100 | 3 | 27.32 | 0.06 | 4181.99 | 166.74 | 1411.75 | 66.60 | 324.99 | 11.49 |
| | JC Viral DNA | 10000 | 3 | 27.46 | 0.14 | 3872.36 | 476.46 | 1305.33 | 179.29 | 293.35 | 27.62 |
| | Plasmid | 1000000 | 3 | 27.31 | 0.05 | 4079.69 | 255.64 | 1431.37 | 109.48 | 320.99 | 10.95 |
| | STM | n/a | 3 | 27.35 | 0.08 | 3976.00 | 216.18 | 1341.58 | 88.16 | 317.14 | 16.63 |
| VP2-7 | BK Culture Fluid | 100 | 3 | 27.91 | 0.11 | 2487.85 | 274.21 | 941.76 | 85.52 | 262.50 | 39.60 |
| | JC Viral DNA | 10000 | 3 | 27.50 | 0.35 | 3083.14 | 466.48 | 1171.80 | 193.41 | 290.97 | 52.18 |
| | Plasmid | 1000000 | 3 | 27.44 | 0.06 | 3232.58 | 111.05 | 1251.94 | 15.26 | 294.49 | 8.06 |
| | STM | n/a | 3 | 28.08 | 0.45 | 2267.09 | 84.90 | 896.26 | 32.44 | 304.51 | 6.14 |

Conclusion: All of the BKV oligonucleotides showed some amplification with the JC Viral DNA, though some did not cross the set detection threshold. This low-level detection occurred even where the using amplification primers and probe oligonucleotides (SEQ ID NOs: 1-3, 7) for which there is a deletion region or the related target sequence does not exist for the JC virus. Additionally, the high-titer JC clones did not show cross reactivity with the BKV oligonucleotides, except where in silico analysis would predict some (SEQ ID NOs: 4-5, 16-17). This indicates the observed detection in the JC virus samples is actually a detection of BKV contamination in the purchased JC Viral DNA rather than amplification of JC nucleic acid sequence. Sequencing of the amplicon purified from the amplification showed 100% homology to the BK genome, further indicated BKV contamination of the JC viral sample. To additionally confirm the specificity of the BKV ASRs, a plasmid clone encoding the analogous region of JC virus was generated. The clone was tested at $1 \times 10^6$ copies per reaction and no amplification was observed with the BKV amplification primers. The JC plasmid was reactive to putative JC specific primers.

Example 5. Limit of Detection

The limits of detection of BK Virus in plasma using the described amplification primers and probe oligonucleotides were determined. BK Virus in pooled plasma was evaluated for reactivity with a PCR formulation. BK virus in culture fluid was spiked into each matrix at the indicated concentrations. The samples in plasma were diluted 1:0.2 with PBS containing 3 mg/mL Proteinase K (PK) and 10× K18 TCO.

TABLE 5-1

Fusion Thermocycling Conditions

| Temperature | Time | Cycles |
|---|---|---|
| 95° C. | 2:00 min | |
| 95° C. | 0:08 min | 45 |
| 60° C. | 0:25 min | |

TABLE 5-2

PPR Mixes.

| | Amplification Primers SEQ ID NO. | | Probe oligonucleotide | |
|---|---|---|---|---|
| PPR mix | First | Second | SEQ ID NO. | Target Region |
| 1 | 13 | 14 | 15 | BK VP2 gene |

TABLE 5-3

Samples.

| Sample | Sample Description | Conc. (cp/rxn) | # of tubes | # Ext | # PCR reps per ext | Final n per PPR |
|---|---|---|---|---|---|---|
| BKCF | BK Spiked in Plasma Neg Pool | 100, 31.62, 10, 3.16 | 3 | 2, 3 (for 1 tube) | 3 | 21 |
| Pos Ctrl | pre-made BK in STM | 100 | 1 | 1 | 3 | 3 |
| Neg Ctrl 1 | neg plasma pool + diluent (no BK) | n/a | 1 | 1 | 3 | 3 |
| Neg Ctrl 2 | STM | n/a | 1 | 1 | 3 | 3 |

Total reps: 93

TABLE 5-4

Settings.

| Channel | CrossTalk Correction | Convergence Cycle | End Cycle Cutoff | Positivity/CT Threshold |
|---|---|---|---|---|
| FAM | n/a | n/a | n/a | n/a |
| HEX | n/a | n/a | n/a | n/a |
| ROX | n/a | 10 | 10 | 500 |
| RED647 | n/a | n/a | n/a | n/a |
| RED677 | n/a | 10 | n/a | 500 |

TABLE 5-5

BK Virus Culture Fluid.

| MFG# | Manufacturer | Sample Format | Concentration (cp/mL) |
|---|---|---|---|
| 0810065CF | Zeptometrix | Culture Fluid | $1.57 \times 10^{10}$ |

TABLE 5-6

Bk Virus Description.

| $C_i$ (cp/mL) | $C_f$ (cp/mL) | $V_i$ (µL) | µL of TE | $V_f$ (µL) |
|---|---|---|---|---|
| $1.00 \times 10^9$ | $1.00 \times 10^8$ | 10.0 | 90.0 | 100.00 |
| $1.00 \times 10^8$ | $1.00 \times 10^7$ | 10.0 | 90.0 | 100.00 |
| $1.00 \times 10^7$ | $1.00 \times 10^6$ | 10.0 | 90.0 | 100.00 |
| $1.00 \times 10^6$ | $1.00 \times 10^5$ | 30.0 | 270.0 | 300.00 |

TABLE 5-7

BK Virus Description.

| $C_i$ (cp/mL) | $C_f$ (cp/mL) in reaction tube | final testing amount (cp/rxn) | 1.2X testing amount (for 1:0.2 dilution with diluent) | $V_i$ (µL) | µL of neg plasma pool | $V_f$ (µL) |
|---|---|---|---|---|---|---|
| $1.00 \times 10^5$ | 3333.33 | 100.00 | 120.00 | 217.2 | 6298.1 | 6515.33 |
| 3333.33 | 1054.09 | 31.62 | 37.95 | 2015.3 | 4357.7 | 6373.02 |
| 1054.09 | 333.33 | 10.00 | 12.00 | 1873.0 | 4050.0 | 5923.02 |
| 333.33 | 105.41 | 3.16 | 3.79 | 1423.0 | 3077.0 | 4500.00 |
| Transfer 4250 µL of bulk to separate tube | | | | 17782.8 | | |

Add 850 µL diluent, incubate for 30'
Transfer 1500 µL to three separate tubes for n = 21 for each concentration

TABLE 5-8

Oligonucleotide and Reagent concentrations.

| Name | SEQ ID NO. | Units | Stock Conc. | Final Conc. | ×1.25 | µL |
|---|---|---|---|---|---|---|
| BKV amplification primer | 13 | µM | 153.28 | 0.60 | 0.75 | 16.88 |
| BKV amplification primer | 14 | µM | 165.56 | 0.60 | 0.75 | 15.63 |
| BKV probe oligonucleotide | 15 | µM | 126.06 | 0.40 | 0.50 | 13.68 |
| IC amplification primer | 53 | µM | 166.50 | 0.60 | 0.75 | 15.54 |
| IC amplification primer | 54 | µM | 238.70 | 0.60 | 0.75 | 10.84 |
| IC Probe oligonucleotide | 55 | µM | 111.50 | 0.40 | 0.50 | 15.47 |
| Tris, pH 8.0 | | mM | 1000.00 | 4.00 | 5.00 | 17.25 |
| $MgCl_2$ | | mM | 1000.00 | 4.00 | 5.00 | 17.25 |
| KCl | | mM | 2000.00 | 65.00 | 81.25 | 140.16 |
| Water | | | | | | 3187.30 |
| Total: | | | | | | 3450.00 |

TABLE 5-9

Oligonucleotide descriptions.

| SEQ ID NO. | Sequence 5' → 3' | Modifications | MW Without Modifications | MW With Modifications | OD | Conc. (µM) |
|---|---|---|---|---|---|---|
| 13 | CCCTACTTGAGCCAARGAACTAA | | 6993.56 | 6993.56 | 26.8 | 153.28 |
| 14 | GGCCTAACWCCTCAAACATATGC | | 6957.02 | 7055.02 | 29.2 | 165.56 |
| 15 | TTAAAGCAGCAAACCCAGCAATAGCC | 610, 3' BHQ2 | 7926.18 | 9233.37 | 29.1 | 126.06 |

TABLE 5-10

Results: Average and Standard Deviation for Ct, RFU, TSlope and Estimated Background.

| Fluorophore | Condition | Count | Positivity | AVG CT | SD CT | AVG RFU | SD RFU | AVG TS | SD TS | AVG EB | SD EB | Delta Ct 0.5 LoG | Delta Ct 1.0 LoG |
|---|---|---|---|---|---|---|---|---|---|---|---|---|---|
| ROX | 3.16 cpr | 10 | 48% | 39.23 | 0.52 | 3017 | 2297 | 306 | 29 | 1135 | 103 | 0.68 | 2.55 |
| ROX | 10 cpr | 20 | 95% | 38.54 | 0.95 | 4895 | 1809 | 293 | 44 | 1113 | 147 | 1.87 | 3.75 |
| ROX | 31.6 cpr | 21 | 100% | 36.68 | 0.66 | 7015 | 1253 | 302 | 43 | 1122 | 139 | 1.88 | n/a |
| ROX | 100 cpr | 21 | 100% | 34.80 | 0.39 | 9007 | 1237 | 320 | 56 | 1213 | 156 | 1.79 | n/a |
| ROX | BK Pos Ctrl | 3 | 100% | 33.01 | 0.24 | 10882 | 988 | 334 | 58 | 1274 | 126 | n/a | n/a |
| ROX | Plasma Ctrl | 0 | 0% | n/a | n/a | 14 | 8 | n/a | n/a | 1102 | 39 | n/a | n/a |
| ROX | STM Ctrl | 0 | 0% | n/a | n/a | 13 | 1 | n/a | n/a | 1195 | 29 | n/a | n/a |
| RED677 | 3.16 cpr | 21 | 100% | 27.81 | 0.19 | 9469 | 1115 | 311 | 61 | 3196 | 391 | n/a | n/a |
| RED677 | 10 cpr | 21 | 100% | 27.84 | 0.30 | 9172 | 1478 | 303 | 48 | 3083 | 469 | n/a | n/a |
| RED677 | 31.6 cpr | 21 | 100% | 27.71 | 0.45 | 9242 | 1341 | 310 | 54 | 3120 | 430 | n/a | n/a |
| RED677 | 100 cpr | 21 | 100% | 27.45 | 0.26 | 10140 | 1653 | 319 | 41 | 3409 | 595 | n/a | n/a |
| RED677 | BK Pos Ctrl | 3 | 100% | 26.30 | 0.16 | 9609 | 924 | 354 | 37 | 3373 | 336 | n/a | n/a |
| RED677 | Plasma Ctrl | 3 | 100% | 27.41 | 0.10 | 8734 | 483 | 329 | 18 | 3053 | 161 | n/a | n/a |
| RED677 | STM Ctrl | 3 | 100% | 26.24 | 0.15 | 9867 | 718 | 375 | 32 | 3370 | 185 | n/a | n/a |

20 out of 21 PCR reps were detected at 10 copies per reaction for BK virus in plasma.

TABLE 5-11

BKV Analytical Sensitivity in Plasma

| Copies / reaction | Copies/ mL | Reactivity | Average Ct | St. Dev. Ct | Average RFU | St. Dev. RFU | Average Background RFU | St. Dev. Background RFU | Average Slope at Threshold | St. Dev. Slope at Threshold |
|---|---|---|---|---|---|---|---|---|---|---|
| 3.16 | 87.8 | 10/21 | 39.07 | 0.52 | 4577.60 | 831.12 | 1135.29 | 103.33 | 294.70 | 37.34 |
| 10 | 277.8 | 20/21 | 38.38 | 0.95 | 5198.30 | 1463.74 | 1113.38 | 147.21 | 266.40 | 45.27 |
| 31.6 | 878.4 | 21/21 | 36.49 | 0.67 | 7085.67 | 1266.00 | 1122.05 | 139.33 | 289.76 | 37.07 |
| 100 | 2777.8 | 21/21 | 34.61 | 0.37 | 9084.38 | 1242.25 | 1213.10 | 156.10 | 276.38 | 45.17 |

TABLE 5-12

BK Virus and Plasmid Linearity Results

| Copies/ reaction | Reactivity* | Avg Ct | Standard Deviation of Ct | Avg RFU | Standard Deviation of RFU | Avg Background RFU | Standard Deviation of Background RFU | Average Slope at Threshold | Standard Deviation of Slope at Threshold |
|---|---|---|---|---|---|---|---|---|---|
| BK Virus in Culture Fluid | | | | | | | | | |
| 10 | 6/6 | 35.64 | 0.43 | 12288.44 | 1511.04 | 2369.23 | 179.19 | 344.44 | 64.60 |
| 100 | 6/6 | 31.95 | 0.39 | 14362.64 | 938.16 | 2173.58 | 93.73 | 343.23 | 60.60 |
| 1000 | 6/6 | 28.87 | 0.14 | 14674.10 | 859.45 | 2065.00 | 107.39 | 311.44 | 71.62 |
| 10000 | 6/6 | 25.26 | 0.19 | 14510.42 | 632.67 | 1900.22 | 75.32 | 330.84 | 21.43 |
| 100000 | 6/6 | 21.74 | 0.07 | 15671.69 | 897.05 | 1904.23 | 122.63 | 244.06 | 6.53 |
| 1000000 | 6/6 | 18.50 | 0.11 | 14378.85 | 459.21 | 1786.68 | 82.24 | 289.06 | 18.49 |
| BK Plasmid | | | | | | | | | |
| 10 | 6/6 | 37.10 | 1.14 | 9892.52 | 2010.28 | 2201.01 | 238.76 | 318.25 | 75.26 |
| 100 | 6/6 | 33.16 | 0.22 | 13049.79 | 1025.44 | 2078.22 | 278.76 | 317.72 | 69.69 |
| 1000 | 6/6 | 29.87 | 0.09 | 14400.39 | 513.24 | 2025.06 | 96.88 | 282.32 | 64.51 |
| 10000 | 6/6 | 26.38 | 0.24 | 15042.12 | 1758.95 | 2085.78 | 218.49 | 328.62 | 47.29 |
| 100000 | 6/6 | 22.81 | 0.13 | 15589.84 | 1120.75 | 2060.33 | 143.53 | 267.43 | 56.05 |
| 1000000 | 6/6 | 19.47 | 0.06 | 15254.72 | 773.24 | 2015.97 | 119.87 | 297.00 | 13.95 |

*Reactivity defined as an amplification curve crossing a threshold of 500 RFU

Conclusion: Evaluation of results the BKV oligonucleotides were effective in detecting at least as low as 10 copies of BVK per reaction. 95% detection was observed for BKV spiked in plasma at 10 copies/reaction (277.8 copies/mL). Internal control was detected at 100% in both studies Example 6. BK Limit of Detection in Urine The limit of detection of BK virus with in urine using the BK VP2 amplification primer set was determined. PPR for BK and DNA IC detection was prepared according to the Table 6-1. BK Virus in urine was evaluated for reactivity with a PCR formulation. BK virus in culture fluid was spiked into each matrix at the indicated concentrations. The samples in urine were diluted 1:1 with UTM containing 3 mg/mL PK and 10× K18 TCO. All samples were processed using the Wave 1 sequence file.

TABLE 6-1

BK + DNA IC PPR

| Reagent Name | stock conc. | Units | conc. in PRC (1X) | Conc. in recon (1.25X) | Volume (µL) |
|---|---|---|---|---|---|
| Water | n/a | n/a |  | n/a | 3191.3 |
| Tris pH 8 | 1000 | Mm |  | 5 | 17.3 |
| SEQ ID NO: 13 | 153.28 | µM | 0.60 | 0.75 | 16.9 |
| SEQ ID NO: 14 | 165.56 | µM | 0.60 | 0.75 | 15.6 |
| SEQ ID NO: 15 | 126.06 | µM | 0.4 | 0.5 | 13.7 |
| KCl | 2000 | mM | 65 | 81.25 | 140.2 |
| MgCl$_2$ | 1000 | mM | 4 | 5 | 17.3 |
| SEQ ID NO: 53 | 223.29 | µM | 0.6 | 0.75 | 11.6 |
| SEQ ID NO: 54 | 238.68 | µM | 0.6 | 0.75 | 10.8 |
| SEQ ID NO: 55 | 111.54 | µM | 0.4 | 0.5 | 15.5 |
| Final Volume |  |  |  |  | 3450 |

3 PPR tubes will have 1100 µl added to Recon tube and 400 µl of oil added to top.

A BK negative pool of urine was made to spike BK viral lysate into. 12 mL of urine was made by pooling 3 mL each of urine samples IH_1, IH_6, IH_7, IH_8 and IH_14. Various levels of BK viral lysate were then spiked in urine samples. Serial dilutions were prepped for a final dilution of 100, 31.62, 10, 3.16 cp/rxn of virus in urine which is equivalent to 55.6 cp/µl of virus in urine.

TABLE 6-2

| start conc. (cp/µL) | final BK conc. (cp/µL) | start vol (µL) | µL of Diluent | final vol (µL) | Diluent |
|---|---|---|---|---|---|
| 1.00 × 10$^6$ | 1.00 × 10$^5$ | 10.0 | 90.0 | 100 | water |
| 1.00 × 10$^5$ | 1.00 × 10$^4$ | 10.0 | 90.0 | 100 | water |
| 1.00 × 10$^4$ | 1.00 × 10$^3$ | 20.0 | 180.0 | 200 | water |
| 1.00 × 10$^3$ | 200 | 100.0 | 400.0 | 500 | UTM |
| 1.00 × 10$^3$ | 100 | 30.0 | 270.0 | 300 | water |
| 100 | 5.6 | 241.7 | 4108.3 | 4350 | Urine Pool |
| 5.56 | 1.76 | 1344.0 | 2906.0 | 4250 | Urine Pool |
| 1.76 | 0.56 | 1249.1 | 2700.9 | 3950 | Urine Pool |
| 0.556 | 0.18 | 948.7 | 2051.3 | 3000 | Urine Pool |

850 µL of the final dilution was added into sample tubes containing 850 µL of diluent, 3× for each final urine concentration. 300 µL of the 200 cp/rxn was added to a single tube containing diluent for the positive control to give 3600 cp/rxn. UTM+10×TCO was added to each tube first, followed by the sample (either urine or UTM). A BK positive control tube was run as an additional control.

TABLE 6-3

| Sample | # Tubes | µL UTM + 10 × TCO | µL BK Spike | µL UTM | Negative Urine Pool |
|---|---|---|---|---|---|
| BK Spiked in Urine Neg Pool: 100 cp/rxn | 3 | 850 | 850 | 0 | 0 |
| BK Spiked in Urine Neg Pool: 31.62 cp/rxn | 3 | 850 | 850 | 0 | 0 |
| BK Spiked in Urine Neg Pool: 10 cp/rxn | 3 | 850 | 850 | 0 | 0 |
| BK Spiked in Urine Neg Pool: 3.16 cp/rxn | 3 | 850 | 850 | 0 | 0 |
| Pos Ctrl: BK CF in UTM diluted with UTM 10X TCO 100 cp/rxn[a] | 1 | 300 | 300 | 0 | 0 |
| Neg Ctrl: UTM: UTM 10X TCO (diluent) | 1 | 300 | 0 | 300 | 0 |
| Pool Screen: Urine Pool: UTM 10X TCO | 1 | 300 | 0 | 0 | 300 |

[a] 3600 cp/rxn

Sample tubes were loaded on a Panther Fusion system and tested with the default DNA thermal cycling program. The number of tubes, extractions and replicates per sample is given in the table below:

TABLE 6-4

| Sample Types | # Sample tubes | # extractions per tube | # PCR replicates per extraction | Total replicates |
|---|---|---|---|---|
| BK Spiked in Urine Neg Pool: 100 cp/rxn | 3 | 2, 3 (for 1 tube) | 3 | 21 |
| BK Spiked in Urine Neg Pool: 31.62 cp/rxn | 3 | 2, 3 (for 1 tube) | 3 | 21 |
| BK Spiked in Urine Neg Pool: 10 cp/rxn | 3 | 2, 3 (for 1 tube) | 3 | 21 |
| BK Spiked in Urine Neg Pool: 3.16 cp/rxn | 3 | 2, 3 (for 1 tube) | 3 | 21 |
| Pos Ctrl: BK CF in UTM diluted with UTM 10X TCO 3600 cp/rxn | 1 | 1 | 3 | 3 |
| Pos Ctrl: BK CF in STM (no diluent, no TCO) 100 cp/rxn | 1 | 1 | 3 | 3 |
| Neg Ctrl: UTM: UTM 10X TCO (diluent). | 1 | 1 | 3 | 3 |
| Pool Screen: Urine Pool: UTM 10X TCO | 1 | 1 | 3 | 3 |

TABLE 6-5

BKV oligonucleotide information.

| SEQ ID NO. | Sequence 5' → 3' | Modifications | OD | Conc. (µM) |
|---|---|---|---|---|
| 13 | CCCTACTTGAGCCAARGAACTAA | | 26.8 | 153.28 |
| 14 | GGCCTAACWCCTCAAACATATGC | | 29.2 | 165.56 |
| 15 | TTAAAGCAGCAAACCCAGCAATAGCC | CalRed610, 3' BHQ2 | 29.1 | 126.06 |

TABLE 6-6

DNA IC oligonucleotide information.

| Target | SEQ ID NO. | Sequence 5' → 3' | Modifications | OD | Conc. (µM) |
|---|---|---|---|---|---|
| GIC plasmid | 53 | ATGGTCAATTAGAGACAAAG | | 34.6 | 223.3 |
| GIC plasmid | 54 | CGTTCACTATTGGTCTCTGC | | 36.1 | 238.7 |
| GIC plasmid | 55 | CGGAATCACAAGTCAATCATCGCGCA | 5' Q705 and 3' BHQ2 | 25.58 | 111.5 |

TABLE 6-7

| Target | Oligo name | Sequence 5' → 3' | Modifications | Conc. (mg/mL) |
|---|---|---|---|---|
| TCO | 2'Ome K18_3'Bkd K18, 3T, 30A | | 3' dC (Ac) | 2.46 |

TABLE 6-8

Preparation of 10X TCO in UTM.

| stock TCO conc. (mg/mL) | stock TCO conc. (mg/µL) | Vol TCO (µL) | TCO conc. in diluent (mg/µL) | Vol diluent needed (mg/µL) | µL of UTM |
|---|---|---|---|---|---|
| 2.46 | 0.00246 | 95.0 | $1.66667 \times 10^{-5}$ | 14025 | 13930.0 |

TABLE 6-9

BK detection in ROX channel and ID detection in RED677

| Sample ID | Count Ct | Positivity | Average Ct | StdDev Ct | Average Tslope | StdDev Tslope | Average Background | StdDev Background | Average RFU Range | StdDev RFU Range |
|---|---|---|---|---|---|---|---|---|---|---|
| Negative UTM | 0/3 | 0% | | | | | 1239.2 | 67.5 | 113.6 | 9.5 |
| Negative Urine | 0/3 | 0% | | | | | 1229.0 | 137.4 | 105.1 | 16.2 |
| BK Pos Ctrl 100 cpSTM | 3/3 | 100% | 32.3 | 0.2 | 303.1 | 39.4 | 1358.0 | 131.0 | 11997.4 | 992.5 |

TABLE 6-9-continued

BK detection in ROX channel and ID detection in RED677

| Sample ID | Count Ct | Positivity | Average Ct | StdDev Ct | Average Tslope | StdDev Tslope | Average Background | StdDev Background | Average RFU Range | StdDev RFU Range |
|---|---|---|---|---|---|---|---|---|---|---|
| BK3600 cp UTM | 3/3 | 100% | 27.9 | 0.1 | 274.6 | 77.6 | 1304.7 | 64.2 | 11886.9 | 457.1 |
| BK100 cp Urine | 21/21 | 100% | 33.6 | 0.3 | 270.5 | 37.2 | 1348.5 | 78.0 | 11119.2 | 902.6 |
| BK31.62 cp Urine | 21/21 | 100% | 35.2 | 0.5 | 281.9 | 44.4 | 1336.3 | 113.1 | 9699.1 | 1089.5 |
| BK10 cp Urine | 20/21 | 95% | 37.5 | 1.0 | 270.5 | 44.8 | 1332.1 | 101.4 | 6887.5 | 2227.5 |
| BK3.16 cp Urine | 15/21 | 71% | 38.9 | 0.8 | 294.2 | 57.3 | 1341.7 | 86.4 | 3747.9 | 2568.3 |

TABLE 6-10

IC Detection in RED677 Channel

| Sample ID | Count Ct | Positivity | Average Ct | StdDev Ct | Average Tslope | StdDev Tslope | Average Background | StdDev Background | Average RFU Range | StdDev RFU Range |
|---|---|---|---|---|---|---|---|---|---|---|
| Negative UTM | 3/3 | 100% | 27.4 | 0.1 | 321.4 | 18.3 | 1785.0 | 105.1 | 5040.5 | 295.0 |
| Negative Urine | 3/3 | 100% | 27.9 | 0.2 | 347.8 | 69.8 | 1884.9 | 180.4 | 5255.3 | 530.0 |
| BK P05 Ctrl 100 cpSTM | 3/3 | 100% | 26.8 | 0.4 | 304.2 | 21.1 | 2474.3 | 610.5 | 6874.6 | 1701.3 |
| BK3600 cp UTM | 3/3 | 100% | 27.3 | 0.1 | 349.1 | 12.5 | 1933.0 | 81.5 | 5328.2 | 131.3 |
| BK100 cp Urine | 21/21 | 100% | 27.2 | 0.1 | 373.1 | 26.9 | 2626.0 | 111.3 | 7383.6 | 314.1 |
| BK31.62 cp Urine | 21/21 | 100% | 27.5 | 0.3 | 310.4 | 60.8 | 2357.3 | 460.0 | 6657.4 | 1252.0 |
| BK10 cp Urine | 21/21 | 100% | 27.7 | 0.3 | 292.7 | 56.4 | 2211.8 | 327.1 | 6193.9 | 892.4 |
| BK3.16 cp Urine | 21/21 | 100% | 27.4 | 0.1 | 343.0 | 24.7 | 2550.9 | 147.2 | 6903.2 | 443.3 |

TABLE 6-11

BKV Analytical Sensitivity in urine

| Copies/ reaction | Copies/ mL | Reactivity | Average Ct | St. Dev. Ct | Average RFU | St. Dev. RFU | Average Background RFU | St. Dev. Background RFU | Average Slope at Threshold | St. Dev. Slope at Threshold |
|---|---|---|---|---|---|---|---|---|---|---|
| 3.16 | 87.8 | 15/21 | 39.04 | 0.86 | 5174.60 | 1121.40 | 1341.67 | 86.49 | 332.93 | 39.01 |
| 10 | 277.8 | 20/21 | 37.72 | 1.03 | 7143.10 | 1624.81 | 1332.10 | 101.46 | 320.25 | 43.50 |
| 31.6 | 878.4 | 21/21 | 35.48 | 0.53 | 9603.62 | 1085.44 | 1336.33 | 113.20 | 319.14 | 54.08 |
| 100 | 2777.8 | 21/21 | 33.86 | 0.27 | 11012.05 | 900.68 | 1348.43 | 77.90 | 307.86 | 55.27 |

TABLE 6-12

95% BK detection was observed at 10 cp/rxn.

| Sample ID | Count Ct | Positivity | Average Ct |
|---|---|---|---|
| Negative UTM | 0/3 | 0% | |
| Negative Urine | 0/3 | 0% | |
| BK Pos Ctrl 100 cpSTM | 3/3 | 100% | 32.3 |
| BK3600 cp UTM | 3/3 | 100% | 27.9 |
| BK100 cp Urine | 21/21 | 100% | 33.6 |
| BK31.62 cp Urine | 21/21 | 100% | 35.2 |
| BK10 cp Urine | 20/21 | 95% | 37.5 |
| BK3.16 cp Urine | 15/21 | 71% | 38.9 |

Conclusion: BKV oligonucleotides were effective in detecting at least as low as 10 copies of BVK in urine per reaction (277.8 copies/mL) with 95% positivity. Internal control was detected at 100% in both studies.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise.

What is claimed is:

1. A combination of oligonucleotides for amplifying a BK polyomavirus (BKV) nucleic acid sequence comprising:
   a) one or more first amplification primers wherein each first amplification primer is 18-30 nucleobases in length and comprises a nucleotide sequence having at least 90% identity to the nucleotide sequence of: SEQ ID NO:25, and
   b) one or more second amplification primers wherein each second amplification primer is 19-30 nucleobases in length and comprises a nucleotide sequence having at least 90% identity to the nucleotide sequence of: SEQ ID NO:26.

2. The combination of claim 1, wherein the first amplification primer and/or the second amplification primer contains one or more modified nucleotides independently selected from the group consisting of: a 2'-O-methyl modified nucleotide, a 2'-fluoro modified nucleotide, and a 5-methyl-2'-deoxycytosine.

3. The combination of claim 1, wherein every cytosine in the first amplification primer and/or the second amplification primer except for a 3' terminal cytosine, if present, is a 5-methyl-2'-deoxycytosine.

4. The combination of claim 1, wherein:
   a) the nucleotide sequence of each of the one or more first amplification primers consists of the nucleotide sequence of SEQ ID NO:25, and
   b) the nucleotide sequence each of the one or more second amplification primers consists of the nucleotide sequence of: SEQ ID NO:26.

5. The combination of claim 1, wherein: the first amplification primer comprises the nucleotide sequence of SEQ ID NO:25 and the one or more second amplification primers comprise at least one amplification primer comprising the nucleotide sequence of SEQ ID NO: 48 and at least one amplification primer comprising the nucleotide sequence of SEQ ID NO:49.

6. The combination of claim 1, further comprising a probe oligonucleotide for detecting an amplified BKV nucleic acid sequence wherein the probe oligonucleotide is 21-30 nucleobases in length and comprises a nucleotide sequence having at least 90% identity to the nucleotide sequence selected from the group consisting of: SEQ ID NO:27, and wherein the probe oligonucleotide is attached to at least one detectable label.

7. The combination of claim 6, wherein the probe oligonucleotide contains one or more modified nucleotides independently selected from the group consisting of: a 2'-O-methyl modified nucleotide, a 2'-fluoro modified nucleotide, or a 5-methyl-2'-deoxycytosine.

8. The combination of claim 7, wherein the probe oligonucleotide contains 2, 3, 4, 5, 6, 7, or 8 5-methyl-2'-deoxycytosines.

9. The combination of claim 8, wherein every cytosine in the probe oligonucleotide is a 5-methyl-2'-deoxycytosine.

10. The combination of claim 6 wherein the nucleotide sequence of the probe oligonucleotide consists of the nucleotide sequence selected from the group consisting of SEQ ID NO:27.

11. The combination of claim 6, wherein the detectable label contains a fluorescent molecule attached at the 5' or 3' end of the probe oligonucleotide or a fluorescent molecule attached at the 5' end of the probe oligonucleotide and a quencher is attached at the 3' end of the probe oligonucleotide.

12. The combination of claim 11 wherein the probe oligonucleotide is a hydrolysis probe.

13. A kit for amplifying a BKV nucleic acid sequence comprising: the amplification primers of claim 1 or the amplification primers of claim 1 and the probe oligonucleotide of claim 6, wherein the amplification primers and the probe oligonucleotide are provided in a single container or separate containers.

14. The kit of claim 13, further comprising at least one reaction mixture wherein the at least one reaction mixture comprises one or more of: DNA polymerase, deoxyribonucleotides, ribonucleotides, positive control nucleic acid, negative control nucleic acid, internal control nucleic acid, control amplification primers, control probe oligonucleotide, KCl, $MgCl_2$, potassium acetate, buffer, BSA, sucrose, trehalose, DMSO, betaine, formamide, glycerol, polyethylene glycol, non-ionic detergents, ammonium ions, and EDTA.

15. The kit of claim 13, further comprising instructions for use.

16. A method of amplifying a BKV nucleic acid sequence comprising: contacting a sample containing or suspected of containing the BKV nucleic acid sequence with the combination of claim 1 and performing a nucleic acid amplification reaction, wherein the BKV nucleic acid sequence, if present in the sample, is amplified by the amplification primers to produce a BKV amplicon.

17. The method of claim 16, wherein the nucleic acid amplification reaction comprises polymerase chain reaction (PCR).

18. The method of claim 17, wherein the method further comprises contacting the sample with the probe oligonucleotide of claim 7, thereby detecting the presence of absence of the BKV amplicon.

19. A method of claim 18, wherein the method further comprises quantifying the amount of the BKV nucleic acid sequence or BKV amplicon, if present, in the sample.

20. The method of claim 19, wherein the BKV nucleic acid sequence or BKV amplicon is detected and/or quantified in real time.

* * * * *

SEQUENCE LISTING

```
Sequence total quantity: 55
SEQ ID NO: 1                moltype = DNA   length = 27
FEATURE                     Location/Qualifiers
misc_feature                1..27
                            note = synthetic oligonucleotide
source                      1..27
                            mol_type = other DNA
                            organism = synthetic construct
SEQUENCE: 1
ctagaacttc tactcctcct tttatta                                            27

SEQ ID NO: 2                moltype = DNA   length = 21
FEATURE                     Location/Qualifiers
misc_feature                1..21
                            note = synthetic oligonucleotide
source                      1..21
                            mol_type = other DNA
                            organism = synthetic construct
SEQUENCE: 2
ggccccaacm aaaagaaaag g                                                  21

SEQ ID NO: 3                moltype = DNA   length = 24
FEATURE                     Location/Qualifiers
misc_feature                1..24
                            note = synthetic oligonucleotide
source                      1..24
                            mol_type = other DNA
                            organism = synthetic construct
SEQUENCE: 3
ggcttttgg gagctgcccc tgga                                                24

SEQ ID NO: 4                moltype = DNA   length = 20
FEATURE                     Location/Qualifiers
misc_feature                1..20
                            note = synthetic oligonucleotide
source                      1..20
                            mol_type = other DNA
                            organism = synthetic construct
SEQUENCE: 4
gcagcaaacc cagcaatagc                                                    20

SEQ ID NO: 5                moltype = DNA   length = 24
FEATURE                     Location/Qualifiers
misc_feature                1..24
                            note = synthetic oligonucleotide
source                      1..24
                            mol_type = other DNA
                            organism = synthetic construct
SEQUENCE: 5
ccttgctact gtagagggca taac                                               24

SEQ ID NO: 6                moltype = DNA   length = 30
FEATURE                     Location/Qualifiers
misc_feature                1..30
                            note = synthetic oligonucleotide
source                      1..30
                            mol_type = other DNA
                            organism = synthetic construct
SEQUENCE: 6
agcaccagca attacagcat atgtttgagg                                         30

SEQ ID NO: 7                moltype = DNA   length = 26
FEATURE                     Location/Qualifiers
misc_feature                1..26
                            note = synthetic oligonucleotide
source                      1..26
                            mol_type = other DNA
                            organism = synthetic construct
SEQUENCE: 7
gactctgtaa aagactccta ggtaag                                             26

SEQ ID NO: 8                moltype = DNA   length = 26
FEATURE                     Location/Qualifiers
misc_feature                1..26
                            note = synthetic oligonucleotide
source                      1..26
                            mol_type = other DNA
                            organism = synthetic construct
```

```
SEQUENCE: 8
atgggtgctg ctctagcact tttggg                                              26

SEQ ID NO: 9              moltype = DNA   length = 23
FEATURE                   Location/Qualifiers
misc_feature              1..23
                          note = synthetic oligonucleotide
source                    1..23
                          mol_type = other DNA
                          organism = synthetic construct
SEQUENCE: 9
gcagcagcct cagatacact ggc                                                 23

SEQ ID NO: 10             moltype = DNA   length = 23
FEATURE                   Location/Qualifiers
misc_feature              1..23
                          note = synthetic oligonucleotide
source                    1..23
                          mol_type = other DNA
                          organism = synthetic construct
SEQUENCE: 10
ttagttcytt ggctcaagta ggg                                                 23

SEQ ID NO: 11             moltype = DNA   length = 29
FEATURE                   Location/Qualifiers
misc_feature              1..29
                          note = synthetic oligonucleotide
source                    1..29
                          mol_type = other DNA
                          organism = synthetic construct
SEQUENCE: 11
attgggatca caaagtttcc actgtaggc                                           29

SEQ ID NO: 12             moltype = DNA   length = 26
FEATURE                   Location/Qualifiers
misc_feature              1..26
                          note = synthetic oligonucleotide
source                    1..26
                          mol_type = other DNA
                          organism = synthetic construct
SEQUENCE: 12
gggttaaaca attccaawgc catgcc                                              26

SEQ ID NO: 13             moltype = DNA   length = 23
FEATURE                   Location/Qualifiers
misc_feature              1..23
                          note = synthetic oligonucleotide
source                    1..23
                          mol_type = other DNA
                          organism = synthetic construct
SEQUENCE: 13
ccctacttga gccaargaac taa                                                 23

SEQ ID NO: 14             moltype = DNA   length = 23
FEATURE                   Location/Qualifiers
misc_feature              1..23
                          note = synthetic oligonucleotide
source                    1..23
                          mol_type = other DNA
                          organism = synthetic construct
SEQUENCE: 14
ggcctaacwc ctcaaacata tgc                                                 23

SEQ ID NO: 15             moltype = DNA   length = 26
FEATURE                   Location/Qualifiers
misc_feature              1..26
                          note = synthetic oligonucleotide
source                    1..26
                          mol_type = other DNA
                          organism = synthetic construct
SEQUENCE: 15
ttaaagcagc aaacccagca atagcc                                              26

SEQ ID NO: 16             moltype = DNA   length = 20
FEATURE                   Location/Qualifiers
misc_feature              1..20
                          note = synthetic oligonucleotide
source                    1..20
                          mol_type = other DNA
```

```
                        organism = synthetic construct
SEQUENCE: 16
ccttttctttt tkgttggggc                                              20

SEQ ID NO: 17           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 17
acagtcccgt acaggcctag aag                                           23

SEQ ID NO: 18           moltype = DNA  length = 24
FEATURE                 Location/Qualifiers
misc_feature            1..24
                        note = synthetic oligonucleotide
source                  1..24
                        mol_type = other DNA
                        organism = synthetic construct
SEQUENCE: 18
aaaactattg ccccaggagg tgct                                          24

SEQ ID NO: 19           moltype = DNA  length = 25
FEATURE                 Location/Qualifiers
misc_feature            1..25
                        note = synthetic oligonucleotide
source                  1..25
                        mol_type = other DNA
                        organism = synthetic construct
SEQUENCE: 19
ttagttcytt ggctcaagta gggta                                         25

SEQ ID NO: 20           moltype = DNA  length = 29
FEATURE                 Location/Qualifiers
misc_feature            1..29
                        note = synthetic oligonucleotide
source                  1..29
                        mol_type = other DNA
                        organism = synthetic construct
SEQUENCE: 20
gcctacagtg gaaactttgt gatcccaat                                     29

SEQ ID NO: 21           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 21
gggttaaaca attccaawgc cat                                           23

SEQ ID NO: 22           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 22
ccctacttga gccaargaac taa                                           23

SEQ ID NO: 23           moltype = DNA  length = 26
FEATURE                 Location/Qualifiers
misc_feature            1..26
                        note = synthetic oligonucleotide
source                  1..26
                        mol_type = other DNA
                        organism = synthetic construct
SEQUENCE: 23
ggctattgct gggtttgctg cttaa                                         26

SEQ ID NO: 24           moltype = DNA  length = 23
FEATURE                 Location/Qualifiers
misc_feature            1..23
                        note = synthetic oligonucleotide
source                  1..23
```

```
                        mol_type = other DNA
                        organism = synthetic construct
SEQUENCE: 24
ggcctaacwc ctcaaacata tgc                                          23

SEQ ID NO: 25           moltype = DNA   length = 20
FEATURE                 Location/Qualifiers
misc_feature            1..20
                        note = synthetic oligonucleotide
source                  1..20
                        mol_type = other DNA
                        organism = synthetic construct
SEQUENCE: 25
gaaagagctg cctggggaaa                                              20

SEQ ID NO: 26           moltype = DNA   length = 24
FEATURE                 Location/Qualifiers
misc_feature            1..24
                        note = synthetic oligonucleotide
source                  1..24
                        mol_type = other DNA
                        organism = synthetic construct
SEQUENCE: 26
ctacctttac atcytgctcc attt                                         24

SEQ ID NO: 27           moltype = DNA   length = 29
FEATURE                 Location/Qualifiers
misc_feature            1..29
                        note = synthetic oligonucleotide
source                  1..29
                        mol_type = other DNA
                        organism = synthetic construct
SEQUENCE: 27
ccctgacaaa gggggcgacg aggataaaa                                    29

SEQ ID NO: 28           moltype = DNA   length = 21
FEATURE                 Location/Qualifiers
misc_feature            1..21
                        note = synthetic oligonucleotide
source                  1..21
                        mol_type = other DNA
                        organism = synthetic construct
SEQUENCE: 28
ggccccaaca aaagaaaag g                                             21

SEQ ID NO: 29           moltype = DNA   length = 21
FEATURE                 Location/Qualifiers
misc_feature            1..21
                        note = synthetic oligonucleotide
source                  1..21
                        mol_type = other DNA
                        organism = synthetic construct
SEQUENCE: 29
ggccccaacc aaagaaaag g                                             21

SEQ ID NO: 30           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 30
ttagttcttt ggctcaagta ggg                                          23

SEQ ID NO: 31           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 31
ttagttcctt ggctcaagta ggg                                          23

SEQ ID NO: 32           moltype = DNA   length = 26
FEATURE                 Location/Qualifiers
misc_feature            1..26
                        note = synthetic oligonucleotide
```

```
source                  1..26
                        mol_type = other DNA
                        organism = synthetic construct
SEQUENCE: 32
gggttaaaca attccaaagc catgcc                                               26

SEQ ID NO: 33           moltype = DNA   length = 26
FEATURE                 Location/Qualifiers
misc_feature            1..26
                        note = synthetic oligonucleotide
source                  1..26
                        mol_type = other DNA
                        organism = synthetic construct
SEQUENCE: 33
gggttaaaca attccaatgc catgcc                                               26

SEQ ID NO: 34           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 34
ccctacttga gccaaggaac taa                                                  23

SEQ ID NO: 35           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 35
ccctacttga gccaaagaac taa                                                  23

SEQ ID NO: 36           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 36
ggcctaacac ctcaaacata tgc                                                  23

SEQ ID NO: 37           moltype = DNA   length = 23
FEATURE                 Location/Qualifiers
misc_feature            1..23
                        note = synthetic oligonucleotide
source                  1..23
                        mol_type = other DNA
                        organism = synthetic construct
SEQUENCE: 37
ggcctaactc ctcaaacata tgc                                                  23

SEQ ID NO: 38           moltype = DNA   length = 20
FEATURE                 Location/Qualifiers
misc_feature            1..20
                        note = synthetic oligonucleotide
source                  1..20
                        mol_type = other DNA
                        organism = synthetic construct
SEQUENCE: 38
cctttctctt tggttggggc                                                      20

SEQ ID NO: 39           moltype = DNA   length = 20
FEATURE                 Location/Qualifiers
misc_feature            1..20
                        note = synthetic oligonucleotide
source                  1..20
                        mol_type = other DNA
                        organism = synthetic construct
SEQUENCE: 39
cctttctctt ttgttggggc                                                      20

SEQ ID NO: 40           moltype = DNA   length = 25
FEATURE                 Location/Qualifiers
misc_feature            1..25
```

```
                        note = synthetic oligonucleotide
source                  1..25
                        mol_type = other DNA
                        organism = synthetic construct
SEQUENCE: 40
ttagttctttt ggctcaagta gggta                                           25

SEQ ID NO: 41           moltype = DNA  length = 25
FEATURE                 Location/Qualifiers
misc_feature            1..25
                        note = synthetic oligonucleotide
source                  1..25
                        mol_type = other DNA
                        organism = synthetic construct
SEQUENCE: 41
ttagttcctt ggctcaagta gggta                                            25

SEQ ID NO: 42           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 42
gggttaaaca attccaaagc cat                                              23

SEQ ID NO: 43           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 43
gggttaaaca attccaatgc cat                                              23

SEQ ID NO: 44           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 44
ccctacttga gccaaggaac taa                                              23

SEQ ID NO: 45           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 45
ccctacttga gccaaraaac taa                                              23

SEQ ID NO: 46           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 46
ggcctaacac ctcaaacata tgc                                              23

SEQ ID NO: 47           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 47
ggcctaactc ctcaaacata tgc                                              23

SEQ ID NO: 48           moltype = DNA  length = 24
FEATURE                 Location/Qualifiers
```

```
misc_feature           1..24
                       note = synthetic oligonucleotide
source                 1..24
                       mol_type = other DNA
                       organism = synthetic construct
SEQUENCE: 48
ctacctttac atcttgctcc attt                                              24

SEQ ID NO: 49          moltype = DNA  length = 24
FEATURE                Location/Qualifiers
misc_feature           1..24
                       note = synthetic oligonucleotide
source                 1..24
                       mol_type = other DNA
                       organism = synthetic construct
SEQUENCE: 49
ctacctttac atcctgctcc attt                                              24

SEQ ID NO: 50          moltype = DNA  length = 5147
FEATURE                Location/Qualifiers
source                 1..5147
                       mol_type = genomic DNA
                       organism = Polyoma BK virus
SEQUENCE: 50
gcctcggcct cttatatatt ataaaaaaaa aggccacagg gaggagctgc tttcccatgg        60
aatgcagcca aaccatgacc tcaggaagga aagtgcagca ctgggcagcc agccagtggc       120
agttaatagt gaaaccccgc ccctagaatt ctcaaataaa cacaagagga agtgaaagt        180
agccaaagga gtgaaagca gccagacaga catgttttgc gagccgagga atcttggcct       240
tgtcccagt taatactgga caaaggccat ggttctacgc cagctgtcac gacaagcttc       300
tgtgaaagtt agtaaaacct ggactggaac taaaaaaaga gctcagagga ttcttatttt      360
tatttttagag cttttgctgg aatttttgtag aggtgaagac agtgtagacg ggaaaaacaa    420
aagtaccact gctttacctg ctgtaaaaga ctctgtaaaa gactcctagg taagtaatcc      480
cttttttttt gtatttccag gttcatgggt gctgctctag cacttttggg ggacctagtt      540
gccagtgtat ctgaggctgc tgctgccaca ggattttcag tggctgaaat tgctgctggg      600
gaggctgctg ctgctataga agttcaaatt gcatccctg ctactgtaga gggcataaca       660
agtacctcag aggctatagc tgctataggc ctaactcctc aaacatatgc tgtaattgct      720
ggtgctccag gggctattgc tgggtttgct gctttaattc aaactgttac tggtattagt      780
tctttggctc aagtagggta taggtttttt agtgattggg atcacaaagt ttccactgta      840
ggcctttatc agcaatcagg catggcattg gaattgttta acccagatga gtactatgat      900
attttgtttc ctggtgtaaa tacttttgta aataatattc aatacctaga tcctaggcat      960
tggggtcctt ctttgtttgc tactatttcc caggctttgt ggcatgttat tagggatgat     1020
atacctgcta taacttcaca agaattgcaa agaagaacag agagattctt tagagactcc     1080
ttggctagat ttttggaaga aactacctgg acaattgtaa atgcccctgt aaacttttat     1140
aattatattc aggattatta ttctaatttg tcccctatta ggccttcaat ggttaggcaa     1200
gttgctgaaa gggaaggaac ccaggtaaat tttggccata cctacagaat agatgatgct     1260
gacagtatac aagaagttac ccaaagaatg gagttaagaa ataaagagaa tgtacattca     1320
ggagagttta tagaaaaaac tattgcccca ggaggtgcta atcaaagaac tgctcctcaa     1380
tggatgttgc ctttgcttct aggcctgtac gggactgtaa cacctgctct tgaagcatat     1440
gaagatggcc ccaaccaaaa gaaaaggaga gtgtccaggg gcagctccca aaaagccaaa     1500
ggaacccgtg caagtgccaa aactactaat aaaaggagga gtagaagttc tagaagttaa     1560
aactgggggta gatgctataa cagaagtaga atgctttcta aatccagaat gggggatgcc     1620
agataatgac cttagggggct atagtctaag actaactgct gaaactgcct ttgacagtga     1680
tagcccagac agaaaaatgc ttccctgtta cagcacagca agaattccac tacctaatt     1740
gaatgaggat ctaacctgtg gaaatctact aatgtgggag gctgtgactg taaaaacaga     1800
ggttattgga ataactagta tgcttaacct tcatgcagga tcacagaaag tacatgaaaa     1860
tggtggaggc aaacctattc aaggcagcaa ttttcacttt tttgctgtgg gtggggaccc     1920
cttggaaatg cagggagtac ttatgaacta cagaacaaag tacccagaag gtactgtcac     1980
cccaaaaaat cccacagctc agtcccaggt aatgaatact gaccataagg cctacttgga     2040
caaaacaat gcttatccag ttgaatgctg gattcctgac cctagtagaa atgaaaatac     2100
taggtatttt ggaacataca caggagggga aaatgttccc ccagtacttc atgtaaccaa     2160
cacagctacc acagtgttgc tggatgaaca gggtgtgggg cctctgtgta agctgatag     2220
cctgtatgtt tcagctgctg atatttgtgg actgttact aacagctctg gaacacaaca     2280
gtggagggggc cttccaagat attttaagat tcgcctgaga aaaagatctg taaagaaccc     2340
ttacccaatt tcctttttgc ttagtgacct taaaacagg agaaacccga ggtgggtggg     2400
gcagcctatg tatggtatgg agtctcaggt ggaggaggtc agggtgttg atggcacaga     2460
acagcttcca ggggacccag atatgataag atatattgac agacagggac aattgcaaac     2520
aaaatggtt taaacaaggt gctttttattg tacatataca tgcttaataa atgctgcttt     2580
ttatattaca cattttaatc ttgtgttatt tggggggtgt tgttttagc cttttaaaac     2640
actgaaagcc tttacacaaa tgtaactctt cactatgggg gtctagcctt tgggaattct     2700
cagcaggggc tgaagtatct gagacttggg aagagcattg tgattgagat tcagtgcttg     2760
atccatgtcc agagtcttca gtttctgaat cttcttctct tgttatatca agaatacatt     2820
tccccatgca tatattatat ttcatccttg aaaaagtata catacttatc tcagaatcca     2880
gccttcctt ccattcaaca attctagact gtatatcttg tgcaaaatca gctacaggcc     2940
tgaaccaaat tagcagtagc agcaaggtca ttccactttg taatattctt ttttcaagta     3000
aaaattctga gttttgcagg gattttcta aataaattt aggtctaaaa tctatctgtc     3060
ttacaaatct agcctgcaag gttttgggga caggatactg attcattgta actaaacctg     3120
gtggaaatat ttgggttctt ttgttttaagt gttttctttc taaattaact ttgacacttc     3180
catctaaata atccctttaaa ctgtctaaat tgttattcc atgtcctgaa ggcaaatcct     3240
ttgattcagc tcctgttccc ttcacatctt caaaaacaac catatactga tctatagcca     3300
```

```
cacccagttc aaaagtaagc ctttccatgg gtaaattcac atttaaagct ttgcctccac    3360
ataaatctaa taaccctgca gctagtgttg ttttttccact atcaattgga cctttgaata    3420
accagtatct tctttaggt acattaaaaa caatacagtg caggaaatca aatataacag      3480
aatccatttt aggtagcaaa cagtgcagcc aggcaactcc tgccatatat tgttctagta    3540
cagcattttcc atgagctcca aatattaaat ccattttatc taatatatga ttaaatctgt   3600
ctgttagcat ttcttctctg gtcatatgga gggtatctac cctttttta gctaacactg     3660
tatccactgc ttgctgacaa atacttttt gattttact ttctgcaaaa atggtagcat       3720
ttgcaaaatg ctttttcatga tatttaaagt ggtagggttg gtcttttttt tgacactttt   3780
tacactcctc tacattgtac tgaaattcta aatacatacc caatagtaga aacacatctt    3840
cacactttgt ttctactgca tattcagtta ttaatttcca ggacacctgc tttgtttctt    3900
caggttcctc tgggttaaaa tcatgctcct ttaggccccc ttgaatactt tcctctatta    3960
tataatatgg atctctagtt aaggcactgt atagtaagta ttccttatta acacccttac    4020
aaattaaaaa actaaaagta cacagctttt gacagaaatt attaattgca gaaatctat     4080
gtctatgtgg agttaaaaag aatataaat tatgaccagc acacatgtgt ctactaataa    4140
aagttacaga atatttttcc ataagtttt tatacagaat taaagctttt tctttagtag   4200
tatacacagc aaagcaggca agagttctat tactaaatac agcttgacta agaaactggt  4260
gtagatcaga aggaaagtct ttagggtctt ctaccttct ttttttttttg ggtggtgttg   4320
agtgttggga atctgctgtt gcctcctcat cactggcaaa catatcttca tggcagaata   4380
aatcttcatc ccattttca ttaaaggacc tccaccagga ctcccactct tctgttccat    4440
aggttggcac ctataaaaaa aacataatta cttagggcct tcctataatt tactattatc    4500
taaagataaa ttagttacct taaagcttta gatctctgaa gggagtctct ccaattattt    4560
ggacccacca ttgcagagtt tcttcagtta ggtctaagcc aaaccactgt gtgaagcagt    4620
caatgcagta gcaatctatc caaccaagg gctcttttct taaaaattt ctatttaaat      4680
gtcttaatct tagctgacac agcatgcaag ggcagtgcac agaaggcttt ttggaacaaa    4740
taggccattc cttgcagtac aggggtatctg ggcaaagagg aaaatcagca caaacctctg   4800
agctactcca ggttccaaaa tcaggctggt gagctacctt tacatcctgc tccattttt     4860
tatataaaagt attcattctc ttcattttat cctcgtcgcc ccttttgtca gggtgaaatt   4920
ccttacactt tcttaaatag gctttcctca ttaagggaag gtttcccccag gcagctcttt   4980
caaggcctaa aagtcccatg agctccatgg attcctccct gtttagcact ttatccattt   5040
ttgcaaaaaa ttgcaaaaga atagggatt ccccaaatag ttttgctagg cctcagaaaa     5100
agcctccaca ccccttactac ttgagagaaa gggtggaggc agaggcg                 5147

SEQ ID NO: 51           moltype = DNA  length = 1111
FEATURE                 Location/Qualifiers
misc_feature            1..1111
                        note = partial BK virus sequence
source                  1..1111
                        mol_type = other DNA
                        organism = synthetic construct
SEQUENCE: 51
gactctgtaa aagactccta ggtaagtaat cccttttttt ttgtatttcc aggttcatgg    60
gtgctgctct agcacttttg ggggacctag ttgccagtgt atctgaggct gctgctgcca    120
caggattttc agtggctgaa attgctgctg gggaggctgc tgctgctata gaagttcaaa    180
ttgcatccct tgctactgta gagggcataa caagtacctc agaggctata gctgctatag    240
gcctaactcc tcaaacatat gctgtaattg ctggtgctcc aggggctatt gctgggtttg    300
ctgctttaat tcaaactgtt actggtatta gttcttggc tcaagtaggg tataggttt      360
ttagtgattg ggatcacaaa gtttccactg taggccttta tcagcaatca ggcatggcat    420
tggaattgtt taaccccagat gagtactatg atatttttgt tcctggtgta aatactttg    480
taaataatat tcaatacccta gatcctaggc attggggtcc ttctttgttt gctactattt   540
cccaggcttt gtggcatgtt attagggatg atatacctgc tataacttca caagaattgc    600
aaagaagaac agagagattc tttagagact ccttggctga attttggaa gaaactacct    660
ggacaattgt aaatgcccct gtaaactttt ataattatat tcaggattat tattctaatt    720
tgtcccctat taggccttca atggttaggc aagttgctga aagggaagga acccaggtaa    780
attttggcca tacctacaga atagatgatg ctgacagtat acaagaagtt acccaaagaa    840
tggagttaag aaataaagag aatgtacatt caggagagtt tataagaaaa actattgccc    900
caggaggtgc taatcaaaga actgctcctc aatggatgtt gcctttgctt ctaggcctgt    960
acgggactgt aacacctgct cttgaagcat atgaagatgg ccccaaccaa aagaaaagga    1020
gagtgtccag gggcagctcc caaaaagcca aggaacccg tgcaagtgcc aaaactacta    1080
ataaaaggag gagtagaagt tctagaagtt a                                    1111

SEQ ID NO: 52           moltype = DNA  length = 148
FEATURE                 Location/Qualifiers
misc_feature            1..148
                        note = partial BK virus sequence
source                  1..148
                        mol_type = other DNA
                        organism = synthetic construct
SEQUENCE: 52
ctacctttac atcctgctcc attttttat ataagtatt cattctcttc attttatcct       60
cgtcgcccc tttgtcaggg tgaaattcct tacactttct taaataggct ttcctcatta    120
agggaaggtt tccccaggca gctctttc                                       148

SEQ ID NO: 53           moltype = DNA  length = 20
FEATURE                 Location/Qualifiers
misc_feature            1..20
                        note = synthetic oligonucleotide
source                  1..20
                        mol_type = other DNA
                        organism = synthetic construct
```

```
SEQUENCE: 53
atggtcaatt agagacaaag                                                    20

SEQ ID NO: 54          moltype = DNA  length = 20
FEATURE                Location/Qualifiers
misc_feature           1..20
                       note = synthetic oligonucleotide
source                 1..20
                       mol_type = other DNA
                       organism = synthetic construct
SEQUENCE: 54
cgttcactat tggtctctgc                                                    20

SEQ ID NO: 55          moltype = DNA  length = 26
FEATURE                Location/Qualifiers
misc_feature           1..26
                       note = synthetic oligonucleotide
source                 1..26
                       mol_type = other DNA
                       organism = synthetic construct
SEQUENCE: 55
cggaatcaca agtcaatcat cgcgca                                             26
```